(12) United States Patent
Terrett et al.

(10) Patent No.: US 12,344,656 B2
(45) Date of Patent: Jul. 1, 2025

(54) GENETICALLY ENGINEERED T CELLS HAVING IMPROVED PERSISTENCE IN CULTURE

(71) Applicant: CRISPR Therapeutics AG, Zug (CH)

(72) Inventors: Jonathan Alexander Terrett, Cambridge, MA (US); Demetrios Kalaitzidis, Cambridge, MA (US); Hanspeter Waldner, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 503 days.

(21) Appl. No.: 17/012,957

(22) Filed: Sep. 4, 2020

(65) Prior Publication Data

US 2021/0079347 A1   Mar. 18, 2021

Related U.S. Application Data

(60) Provisional application No. 63/034,646, filed on Jun. 4, 2020, provisional application No. 62/927,764, filed on Oct. 30, 2019, provisional application No. 62/897,016, filed on Sep. 6, 2019.

(51) Int. Cl.

| | | |
|---|---|---|
| *C07K 14/705* | (2006.01) | |
| *A61K 31/7105* | (2006.01) | |
| *A61K 40/11* | (2025.01) | |
| *A61K 40/31* | (2025.01) | |
| *A61K 40/42* | (2025.01) | |
| *A61K 40/50* | (2025.01) | |
| *C12N 5/0783* | (2010.01) | |
| *C12N 9/22* | (2006.01) | |
| *C12N 15/113* | (2010.01) | |

(52) U.S. Cl.
CPC .... *C07K 14/70596* (2013.01); *A61K 31/7105* (2013.01); *A61K 40/11* (2025.01); *A61K 40/31* (2025.01); *A61K 40/4202* (2025.01); *A61K 40/4211* (2025.01); *A61K 40/4215* (2025.01); *C12N 5/0636* (2013.01); *C12N 9/22* (2013.01); *C12N 15/113* (2013.01); *A61K 40/50* (2025.01); *A61K 2239/31* (2023.05); *A61K 2239/38* (2023.05); *A61K 2239/48* (2023.05); *C12N 2310/20* (2017.05); *C12N 2510/00* (2013.01)

(58) Field of Classification Search
CPC ........................ C12N 5/0636; C12N 2510/00
See application file for complete search history.

(56) References Cited

U.S. PATENT DOCUMENTS

| | | | |
|---|---|---|---|
| 2018/0201901 A1* | 7/2018 | Duchateau | A61K 39/4644 |
| 2018/0258149 A1 | 9/2018 | Motz et al. | |
| 2019/0175651 A1 | 6/2019 | Lee et al. | |
| 2019/0233528 A1 | 8/2019 | Srivatsa Srinivasan et al. | |

FOREIGN PATENT DOCUMENTS

| | | | |
|---|---|---|---|
| WO | 2016/069282 A1 | 5/2016 | |
| WO | 2017/049166 A1 | 3/2017 | |
| WO | 2017/193107 A2 | 11/2017 | |
| WO | 2018/007263 A1 | 1/2018 | |
| WO | WO-2018030874 A1 * | 2/2018 | ............ A61K 35/14 |
| WO | 2018/175733 A1 | 9/2018 | |
| WO | 2019/018553 A1 | 1/2019 | |
| WO | 2019/215500 A1 | 11/2019 | |
| WO | 2020/223478 A1 | 11/2020 | |

OTHER PUBLICATIONS

Bryder et al. Self-renewal of multipotent long-term repopulating hematopoietic stem cells is negatively regulated by Fas and tumor necrosis factor receptor activation. Journal of Experimental Medicine 2001, 194;7:941-952. (Year: 2001).*
Li et al. The transcription factors Egr2 and Egr3 are essential for the control of inflammation and antigen-induced proliferation of B and T cells. Immunity 2012, 37:685-696. (Year: 2012).*
Ren et al. Multiplex genome editing to generate universal CAR T cells resistant to PD1 inhibition. Clinical Cancer Research 2017, 23;9:2255-2266. (Year: 2017).*
MacLeod et al. Integration of a CD19 CAR into the TCR alpha chain locus streamlines production of allogeneic gene-edited CAR T cells. Molecular Therapy 2017, 25;4:949-961. (Year: 2017).*
Muto et al. Reduced TET2 function leads to T-cell lymphoma with follicular helper T-cell-like features in mice. Blood Cancer Journal 2014, 4:e264. (Year: 2014).*
Munitic et al. CD70 Delciency Impairs Eyector CD8 T Cell Generation and Viral Clearance but Is Dispensable for the Recall Response to Lymphocytic Choriomeningitis Virus. Journal of Immunology 2013, 190;3:1169-1179. (Year: 2013).*
Fraietta et al., Disruption of TET2 Promotes the Therapeutic Efficacy of CD19-targeted T-cells. Nature. Jun. 2018; 558(7709):307-12.
Mollanoori et al., CRISPR/Cas9 and CAR-T cell, collaboration of two revolutionary technologies in cancer immunotherapy, an instruction for successful cancer treatment. Hum Immunol. Dec. 2018;79(12):876-882. doi: 10.1016/j.humimm.2018.09.007. Epub Sep. 24, 2018.
Long, A. et al. 4-1BB Costimulation Ameliorates T Cell Exhaustion Induced by Tonic Signaling of Chimeric Antigen Receptors, Nat Med. Jun. 2015 ; 21(6): 581-590. doi:10.1038/nm.3838.

(Continued)

Primary Examiner — Christopher M Babic
Assistant Examiner — Jennifer S Spence
(74) Attorney, Agent, or Firm — Casimir Jones, S.C.; J. Mitchell Jones

(57) ABSTRACT

A T cell bank comprising genetically engineered T cells having one or more of the following features as compared to the non-engineered T cell counterparts: (a) enhanced expansion capacity in culture, (b) enhanced proliferation capacity, (c) reduced apoptosis, and (d) enhanced activation frequencies. Such genetically engineered T cells may comprise (i) a mutated gene involved in cell self-renewal; (ii) a disrupted gene involved in apoptosis; (iii) a disrupted gene involved in regulation of T cell exhaustion; or (iv) a combination of any one of (i)-(iii).

13 Claims, 15 Drawing Sheets

Specification includes a Sequence Listing.

(56) References Cited

OTHER PUBLICATIONS

Calderon, H. et al. Analysis of CAR-Mediated Tonic Signaling (2020), Kamilla Swiech et al. (eds.), Chimeric Antigen Receptor T Cells: Development and Production, Methods in Molecular Biology, vol. 2086, pp. 223-236.

* cited by examiner

SEQUENCE LISTING

```
<160> NUMBER OF SEQ ID NOS: 241

<210> SEQ ID NO 1
<211> LENGTH: 79
<212> TYPE: DNA
<213> ORGANISM: Artificial Sequence
<220> FEATURE:
<223> OTHER INFORMATION: Synthetic

<400> SEQUENCE: 1
cgtggcctta gctgtgctcg cgctactctc tctttctgcc tggaggctat ccagcgtgag     60
tctctcctac cctcccgct                                                 79

<210> SEQ ID NO 2
<211> LENGTH: 78
<212> TYPE: DNA
<213> ORGANISM: Artificial Sequence
<220> FEATURE:
<223> OTHER INFORMATION: Synthetic

<400> SEQUENCE: 2
cgtggcctta gctgtgctcg cgctactctc tctttcgcct ggaggctatc cagcgtgagt     60
ctctcctacc ctcccgct                                                  78

<210> SEQ ID NO 3
<211> LENGTH: 75
<212> TYPE: DNA
<213> ORGANISM: Artificial Sequence
<220> FEATURE:
<223> OTHER INFORMATION: Synthetic

<400> SEQUENCE: 3
cgtggcctta gctgtgctcg cgctactctc tctttctgga ggctatccag cgtgagtctc     60
tcctaccctc ccgct                                                     75

<210> SEQ ID NO 4
<211> LENGTH: 84
<212> TYPE: DNA
<213> ORGANISM: Artificial Sequence
<220> FEATURE:
<223> OTHER INFORMATION: Synthetic

<400> SEQUENCE: 4
cgtggcctta gctgtgctcg cgctactctc tctttctgga tagcctggag gctatccagc     60
gtgagtctct cctaccctcc cgct                                           84

<210> SEQ ID NO 5
<211> LENGTH: 55
<212> TYPE: DNA
<213> ORGANISM: Artificial Sequence
<220> FEATURE:
<223> OTHER INFORMATION: Synthetic

<400> SEQUENCE: 5
cgtggcctta gctgtgctcg cgctatccag cgtgagtctc tcctaccctc ccgct         55

<210> SEQ ID NO 6
```

```
<211> LENGTH: 82
<212> TYPE: DNA
<213> ORGANISM: Artificial Sequence
<220> FEATURE:
<223> OTHER INFORMATION: Synthetic

<400> SEQUENCE: 6
cgtggcctta gctgtgctcg cgctactctc tctttctgtg gcctggaggc tatccagcgt    60
gagtctctcc taccctcccg ct                                             82

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
agagcaacag tgctgtggcc                                                20

<210> SEQ ID NO 8
<211> LENGTH: 20
<212> TYPE: RNA
<213> ORGANISM: Artificial Sequence
<220> FEATURE:
<223> OTHER INFORMATION: Synthetic

<400> SEQUENCE: 8
agagcaacag ugcuguggcc                                                20

<210> SEQ ID NO 9
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 9
nnnnnnnnnn nnnnnnnnnn guuuuagagc uagaaauagc aaguuaaaau aaggcuaguc    60
cguuaucaac uugaaaaagu ggcaccgagu cggugcuuuu                          100

<210> SEQ ID NO 10
<211> LENGTH: 96
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 10
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 11
<211> LENGTH: 114
<212> TYPE: RNA
<213> ORGANISM: Artificial Sequence
<220> FEATURE:
<223> OTHER INFORMATION: Synthetic
```

<220> FEATURE:
<221> NAME/KEY: misc_feature
<222> LOCATION: (1)..(17)
<223> OTHER INFORMATION: n is a, c, g, or u
<220> FEATURE:
<221> NAME/KEY: misc_feature
<222> LOCATION: (18)..(30)
<223> OTHER INFORMATION: may be absent
<220> FEATURE:
<221> NAME/KEY: misc_feature
<222> LOCATION: (108)..(114)
<223> OTHER INFORMATION: may be absent

<400> SEQUENCE: 11
nnnnnnnnnn nnnnnnnnnn nnnnnnnnnn guuuuagagc uagaaauagc aaguuaaaau    60
aaggcuaguc cguuaucaac uugaaaaagu ggcaccgagu cggugcuuuu uuuu         114

<210> SEQ ID NO 12
<211> LENGTH: 100
<212> TYPE: RNA
<213> ORGANISM: Artificial Sequence
<220> FEATURE:
<223> OTHER INFORMATION: Synthetic

<400> SEQUENCE: 12
cauuaggacc ugcuccuaga guuuuagagc uagaaauagc aaguuaaaau aaggcuaguc    60
cguuaucaac uugaaaaagu ggcaccgagu cggugcuuuu                        100

<210> SEQ ID NO 13
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 13
cauuaggacc ugcuccuaga guuuuagagc uagaaauagc aaguuaaaau aaggcuaguc    60
cguuaucaac uugaaaaagu ggcaccgagu cggugcuuuu                        100

<210> SEQ ID NO 14
<211> LENGTH: 20
<212> TYPE: RNA
<213> ORGANISM: Artificial Sequence
<220> FEATURE:
<223> OTHER INFORMATION: Synthetic

<400> SEQUENCE: 14
cauuaggacc ugcuccuaga                                               20

<210> SEQ ID NO 15
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

```
<400> SEQUENCE: 15
cauuaggacc ugcuccuaga                                              20

<210> SEQ ID NO 16
<211> LENGTH: 100
<212> TYPE: RNA
<213> ORGANISM: Artificial Sequence
<220> FEATURE:
<223> OTHER INFORMATION: Synthetic

<400> SEQUENCE: 16
gggauguccu auugcuaagu guuuuagagc uagaaauagc aaguuaaaau aaggcuaguc   60
cguuaucaac uugaaaaagu ggcaccgagu cggugcuuuu                       100

<210> SEQ ID NO 17
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 17
gggauguccu auugcuaagu guuuuagagc uagaaauagc aaguuaaaau aaggcuaguc   60
cguuaucaac uugaaaaagu ggcaccgagu cggugcuuuu                       100

<210> SEQ ID NO 18
<211> LENGTH: 20
<212> TYPE: RNA
<213> ORGANISM: Artificial Sequence
<220> FEATURE:
<223> OTHER INFORMATION: Synthetic

<400> SEQUENCE: 18
gggauguccu auugcuaagu                                              20

<210> SEQ ID NO 19
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 19
gggauguccu auugcuaagu                                              20

<210> SEQ ID NO 20
<211> LENGTH: 100
<212> TYPE: RNA
<213> ORGANISM: Artificial Sequence
<220> FEATURE:
<223> OTHER INFORMATION: Synthetic

<400> SEQUENCE: 20
agggaugucc uauugcuaag guuuuagagc uagaaauagc aaguuaaaau aaggcuaguc   60
```

```
cguuaucaac uugaaaaagu ggcaccgagu cggugcuuuu                    100
```

<210> SEQ ID NO 21
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 21

```
agggaugucc uauugcuaag guuuuagagc uagaaauagc aaguuaaaau aaggcuaguc    60
cguuaucaac uugaaaaagu ggcaccgagu cggugcuuuu                        100
```

<210> SEQ ID NO 22
<211> LENGTH: 20
<212> TYPE: RNA
<213> ORGANISM: Artificial Sequence
<220> FEATURE:
<223> OTHER INFORMATION: Synthetic

<400> SEQUENCE: 22

```
agggaugucc uauugcuaag                                              20
```

<210> SEQ ID NO 23
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 23

```
agggaugucc uauugcuaag                                              20
```

<210> SEQ ID NO 24
<211> LENGTH: 99
<212> TYPE: RNA
<213> ORGANISM: Artificial Sequence
<220> FEATURE:
<223> OTHER INFORMATION: Synthetic

<400> SEQUENCE: 24

```
acggcacgcu caccaaucgc guuuugagcu agaaauagca aguuaaaaua aggcuagucc    60
guuaucaacu ugaaaagug gcaccgaguc ggugcuuuu                           99
```

<210> SEQ ID NO 25
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:

```
<221> NAME/KEY: misc_feature
<222> LOCATION: (97)..(100)
<223> OTHER INFORMATION: modified with 2'-O-methyl phosphorothioate

<400> SEQUENCE: 25
acggcacgcu caccaaucgc guuuuagagc uagaaauagc aaguuaaaau aaggcuaguc    60
cguuaucaac uugaaaaagu ggcaccgagu cggugcuuuu                         100

<210> SEQ ID NO 26
<211> LENGTH: 20
<212> TYPE: RNA
<213> ORGANISM: Artificial Sequence
<220> FEATURE:
<223> OTHER INFORMATION: Synthetic

<400> SEQUENCE: 26
acggcacgcu caccaaucgc                                                20

<210> SEQ ID NO 27
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 27
acggcacgcu caccaaucgc                                                20

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
cattaggacc tgctcctaga tgg                                            23

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
gggatgtcct attgctaagt ggg                                            23

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
agggatgtcc tattgctaag tgg                                            23

<210> SEQ ID NO 31
<211> LENGTH: 23
<212> TYPE: DNA
<213> ORGANISM: Artificial Sequence
```

```
<220> FEATURE:
<223> OTHER INFORMATION: Synthetic

<400> SEQUENCE: 31
acggcacgct caccaatcgc cgg                                              23

<210> SEQ ID NO 32
<211> LENGTH: 100
<212> TYPE: RNA
<213> ORGANISM: Artificial Sequence
<220> FEATURE:
<223> OTHER INFORMATION: Synthetic

<400> SEQUENCE: 32
ucaccaagcc cgcgaccaau guuuuagagc uagaaauagc aaguuaaaau aaggcuaguc       60
cguuaucaac uugaaaaagu ggcaccgagu cggugcuuuu                           100

<210> SEQ ID NO 33
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 33
ucaccaagcc cgcgaccaau guuuuagagc uagaaauagc aaguuaaaau aaggcuaguc       60
cguuaucaac uugaaaaagu ggcaccgagu cggugcuuuu                           100

<210> SEQ ID NO 34
<211> LENGTH: 20
<212> TYPE: RNA
<213> ORGANISM: Artificial Sequence
<220> FEATURE:
<223> OTHER INFORMATION: Synthetic

<400> SEQUENCE: 34
ucaccaagcc cgcgaccaau                                                  20

<210> SEQ ID NO 35
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 35
ucaccaagcc cgcgaccaau                                                  20

<210> SEQ ID NO 36
<211> LENGTH: 100
<212> TYPE: RNA
<213> ORGANISM: Artificial Sequence
<220> FEATURE:
<223> OTHER INFORMATION: Synthetic
```

<400> SEQUENCE: 36
aucaccaagc ccgcgaccaa guuuuagagc uagaaauagc aaguuaaaau aaggcuaguc    60
cguuaucaac uugaaaaagu ggcaccgagu cggugcuuuu                         100

<210> SEQ ID NO 37
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 37
aucaccaagc ccgcgaccaa guuuuagagc uagaaauagc aaguuaaaau aaggcuaguc    60
cguuaucaac uugaaaaagu ggcaccgagu cggugcuuuu                         100

<210> SEQ ID NO 38
<211> LENGTH: 20
<212> TYPE: RNA
<213> ORGANISM: Artificial Sequence
<220> FEATURE:
<223> OTHER INFORMATION: Synthetic

<400> SEQUENCE: 38
aucaccaagc ccgcgaccaa                                               20

<210> SEQ ID NO 39
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 39
aucaccaagc ccgcgaccaa                                               20

<210> SEQ ID NO 40
<211> LENGTH: 100
<212> TYPE: RNA
<213> ORGANISM: Artificial Sequence
<220> FEATURE:
<223> OTHER INFORMATION: Synthetic

<400> SEQUENCE: 40
cggugcggcg caggcccuau guuuuagagc uagaaauagc aaguuaaaau aaggcuaguc    60
cguuaucaac uugaaaaagu ggcaccgagu cggugcuuuu                         100

<210> SEQ ID NO 41
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 41
cggugcggcg caggcccuau guuuagagc uagaaauagc aaguuaaaau aaggcuaguc    60
cguuaucaac uugaaaaagu ggcaccgagu cggugcuuuu                       100

<210> SEQ ID NO 42
<211> LENGTH: 20
<212> TYPE: RNA
<213> ORGANISM: Artificial Sequence
<220> FEATURE:
<223> OTHER INFORMATION: Synthetic

<400> SEQUENCE: 42
cggugcggcg caggcccuau                                              20

<210> SEQ ID NO 43
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 43
cggugcggcg caggcccuau                                              20

<210> SEQ ID NO 44
<211> LENGTH: 100
<212> TYPE: RNA
<213> ORGANISM: Artificial Sequence
<220> FEATURE:
<223> OTHER INFORMATION: Synthetic

<400> SEQUENCE: 44 gcuuggucc cauuggucgc guuuagagc uagaaauagc aaguuaaaau aaggcuaguc    60
cguuaucaac uugaaaaagu ggcaccgagu cggugcuuuu                       100

<210> SEQ ID NO 45
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 45 gcuuggucc cauuggucgc guuuagagc uagaaauagc aaguuaaaau aaggcuaguc    60
cguuaucaac uugaaaaagu ggcaccgagu cggugcuuuu                       100

<210> SEQ ID NO 46
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 46 gcuuggucc cauuggucgc                                                    20

<210> SEQ ID NO 47
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 47 gcuuggucc cauuggucgc                                                    20

<210> SEQ ID NO 48
<211> LENGTH: 100
<212> TYPE: RNA
<213> ORGANISM: Artificial Sequence
<220> FEATURE:
<223> OTHER INFORMATION: Synthetic

<400> SEQUENCE: 48
gcccgcagga cgcacccaua guuuuagagc uagaaauagc aaguuaaaau aaggcuaguc        60
cguuaucaac uugaaaaagu ggcaccgagu cggugcuuuu                             100

<210> SEQ ID NO 49
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 49
gcccgcagga cgcacccaua guuuuagagc uagaaauagc aaguuaaaau aaggcuaguc        60
cguuaucaac uugaaaaagu ggcaccgagu cggugcuuuu                             100

<210> SEQ ID NO 50
<211> LENGTH: 20
<212> TYPE: RNA
<213> ORGANISM: Artificial Sequence
<220> FEATURE:
<223> OTHER INFORMATION: Synthetic

<400> SEQUENCE: 50
gcccgcagga cgcacccaua                                                   20

<210> SEQ ID NO 51
<211> LENGTH: 20
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 51
gcccgcagga cgcacccaua                                               20

<210> SEQ ID NO 52
<211> LENGTH: 100
<212> TYPE: RNA
<213> ORGANISM: Artificial Sequence
<220> FEATURE:
<223> OTHER INFORMATION: Synthetic

<400> SEQUENCE: 52
gugcauccag cgcuucgcac guuuuagagc uagaaauagc aaguuaaaau aaggcuaguc    60
cguuaucaac uugaaaaagu ggcaccgagu cggugcuuuu                        100

<210> SEQ ID NO 53
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 53
gugcauccag cgcuucgcac guuuuagagc uagaaauagc aaguuaaaau aaggcuaguc    60
cguuaucaac uugaaaaagu ggcaccgagu cggugcuuuu                        100

<210> SEQ ID NO 54
<211> LENGTH: 20
<212> TYPE: RNA
<213> ORGANISM: Artificial Sequence
<220> FEATURE:
<223> OTHER INFORMATION: Synthetic

<400> SEQUENCE: 54
gugcauccag cgcuucgcac                                               20

<210> SEQ ID NO 55
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 55
gugcauccag cgcuucgcac                                               20

<210> SEQ ID NO 56
<211> LENGTH: 100
<212> TYPE: RNA
```

```
<213> ORGANISM: Artificial Sequence
<220> FEATURE:
<223> OTHER INFORMATION: Synthetic

<400> SEQUENCE: 56
cagcuacgua uccaucguga guuuuagagc uagaaauagc aaguuaaaau aaggcuaguc    60
cguuaucaac uugaaaaagu ggcaccgagu cggugcuuuu                        100

<210> SEQ ID NO 57
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 57
cagcuacgua uccaucguga guuuuagagc uagaaauagc aaguuaaaau aaggcuaguc    60
cguuaucaac uugaaaaagu ggcaccgagu cggugcuuuu                        100

<210> SEQ ID NO 58
<211> LENGTH: 20
<212> TYPE: RNA
<213> ORGANISM: Artificial Sequence
<220> FEATURE:
<223> OTHER INFORMATION: Synthetic

<400> SEQUENCE: 58
cagcuacgua uccaucguga                                               20

<210> SEQ ID NO 59
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 59
cagcuacgua uccaucguga                                               20

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
tcaccaagcc cgcgaccaat ggg                                           23

<210> SEQ ID NO 61
<211> LENGTH: 23
<212> TYPE: DNA
<213> ORGANISM: Artificial Sequence
<220> FEATURE:
<223> OTHER INFORMATION: Synthetic
```

<400> SEQUENCE: 61
atcaccaagc ccgcgaccaa tgg					23

<210> SEQ ID NO 62
<211> LENGTH: 23
<212> TYPE: DNA
<213> ORGANISM: Artificial Sequence
<220> FEATURE:
<223> OTHER INFORMATION: Synthetic

<400> SEQUENCE: 62
cggtgcggcg caggccctat ggg					23

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
gctttggtcc cattggtcgc ggg					23

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
gcccgcagga cgcacccata ggg					23

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
gtgcatccag cgcttcgcac agg					23

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
cagctacgta tccatcgtga tgg					23

<210> SEQ ID NO 67
<211> LENGTH: 100
<212> TYPE: RNA
<213> ORGANISM: Artificial Sequence
<220> FEATURE:
<223> OTHER INFORMATION: Synthetic

<400> SEQUENCE: 67
gugacugaca ucaacuccaa guuuuagagc uagaaauagc aaguuaaaau aaggcuaguc		60 cguuaucaac uugaaaaagu ggcaccgagu cggugcuuuu				100

```
<210> SEQ ID NO 68
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 68
gugacugaca ucaacuccaa guuuuagagc uagaaauagc aaguuaaaau aaggcuaguc    60
cguuaucaac uugaaaaagu ggcaccgagu cggugcuuuu                        100

<210> SEQ ID NO 69
<211> LENGTH: 20
<212> TYPE: RNA
<213> ORGANISM: Artificial Sequence
<220> FEATURE:
<223> OTHER INFORMATION: Synthetic

<400> SEQUENCE: 69
gugacugaca ucaacuccaa                                               20

<210> SEQ ID NO 70
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 70
gugacugaca ucaacuccaa                                               20

<210> SEQ ID NO 71
<211> LENGTH: 100
<212> TYPE: RNA
<213> ORGANISM: Artificial Sequence
<220> FEATURE:
<223> OTHER INFORMATION: Synthetic

<400> SEQUENCE: 71
cacuugggca uuaacacuuu guuuuagagc uagaaauagc aaguuaaaau aaggcuaguc    60
cguuaucaac uugaaaaagu ggcaccgagu cggugcuuuu                        100

<210> SEQ ID NO 72
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate
```

<400> SEQUENCE: 72
cacuugggca uuaacacuuu guuuuagagc uagaaauagc aaguuaaaau aaggcuaguc    60
cguuaucaac uugaaaaagu ggcaccgagu cggugcuuuu                         100

<210> SEQ ID NO 73
<211> LENGTH: 20
<212> TYPE: RNA
<213> ORGANISM: Artificial Sequence
<220> FEATURE:
<223> OTHER INFORMATION: Synthetic

<400> SEQUENCE: 73
cacuugggca uuaacacuuu                                               20

<210> SEQ ID NO 74
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 74
cacuugggca uuaacacuuu                                               20

<210> SEQ ID NO 75
<211> LENGTH: 100
<212> TYPE: RNA
<213> ORGANISM: Artificial Sequence
<220> FEATURE:
<223> OTHER INFORMATION: Synthetic

<400> SEQUENCE: 75
uuggaaggcc ugcaucauga guuuuagagc uagaaauagc aaguuaaaau aaggcuaguc    60
cguuaucaac uugaaaaagu ggcaccgagu cggugcuuuu                         100

<210> SEQ ID NO 76
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 76
uuggaaggcc ugcaucauga guuuuagagc uagaaauagc aaguuaaaau aaggcuaguc    60
cguuaucaac uugaaaaagu ggcaccgagu cggugcuuuu                         100

<210> SEQ ID NO 77
<211> LENGTH: 20
<212> TYPE: RNA
<213> ORGANISM: Artificial Sequence
<220> FEATURE:
<223> OTHER INFORMATION: Synthetic

<400> SEQUENCE: 77
uuggaaggcc ugcaucauga                                                                      20

<210> SEQ ID NO 78
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 78
uuggaaggcc ugcaucauga                                                                      20

<210> SEQ ID NO 79
<211> LENGTH: 100
<212> TYPE: RNA
<213> ORGANISM: Artificial Sequence
<220> FEATURE:
<223> OTHER INFORMATION: Synthetic

<400> SEQUENCE: 79
cuagggacug cacagucaau guuuuagagc uagaaauagc aaguuaaaau aaggcuaguc          60
cguuaucaac uugaaaaagu ggcaccgagu cggugcuuuu                              100

<210> SEQ ID NO 80
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 80
cuagggacug cacagucaau guuuuagagc uagaaauagc aaguuaaaau aaggcuaguc          60
cguuaucaac uugaaaaagu ggcaccgagu cggugcuuuu                              100

<210> SEQ ID NO 81
<211> LENGTH: 20
<212> TYPE: RNA
<213> ORGANISM: Artificial Sequence
<220> FEATURE:
<223> OTHER INFORMATION: Synthetic

<400> SEQUENCE: 81
cuagggacug cacagucaau                                                                      20

<210> SEQ ID NO 82
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 82
cuagggacug cacagucaau            20

<210> SEQ ID NO 83
<211> LENGTH: 100
<212> TYPE: RNA
<213> ORGANISM: Artificial Sequence
<220> FEATURE:
<223> OTHER INFORMATION: Synthetic

<400> SEQUENCE: 83
acugcgugcc cugccaagaa guuuuagagc uagaaauagc aaguuaaaau aaggcuaguc            60
cguuaucaac uugaaaaagu ggcaccgagu cggugcuuuu            100

<210> SEQ ID NO 84
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 84
acugcgugcc cugccaagaa guuuuagagc uagaaauagc aaguuaaaau aaggcuaguc            60
cguuaucaac uugaaaaagu ggcaccgagu cggugcuuuu            100

<210> SEQ ID NO 85
<211> LENGTH: 20
<212> TYPE: RNA
<213> ORGANISM: Artificial Sequence
<220> FEATURE:
<223> OTHER INFORMATION: Synthetic

<400> SEQUENCE: 85
acugcgugcc cugccaagaa            20

<210> SEQ ID NO 86
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 86
acugcgugcc cugccaagaa            20

<210> SEQ ID NO 87
<211> LENGTH: 23
<212> TYPE: DNA
<213> ORGANISM: Artificial Sequence
<220> FEATURE:
<223> OTHER INFORMATION: Synthetic

<400> SEQUENCE: 87

```
gtgactgaca tcaactccaa ggg                                              23

<210> SEQ ID NO 88
<211> LENGTH: 23
<212> TYPE: DNA
<213> ORGANISM: Artificial Sequence
<220> FEATURE:
<223> OTHER INFORMATION: Synthetic

<400> SEQUENCE: 88
cacttgggca ttaacacttt tgg                                              23

<210> SEQ ID NO 89
<211> LENGTH: 23
<212> TYPE: DNA
<213> ORGANISM: Artificial Sequence
<220> FEATURE:
<223> OTHER INFORMATION: Synthetic

<400> SEQUENCE: 89
ttggaaggcc tgcatcatga tgg                                              23

<210> SEQ ID NO 90
<211> LENGTH: 23
<212> TYPE: DNA
<213> ORGANISM: Artificial Sequence
<220> FEATURE:
<223> OTHER INFORMATION: Synthetic

<400> SEQUENCE: 90
ctagggactg cacagtcaat ggg                                              23

<210> SEQ ID NO 91
<211> LENGTH: 23
<212> TYPE: DNA
<213> ORGANISM: Artificial Sequence
<220> FEATURE:
<223> OTHER INFORMATION: Synthetic

<400> SEQUENCE: 91
actgcgtgcc ctgccaagaa ggg                                              23

<210> SEQ ID NO 92
<211> LENGTH: 100
<212> TYPE: RNA
<213> ORGANISM: Artificial Sequence
<220> FEATURE:
<223> OTHER INFORMATION: Synthetic

<400> SEQUENCE: 92
agagcaacag ugcuguggcc guuuuagagc uagaaauagc aaguuaaaau aaggcuaguc      60
cguuaucaac uugaaaaagu ggcaccgagu cggugcuuuu                           100

<210> SEQ ID NO 93
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate
```

<400> SEQUENCE: 93
agagcaacag ugcuguggcc guuuuagagc uagaaauagc aaguuaaaau aaggcuaguc        60
cguuaucaac uugaaaaagu ggcaccgagu cggugcuuuu                             100

<210> SEQ ID NO 94
<211> LENGTH: 20
<212> TYPE: RNA
<213> ORGANISM: Artificial Sequence
<220> FEATURE:
<223> OTHER INFORMATION: Synthetic

<400> SEQUENCE: 94
agagcaacag ugcuguggcc                                                   20

<210> SEQ ID NO 95
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 95
agagcaacag ugcuguggcc                                                   20

<210> SEQ ID NO 96
<211> LENGTH: 100
<212> TYPE: RNA
<213> ORGANISM: Artificial Sequence
<220> FEATURE:
<223> OTHER INFORMATION: Synthetic

<400> SEQUENCE: 96
gcuacucucu cuuucuggcc guuuuagagc uagaaauagc aaguuaaaau aaggcuaguc        60
cguuaucaac uugaaaaagu ggcaccgagu cggugcuuuu                             100

<210> SEQ ID NO 97
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 97
gcuacucucu cuuucuggcc guuuuagagc uagaaauagc aaguuaaaau aaggcuaguc        60
cguuaucaac uugaaaaagu ggcaccgagu cggugcuuuu                             100

<210> SEQ ID NO 98
<211> LENGTH: 20
<212> TYPE: RNA
<213> ORGANISM: Artificial Sequence
<220> FEATURE:
<223> OTHER INFORMATION: Synthetic -continued

```
<400> SEQUENCE: 98
gcuacucucu cuuucuggcc                                                  20

<210> SEQ ID NO 99
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 99
gcuacucucu cuuucuggcc                                                  20

<210> SEQ ID NO 100
<211> LENGTH: 23
<212> TYPE: DNA
<213> ORGANISM: Artificial Sequence
<220> FEATURE:
<223> OTHER INFORMATION: Synthetic

<400> SEQUENCE: 100
agagcaacag tgctgtggcc tgg                                              23

<210> SEQ ID NO 101
<211> LENGTH: 23
<212> TYPE: DNA
<213> ORGANISM: Artificial Sequence
<220> FEATURE:
<223> OTHER INFORMATION: Synthetic

<400> SEQUENCE: 101
gctactctct ctttctggcc tgg                                              23

<210> SEQ ID NO 102
<211> LENGTH: 22
<212> TYPE: PRT
<213> ORGANISM: Artificial Sequence
<220> FEATURE:
<223> OTHER INFORMATION: Synthetic

<400> SEQUENCE: 102

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 103
<211> LENGTH: 21
<212> TYPE: PRT
<213> ORGANISM: Artificial Sequence
<220> FEATURE:
<223> OTHER INFORMATION: Synthetic

<400> SEQUENCE: 103

Met Ala Leu Pro Val Thr Ala Leu Leu Leu Pro Leu Ala Leu Leu Leu
1               5                   10                  15

His Ala Ala Arg Pro
            20

<210> SEQ ID NO 104
<211> LENGTH: 84
```

```
<212> TYPE: PRT
<213> ORGANISM: Artificial Sequence
<220> FEATURE:
<223> OTHER INFORMATION: Synthetic

<400> SEQUENCE: 104

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 105
<211> LENGTH: 23
<212> TYPE: PRT
<213> ORGANISM: Artificial Sequence
<220> FEATURE:
<223> OTHER INFORMATION: Synthetic

<400> SEQUENCE: 105

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 106
<211> LENGTH: 126
<212> TYPE: DNA
<213> ORGANISM: Artificial Sequence
<220> FEATURE:
<223> OTHER INFORMATION: Synthetic

<400> SEQUENCE: 106 aaacgggca gaaagaaact cctgtatata ttcaaacaac catttatgag accagtacaa      60
actactcaag aggaagatgg ctgtagctgc cgatttccag aagaagaaga aggaggatgt    120
gaactg                                                              126

<210> SEQ ID NO 107
<211> LENGTH: 42
<212> TYPE: PRT
<213> ORGANISM: Artificial Sequence
<220> FEATURE:
<223> OTHER INFORMATION: Synthetic

<400> SEQUENCE: 107

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 108
<211> LENGTH: 120
<212> TYPE: DNA
```

```
<213> ORGANISM: Artificial Sequence
<220> FEATURE:
<223> OTHER INFORMATION: Synthetic

<400> SEQUENCE: 108
tcaaagcgga gtaggttgtt gcattccgat tacatgaata tgactcctcg ccggcctggg    60
ccgacaagaa aacattacca accctatgcc cccccacgag acttcgctgc gtacaggtcc   120

<210> SEQ ID NO 109
<211> LENGTH: 40
<212> TYPE: PRT
<213> ORGANISM: Artificial Sequence
<220> FEATURE:
<223> OTHER INFORMATION: Synthetic

<400> SEQUENCE: 109
```

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

```
<210> SEQ ID NO 110
<211> LENGTH: 336
<212> TYPE: DNA
<213> ORGANISM: Artificial Sequence
<220> FEATURE:
<223> OTHER INFORMATION: Synthetic

<400> SEQUENCE: 110
cgagtgaagt tttcccgaag cgcagacgct ccggcatatc agcaaggaca gaatcagctg    60
tataacgaac tgaatttggg acgccgcgag gagtatgacg tgcttgataa acgccggggg   120
agagacccgg aaatgggggg taaaccccga gaaagaatc cccaagaagg actctacaat   180
gaactccaga aggataagat ggcggaggcc tactcagaaa taggtatgaa gggcgaacga   240
cgacggggaa aaggtcacga tggcctctac caagggttga gtacggcaac caaagatacg   300
tacgatgcac tgcatatgca ggccctgcct cccaga                             336

<210> SEQ ID NO 111
<211> LENGTH: 112
<212> TYPE: PRT
<213> ORGANISM: Artificial Sequence
<220> FEATURE:
<223> OTHER INFORMATION: Synthetic

<400> SEQUENCE: 111
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 112
<211> LENGTH: 20
<212> TYPE: RNA
<213> ORGANISM: Artificial Sequence
<220> FEATURE:
<223> OTHER INFORMATION: Synthetic

<400> SEQUENCE: 112
gauuccgcuu ggugaaaacg                                                20

<210> SEQ ID NO 113
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 113
gauuccgcuu ggugaaaacg                                                20

<210> SEQ ID NO 114
<211> LENGTH: 100
<212> TYPE: RNA
<213> ORGANISM: Artificial Sequence
<220> FEATURE:
<223> OTHER INFORMATION: Synthetic

<400> SEQUENCE: 114
gauuccgcuu ggugaaaacg guuuuagagc uagaaauagc aaguuaaaau aaggcuaguc    60
cguuaucaac uugaaaaagu ggcaccgagu cggugcuuuu                         100

<210> SEQ ID NO 115
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 115
gauuccgcuu ggugaaaacg guuuuagagc uagaaauagc aaguuaaaau aaggcuaguc    60
cguuaucaac uugaaaaagu ggcaccgagu cggugcuuuu                         100

<210> SEQ ID NO 116
<211> LENGTH: 20
<212> TYPE: RNA
<213> ORGANISM: Artificial Sequence
<220> FEATURE:
<223> OTHER INFORMATION: Synthetic

<400> SEQUENCE: 116
caggacucac acgacuauuc                                                20

```
<210> SEQ ID NO 117
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 117
caggacucac acgacuauuc                                               20

<210> SEQ ID NO 118
<211> LENGTH: 100
<212> TYPE: RNA
<213> ORGANISM: Artificial Sequence
<220> FEATURE:
<223> OTHER INFORMATION: Synthetic

<400> SEQUENCE: 118
caggacucac acgacuauuc guuuuagagc uagaaauagc aaguuaaaau aaggcuaguc    60
cguuaucaac uugaaaaagu ggcaccgagu cggugcuuuu                        100

<210> SEQ ID NO 119
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 119
caggacucac acgacuauuc guuuuagagc uagaaauagc aaguuaaaau aaggcuaguc    60
cguuaucaac uugaaaaagu ggcaccgagu cggugcuuuu                        100

<210> SEQ ID NO 120
<211> LENGTH: 20
<212> TYPE: RNA
<213> ORGANISM: Artificial Sequence
<220> FEATURE:
<223> OTHER INFORMATION: Synthetic

<400> SEQUENCE: 120
uuccgcuugg ugaaaacgag                                               20

<210> SEQ ID NO 121
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate
```

```
<400> SEQUENCE: 121
uuccgcuugg ugaaaacgag                                              20

<210> SEQ ID NO 122
<211> LENGTH: 100
<212> TYPE: RNA
<213> ORGANISM: Artificial Sequence
<220> FEATURE:
<223> OTHER INFORMATION: Synthetic

<400> SEQUENCE: 122
uuccgcuugg ugaaaacgag guuuuagagc uagaaauagc aaguuaaaau aaggcuaguc   60
cguuaucaac uugaaaaagu ggcaccgagu cggugcuuuu                        100

<210> SEQ ID NO 123
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 123
uuccgcuugg ugaaaacgag guuuuagagc uagaaauagc aaguuaaaau aaggcuaguc   60
cguuaucaac uugaaaaagu ggcaccgagu cggugcuuuu                        100

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
cattaggacc tgctcctaga                                              20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
gggatgtcct attgctaagt                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
agggatgtcc tattgctaag                                              20

<210> SEQ ID NO 127
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 127
acggcacgct caccaatcgc                                               20

<210> SEQ ID NO 128
<211> LENGTH: 23
<212> TYPE: DNA
<213> ORGANISM: Artificial Sequence
<220> FEATURE:
<223> OTHER INFORMATION: Synthetic

<400> SEQUENCE: 128
gattccgctt ggtgaaaacg agg                                           23

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
gattccgctt ggtgaaaacg                                               20

<210> SEQ ID NO 130
<211> LENGTH: 23
<212> TYPE: DNA
<213> ORGANISM: Artificial Sequence
<220> FEATURE:
<223> OTHER INFORMATION: Synthetic

<400> SEQUENCE: 130
caggactcac acgactattc tgg                                           23

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
caggactcac acgactattc                                               20

<210> SEQ ID NO 132
<211> LENGTH: 23
<212> TYPE: DNA
<213> ORGANISM: Artificial Sequence
<220> FEATURE:
<223> OTHER INFORMATION: Synthetic

<400> SEQUENCE: 132
ttccgcttgg tgaaaacgag ggg                                           23

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
```
ttccgcttgg tgaaaacgag                    20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
tcaccaagcc cgcgaccaat                    20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
atcaccaagc ccgcgaccaa                    20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
cggtgcggcg caggccctat                    20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
gctttggtcc cattggtcgc                    20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gcccgcagga cgcacccata                    20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
gtgcatccag cgcttcgcac                    20

<210> SEQ ID NO 140
<211> LENGTH: 20
<212> TYPE: DNA

```
<213> ORGANISM: Artificial Sequence
<220> FEATURE:
<223> OTHER INFORMATION: Synthetic

<400> SEQUENCE: 140
cagctacgta tccatcgtga                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
gtgactgaca tcaactccaa                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
cacttgggca ttaacacttt                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ttggaaggcc tgcatcatga                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
ctagggactg cacagtcaat                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
actgcgtgcc ctgccaagaa                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
agagcaacag tgctgtggcc                                              20
```

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
gctactctct ctttctggcc                                                    20

<210> SEQ ID NO 148
<211> LENGTH: 506
<212> TYPE: PRT
<213> ORGANISM: Artificial Sequence
<220> FEATURE:
<223> OTHER INFORMATION: Synthetic

<400> SEQUENCE: 148

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

-continued

```
Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
            325                 330                 335

Gly Val Leu Leu Leu Ser Leu Val Ile Thr Leu Tyr Cys Asn His Arg
        340                 345                 350

Asn Arg Ser Lys Arg Ser Arg Leu Leu His Ser Asp Tyr Met Asn Met
    355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
            405                 410                 415

Glu Leu Asn Leu Gly Arg Arg Glu Glu Tyr Asp Val Leu Asp Lys Arg
        420                 425                 430

Arg Gly Arg Asp Pro Glu Met Gly Gly Lys Pro Arg Arg Lys Asn Pro
    435                 440                 445

Gln Glu Gly Leu Tyr Asn Glu Leu Gln Lys Asp Lys Met Ala Glu Ala
450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
            485                 490                 495

Ala Leu His Met Gln Ala Leu Pro Pro Arg
            500                 505

<210> SEQ ID NO 149
<211> LENGTH: 508
<212> TYPE: PRT
<213> ORGANISM: Artificial Sequence
<220> FEATURE:
<223> OTHER INFORMATION: Synthetic

<400> SEQUENCE: 149

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Leu
            20                  25                  30

Lys Lys Pro Gly Ala Ser Val Lys Val Ser Cys Lys Ala Ser Gly Asn
        35                  40                  45

Thr Leu Thr Asn Tyr Val Ile His Trp Val Arg Gln Ala Pro Gly Gln
    50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
            85                  90                  95

Ala Ser Thr Ala Tyr Met Glu Leu Ser Ser Leu Arg Ser Glu Asp Thr
            100                 105                 110

Ala Val Tyr Tyr Cys Thr Arg Trp Asp Trp Asp Gly Phe Phe Asp Pro
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Glu Ile Val Met Thr Gln
145                 150                 155                 160
```

Ser Pro Ala Thr Leu Ser Val Ser Pro Gly Glu Arg Ala Ser Ile Ser
            165                 170                 175

Cys Arg Ala Ser Gln Ser Leu Val His Ser Asn Gly Asn Thr His Leu
            180                 185                 190

His Trp Tyr Gln Gln Arg Pro Gly Gln Ala Pro Arg Leu Leu Ile Tyr
            195                 200                 205

Ser Val Ser Asn Arg Phe Ser Glu Val Pro Ala Arg Phe Ser Gly Ser
        210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr Ser His Ile Pro Tyr Thr
            245                 250                 255

Phe Gly Gly Gly Thr Lys Leu Glu Ile Lys Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
            325                 330                 335

Gly Val Leu Leu Leu Ser Leu Val Ile Thr Leu Tyr Cys Asn His Arg
            340                 345                 350

Asn Arg Lys Arg Gly Arg Lys Lys Leu Leu Tyr Ile Phe Lys Gln Pro
            355                 360                 365

Phe Met Arg Pro Val Gln Thr Thr Gln Glu Glu Asp Gly Cys Ser Cys
        370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
            405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
            485                 490                 495

Tyr Asp Ala Leu His Met Gln Ala Leu Pro Pro Arg
            500                 505

<210> SEQ ID NO 150
<211> LENGTH: 508
<212> TYPE: PRT
<213> ORGANISM: Artificial Sequence
<220> FEATURE:
<223> OTHER INFORMATION: Synthetic

<400> SEQUENCE: 150

Met Ala Leu Pro Val Thr Ala Leu Leu Leu Pro Leu Ala Leu Leu Leu
1               5                   10                  15

-continued

His Ala Ala Arg Pro Gln Val Gln Leu Val Gln Ser Gly Ala Glu Val
                20              25              30

Lys Lys Pro Gly Ala Ser Val Lys Val Ser Cys Lys Ala Ser Gly Tyr
            35              40              45

Thr Phe Thr Asn Tyr Gly Met Asn Trp Val Arg Gln Ala Pro Gly Gln
        50              55              60

Gly Leu Lys Trp Met Gly Trp Ile Asn Thr Tyr Thr Gly Glu Pro Thr
65              70              75              80

Tyr Ala Asp Ala Phe Lys Gly Arg Val Thr Met Thr Arg Asp Thr Ser
                85              90              95

Ile Ser Thr Ala Tyr Met Glu Leu Ser Arg Leu Arg Ser Asp Asp Thr
                100             105             110

Ala Val Tyr Tyr Cys Ala Arg Asp Tyr Gly Asp Tyr Gly Met Asp Tyr
            115             120             125

Trp Gly Gln Gly Thr Thr Val Thr Val Ser Ser Gly Gly Gly Gly Ser
        130             135             140

Gly Gly Gly Gly Ser Gly Gly Gly Ser Gly Asp Ile Val Met Thr
145             150             155             160

Gln Ser Pro Asp Ser Leu Ala Val Ser Leu Gly Glu Arg Ala Thr Ile
                165             170             175

Asn Cys Arg Ala Ser Lys Ser Val Ser Thr Ser Gly Tyr Ser Phe Met
                180             185             190

His Trp Tyr Gln Gln Lys Pro Gly Gln Pro Pro Lys Leu Leu Ile Tyr
            195             200             205

Leu Ala Ser Asn Leu Glu Ser Gly Val Pro Asp Arg Phe Ser Gly Ser
        210             215             220

Gly Ser Gly Thr Asp Phe Thr Leu Thr Ile Ser Ser Leu Gln Ala Glu
225             230             235             240

Asp Val Ala Val Tyr Tyr Cys Gln His Ser Arg Glu Val Pro Trp Thr
                245             250             255

Phe Gly Gln Gly Thr Lys Val Glu Ile Lys Ser Ala Ala Ala Phe Val
                260             265             270

Pro Val Phe Leu Pro Ala Lys Pro Thr Thr Thr Pro Ala Pro Arg Pro
            275             280             285

Pro Thr Pro Ala Pro Thr Ile Ala Ser Gln Pro Leu Ser Leu Arg Pro
        290             295             300

Glu Ala Cys Arg Pro Ala Ala Gly Gly Ala Val His Thr Arg Gly Leu
305             310             315             320

Asp Phe Ala Cys Asp Ile Tyr Ile Trp Ala Pro Leu Ala Gly Thr Cys
                325             330             335

Gly Val Leu Leu Leu Ser Leu Val Ile Thr Leu Tyr Cys Asn His Arg
                340             345             350

Asn Arg Lys Arg Gly Arg Lys Lys Leu Leu Tyr Ile Phe Lys Gln Pro
            355             360             365

Phe Met Arg Pro Val Gln Thr Thr Gln Glu Glu Asp Gly Cys Ser Cys
        370             375             380

Arg Phe Pro Glu Glu Glu Glu Gly Gly Cys Glu Leu Arg Val Lys Phe
385             390             395             400

Ser Arg Ser Ala Asp Ala Pro Ala Tyr Gln Gln Gly Gln Asn Gln Leu
                405             410             415

Tyr Asn Glu Leu Asn Leu Gly Arg Arg Glu Glu Tyr Asp Val Leu Asp
                420             425             430

```
Lys Arg Arg Gly Arg Asp Pro Glu Met Gly Gly Lys Pro Arg Arg Lys
            435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505
```

<210> SEQ ID NO 151
<211> LENGTH: 26
<212> TYPE: DNA
<213> ORGANISM: Artificial Sequence
<220> FEATURE:
<223> OTHER INFORMATION: Synthetic

<400> SEQUENCE: 151
ggcaccatat tcattttgca ggtgaa                                    26

<210> SEQ ID NO 152
<211> LENGTH: 25
<212> TYPE: DNA
<213> ORGANISM: Artificial Sequence
<220> FEATURE:
<223> OTHER INFORMATION: Synthetic

<400> SEQUENCE: 152
atgtgcgctc tgcccactga cgggc                                     25

<210> SEQ ID NO 153
<211> LENGTH: 29
<212> TYPE: DNA
<213> ORGANISM: Artificial Sequence
<220> FEATURE:
<223> OTHER INFORMATION: Synthetic

<400> SEQUENCE: 153
agacatgagg tctatggact tcaggctcc                                 29

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
cttggtgaaa acgagggggcc                                          20

<210> SEQ ID NO 155
<211> LENGTH: 19
<212> TYPE: DNA
<213> ORGANISM: Artificial Sequence
<220> FEATURE:
<223> OTHER INFORMATION: Synthetic

<400> SEQUENCE: 155
cttggtgaaa cgaggggcc                                            19

<210> SEQ ID NO 156
<211> LENGTH: 21
<212> TYPE: DNA

```
<213> ORGANISM: Artificial Sequence
<220> FEATURE:
<223> OTHER INFORMATION: Synthetic

<400> SEQUENCE: 156
cttggtgaaa aacgaggggc c                                              21

<210> SEQ ID NO 157
<211> LENGTH: 18
<212> TYPE: DNA
<213> ORGANISM: Artificial Sequence
<220> FEATURE:
<223> OTHER INFORMATION: Synthetic

<400> SEQUENCE: 157
cttggtgaac gagggggcc                                                 18

<210> SEQ ID NO 158
<211> LENGTH: 14
<212> TYPE: DNA
<213> ORGANISM: Artificial Sequence
<220> FEATURE:
<223> OTHER INFORMATION: Synthetic

<400> SEQUENCE: 158
cttggtgagg ggcc                                                      14

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
cacacgacta ttctggcttc                                                20

<210> SEQ ID NO 160
<211> LENGTH: 15
<212> TYPE: DNA
<213> ORGANISM: Artificial Sequence
<220> FEATURE:
<223> OTHER INFORMATION: Synthetic

<400> SEQUENCE: 160
cacacgactg gcttc                                                     15

<210> SEQ ID NO 161
<211> LENGTH: 11
<212> TYPE: DNA
<213> ORGANISM: Artificial Sequence
<220> FEATURE:
<223> OTHER INFORMATION: Synthetic

<400> SEQUENCE: 161
cacacgactt c                                                         11

<210> SEQ ID NO 162
<211> LENGTH: 18
<212> TYPE: DNA
<213> ORGANISM: Artificial Sequence
<220> FEATURE:
<223> OTHER INFORMATION: Synthetic

<400> SEQUENCE: 162
cacacgactt ctggcttc                                                  18
```

<210> SEQ ID NO 163
<211> LENGTH: 19
<212> TYPE: DNA
<213> ORGANISM: Artificial Sequence
<220> FEATURE:
<223> OTHER INFORMATION: Synthetic

<400> SEQUENCE: 163
cacacgacta tctggcttc                                                  19

<210> SEQ ID NO 164
<211> LENGTH: 21
<212> TYPE: DNA
<213> ORGANISM: Artificial Sequence
<220> FEATURE:
<223> OTHER INFORMATION: Synthetic

<400> SEQUENCE: 164
cacacgacta attctggctt c                                               21

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
cacacgacta tttctggctt c                                               21

<210> SEQ ID NO 166
<211> LENGTH: 19
<212> TYPE: DNA
<213> ORGANISM: Artificial Sequence
<220> FEATURE:
<223> OTHER INFORMATION: Synthetic

<400> SEQUENCE: 166
cacacgactt tctggcttc                                                  19

<210> SEQ ID NO 167
<211> LENGTH: 16
<212> TYPE: DNA
<213> ORGANISM: Artificial Sequence
<220> FEATURE:
<223> OTHER INFORMATION: Synthetic

<400> SEQUENCE: 167
cacacgttct ggcttc                                                     16

<210> SEQ ID NO 168
<211> LENGTH: 12
<212> TYPE: DNA
<213> ORGANISM: Artificial Sequence
<220> FEATURE:
<223> OTHER INFORMATION: Synthetic

<400> SEQUENCE: 168
cacactggct tc                                                         12

<210> SEQ ID NO 169
<211> LENGTH: 18
<212> TYPE: DNA
<213> ORGANISM: Artificial Sequence
<220> FEATURE:

```
<223> OTHER INFORMATION: Synthetic

<400> SEQUENCE: 169
cacacgacta ctggcttc                                                    18

<210> SEQ ID NO 170
<211> LENGTH: 17
<212> TYPE: DNA
<213> ORGANISM: Artificial Sequence
<220> FEATURE:
<223> OTHER INFORMATION: Synthetic

<400> SEQUENCE: 170
cacacgactc tggcttc                                                     17

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tggtgaaaac gagggccctt                                                  20

<210> SEQ ID NO 172
<211> LENGTH: 21
<212> TYPE: DNA
<213> ORGANISM: Artificial Sequence
<220> FEATURE:
<223> OTHER INFORMATION: Synthetic

<400> SEQUENCE: 172
tggtgaaaac cgagggcct t                                                 21

<210> SEQ ID NO 173
<211> LENGTH: 14
<212> TYPE: DNA
<213> ORGANISM: Artificial Sequence
<220> FEATURE:
<223> OTHER INFORMATION: Synthetic

<400> SEQUENCE: 173
tggtgagggg cctt                                                        14

<210> SEQ ID NO 174
<211> LENGTH: 19
<212> TYPE: DNA
<213> ORGANISM: Artificial Sequence
<220> FEATURE:
<223> OTHER INFORMATION: Synthetic

<400> SEQUENCE: 174
tggtgaaacg aggggcctt                                                   19

<210> SEQ ID NO 175
<211> LENGTH: 18
<212> TYPE: DNA
<213> ORGANISM: Artificial Sequence
<220> FEATURE:
<223> OTHER INFORMATION: Synthetic

<400> SEQUENCE: 175
tggtgaacga ggggcctt                                                    18
```

```
<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gctcaccaat cgccggtgtg                                               20

<210> SEQ ID NO 177
<211> LENGTH: 19
<212> TYPE: DNA
<213> ORGANISM: Artificial Sequence
<220> FEATURE:
<223> OTHER INFORMATION: Synthetic

<400> SEQUENCE: 177
gctcaccaac gccggtgtg                                                19

<210> SEQ ID NO 178
<211> LENGTH: 21
<212> TYPE: DNA
<213> ORGANISM: Artificial Sequence
<220> FEATURE:
<223> OTHER INFORMATION: Synthetic

<400> SEQUENCE: 178
gctcaccaat tcgccggtgt g                                             21

<210> SEQ ID NO 179
<211> LENGTH: 18
<212> TYPE: DNA
<213> ORGANISM: Artificial Sequence
<220> FEATURE:
<223> OTHER INFORMATION: Synthetic

<400> SEQUENCE: 179
gctcaccacg ccggtgtg                                                 18

<210> SEQ ID NO 180
<211> LENGTH: 13
<212> TYPE: DNA
<213> ORGANISM: Artificial Sequence
<220> FEATURE:
<223> OTHER INFORMATION: Synthetic

<400> SEQUENCE: 180
gctcaccggt gtg                                                      13

<210> SEQ ID NO 181
<211> LENGTH: 17
<212> TYPE: DNA
<213> ORGANISM: Artificial Sequence
<220> FEATURE:
<223> OTHER INFORMATION: Synthetic

<400> SEQUENCE: 181
gctcacccgc cggtgtg                                                  17

<210> SEQ ID NO 182
<211> LENGTH: 16
<212> TYPE: DNA
<213> ORGANISM: Artificial Sequence
<220> FEATURE:
<223> OTHER INFORMATION: Synthetic
```

```
<400> SEQUENCE: 182
gctcaccgcc ggtgtg                                                    16

<210> SEQ ID NO 183
<211> LENGTH: 21
<212> TYPE: DNA
<213> ORGANISM: Artificial Sequence
<220> FEATURE:
<223> OTHER INFORMATION: Synthetic

<400> SEQUENCE: 183
gctcaccaat acgccggtgt g                                              21

<210> SEQ ID NO 184
<211> LENGTH: 15
<212> TYPE: DNA
<213> ORGANISM: Artificial Sequence
<220> FEATURE:
<223> OTHER INFORMATION: Synthetic

<400> SEQUENCE: 184
gctcacgccg gtgtg                                                     15

<210> SEQ ID NO 185
<211> LENGTH: 21
<212> TYPE: DNA
<213> ORGANISM: Artificial Sequence
<220> FEATURE:
<223> OTHER INFORMATION: Synthetic

<400> SEQUENCE: 185
gctcaccaat gcgccggtgt g                                              21

<210> SEQ ID NO 186
<211> LENGTH: 21
<212> TYPE: DNA
<213> ORGANISM: Artificial Sequence
<220> FEATURE:
<223> OTHER INFORMATION: Synthetic

<400> SEQUENCE: 186
gctcaccaat ccgccggtgt g                                              21

<210> SEQ ID NO 187
<211> LENGTH: 28
<212> TYPE: DNA
<213> ORGANISM: Artificial Sequence
<220> FEATURE:
<223> OTHER INFORMATION: Synthetic

<400> SEQUENCE: 187
gctcaccaat tcaaggcacg ccggtgtg                                       28

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
cctattgcta agtgggtaag                                                20

<210> SEQ ID NO 189
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 189
cctattgcta gtgggtaag                                                    19

<210> SEQ ID NO 190
<211> LENGTH: 21
<212> TYPE: DNA
<213> ORGANISM: Artificial Sequence
<220> FEATURE:
<223> OTHER INFORMATION: Synthetic

<400> SEQUENCE: 190
cctattgcta aagtgggtaa g                                                 21

<210> SEQ ID NO 191
<211> LENGTH: 13
<212> TYPE: DNA
<213> ORGANISM: Artificial Sequence
<220> FEATURE:
<223> OTHER INFORMATION: Synthetic

<400> SEQUENCE: 191
cctattgggt aag                                                          13

<210> SEQ ID NO 192
<211> LENGTH: 18
<212> TYPE: DNA
<213> ORGANISM: Artificial Sequence
<220> FEATURE:
<223> OTHER INFORMATION: Synthetic

<400> SEQUENCE: 192
cctattgcag tgggtaag                                                     18

<210> SEQ ID NO 193
<211> LENGTH: 11
<212> TYPE: DNA
<213> ORGANISM: Artificial Sequence
<220> FEATURE:
<223> OTHER INFORMATION: Synthetic

<400> SEQUENCE: 193
cagtgggtaa g                                                            11

<210> SEQ ID NO 194
<211> LENGTH: 12
<212> TYPE: DNA
<213> ORGANISM: Artificial Sequence
<220> FEATURE:
<223> OTHER INFORMATION: Synthetic

<400> SEQUENCE: 194
cctattgcta ag                                                           12

<210> SEQ ID NO 195
<211> LENGTH: 21
<212> TYPE: DNA
<213> ORGANISM: Artificial Sequence
<220> FEATURE:
<223> OTHER INFORMATION: Synthetic

<400> SEQUENCE: 195
```
cctattgcta tagtgggtaa g                                            21

<210> SEQ ID NO 196
<211> LENGTH: 17
<212> TYPE: DNA
<213> ORGANISM: Artificial Sequence
<220> FEATURE:
<223> OTHER INFORMATION: Synthetic

<400> SEQUENCE: 196
cctattgagt gggtaag                                                 17

<210> SEQ ID NO 197
<211> LENGTH: 12
<212> TYPE: DNA
<213> ORGANISM: Artificial Sequence
<220> FEATURE:
<223> OTHER INFORMATION: Synthetic

<400> SEQUENCE: 197
ccagtgggta ag                                                      12

<210> SEQ ID NO 198
<211> LENGTH: 15
<212> TYPE: DNA
<213> ORGANISM: Artificial Sequence
<220> FEATURE:
<223> OTHER INFORMATION: Synthetic

<400> SEQUENCE: 198
cctattgtgg gtaag                                                   15

<210> SEQ ID NO 199
<211> LENGTH: 13
<212> TYPE: DNA
<213> ORGANISM: Artificial Sequence
<220> FEATURE:
<223> OTHER INFORMATION: Synthetic

<400> SEQUENCE: 199
cctagtgggt aag                                                     13

<210> SEQ ID NO 200
<211> LENGTH: 15
<212> TYPE: DNA
<213> ORGANISM: Artificial Sequence
<220> FEATURE:
<223> OTHER INFORMATION: Synthetic

<400> SEQUENCE: 200
cctatagtgg gtaag                                                   15

<210> SEQ ID NO 201
<211> LENGTH: 18
<212> TYPE: DNA
<213> ORGANISM: Artificial Sequence
<220> FEATURE:
<223> OTHER INFORMATION: Synthetic

<400> SEQUENCE: 201
cctattgcta tgggtaag                                                18

<210> SEQ ID NO 202
<211> LENGTH: 21
<212> TYPE: DNA
<213> ORGANISM: Artificial Sequence

```
<220> FEATURE:
<223> OTHER INFORMATION: Synthetic

<400> SEQUENCE: 202
cctattgcta cagtgggtaa g                                              21

<210> SEQ ID NO 203
<211> LENGTH: 14
<212> TYPE: DNA
<213> ORGANISM: Artificial Sequence
<220> FEATURE:
<223> OTHER INFORMATION: Synthetic

<400> SEQUENCE: 203
cctattgcta taag                                                      14

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
tcctattgct aagtgggtaa                                                20

<210> SEQ ID NO 205
<211> LENGTH: 21
<212> TYPE: DNA
<213> ORGANISM: Artificial Sequence
<220> FEATURE:
<223> OTHER INFORMATION: Synthetic

<400> SEQUENCE: 205
tcctattgct taagtgggta a                                              21

<210> SEQ ID NO 206
<211> LENGTH: 17
<212> TYPE: DNA
<213> ORGANISM: Artificial Sequence
<220> FEATURE:
<223> OTHER INFORMATION: Synthetic

<400> SEQUENCE: 206
tcctattaag tgggtaa                                                   17

<210> SEQ ID NO 207
<211> LENGTH: 19
<212> TYPE: DNA
<213> ORGANISM: Artificial Sequence
<220> FEATURE:
<223> OTHER INFORMATION: Synthetic

<400> SEQUENCE: 207
tcctattgca agtgggtaa                                                 19

<210> SEQ ID NO 208
<211> LENGTH: 19
<212> TYPE: DNA
<213> ORGANISM: Artificial Sequence
<220> FEATURE:
<223> OTHER INFORMATION: Synthetic

<400> SEQUENCE: 208
tcctattgta agtgggtaa                                                 19
```

<210> SEQ ID NO 209
<211> LENGTH: 13
<212> TYPE: DNA
<213> ORGANISM: Artificial Sequence
<220> FEATURE:
<223> OTHER INFORMATION: Synthetic

<400> SEQUENCE: 209
tcctattggg taa                                                    13

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
acctgctcct agatgggtat                                             20

<210> SEQ ID NO 211
<211> LENGTH: 21
<212> TYPE: DNA
<213> ORGANISM: Artificial Sequence
<220> FEATURE:
<223> OTHER INFORMATION: Synthetic

<400> SEQUENCE: 211
acctgctcct tagatgggta t                                           21

<210> SEQ ID NO 212
<211> LENGTH: 19
<212> TYPE: DNA
<213> ORGANISM: Artificial Sequence
<220> FEATURE:
<223> OTHER INFORMATION: Synthetic

<400> SEQUENCE: 212
acctgctcca gatgggtat                                              19

<210> SEQ ID NO 213
<211> LENGTH: 17
<212> TYPE: DNA
<213> ORGANISM: Artificial Sequence
<220> FEATURE:
<223> OTHER INFORMATION: Synthetic

<400> SEQUENCE: 213
acctgctaga tgggtat                                                17

<210> SEQ ID NO 214
<211> LENGTH: 19
<212> TYPE: DNA
<213> ORGANISM: Artificial Sequence
<220> FEATURE:
<223> OTHER INFORMATION: Synthetic

<400> SEQUENCE: 214
acctgctcta gatgggtat                                              19

<210> SEQ ID NO 215
<211> LENGTH: 16
<212> TYPE: DNA
<213> ORGANISM: Artificial Sequence
<220> FEATURE:
<223> OTHER INFORMATION: Synthetic

```
<400> SEQUENCE: 215
acctgtagat gggtat                                                   16

<210> SEQ ID NO 216
<211> LENGTH: 18
<212> TYPE: DNA
<213> ORGANISM: Artificial Sequence
<220> FEATURE:
<223> OTHER INFORMATION: Synthetic

<400> SEQUENCE: 216
acctgctcct atgggtat                                                 18

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
gcattaacac ttttggacga                                               20

<210> SEQ ID NO 218
<211> LENGTH: 21
<212> TYPE: DNA
<213> ORGANISM: Artificial Sequence
<220> FEATURE:
<223> OTHER INFORMATION: Synthetic

<400> SEQUENCE: 218
gcattaacac tttttggacg a                                             21

<210> SEQ ID NO 219
<211> LENGTH: 22
<212> TYPE: DNA
<213> ORGANISM: Artificial Sequence
<220> FEATURE:
<223> OTHER INFORMATION: Synthetic

<400> SEQUENCE: 219
gcattaacac ttttttggac ga                                            22

<210> SEQ ID NO 220
<211> LENGTH: 19
<212> TYPE: DNA
<213> ORGANISM: Artificial Sequence
<220> FEATURE:
<223> OTHER INFORMATION: Synthetic

<400> SEQUENCE: 220
gcattaacat tttggacga                                                19

<210> SEQ ID NO 221
<211> LENGTH: 19
<212> TYPE: DNA
<213> ORGANISM: Artificial Sequence
<220> FEATURE:
<223> OTHER INFORMATION: Synthetic

<400> SEQUENCE: 221
gcattaacac tttggacga                                                19

<210> SEQ ID NO 222
```

```
<211> LENGTH: 16
<212> TYPE: DNA
<213> ORGANISM: Artificial Sequence
<220> FEATURE:
<223> OTHER INFORMATION: Synthetic

<400> SEQUENCE: 222
gcattatttt ggacga                                                         16

<210> SEQ ID NO 223
<211> LENGTH: 23
<212> TYPE: DNA
<213> ORGANISM: Artificial Sequence
<220> FEATURE:
<223> OTHER INFORMATION: Synthetic

<400> SEQUENCE: 223
gcattaacac tttttttgga cga                                                 23

<210> SEQ ID NO 224
<211> LENGTH: 18
<212> TYPE: DNA
<213> ORGANISM: Artificial Sequence
<220> FEATURE:
<223> OTHER INFORMATION: Synthetic

<400> SEQUENCE: 224
gcattaactt ttggacga                                                       18

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
ctgcacagtc aatggggatg                                                     20

<210> SEQ ID NO 226
<211> LENGTH: 21
<212> TYPE: DNA
<213> ORGANISM: Artificial Sequence
<220> FEATURE:
<223> OTHER INFORMATION: Synthetic

<400> SEQUENCE: 226
ctgcacagtc aaatggggat g                                                   21

<210> SEQ ID NO 227
<211> LENGTH: 21
<212> TYPE: DNA
<213> ORGANISM: Artificial Sequence
<220> FEATURE:
<223> OTHER INFORMATION: Synthetic

<400> SEQUENCE: 227
ctgcacagtc caatggggat g                                                   21

<210> SEQ ID NO 228
<211> LENGTH: 16
<212> TYPE: DNA
<213> ORGANISM: Artificial Sequence
<220> FEATURE:
<223> OTHER INFORMATION: Synthetic

<400> SEQUENCE: 228
```

```
ctgcacaatg gggatg                                              16
```

<210> SEQ ID NO 229
<211> LENGTH: 19
<212> TYPE: DNA
<213> ORGANISM: Artificial Sequence
<220> FEATURE:
<223> OTHER INFORMATION: Synthetic

<400> SEQUENCE: 229

```
ctgcacagtc atggggatg                                           19
```

<210> SEQ ID NO 230
<211> LENGTH: 19
<212> TYPE: DNA
<213> ORGANISM: Artificial Sequence
<220> FEATURE:
<223> OTHER INFORMATION: Synthetic

<400> SEQUENCE: 230

```
ctgcacagta atggggatg                                           19
```

<210> SEQ ID NO 231
<211> LENGTH: 17
<212> TYPE: DNA
<213> ORGANISM: Artificial Sequence
<220> FEATURE:
<223> OTHER INFORMATION: Synthetic

<400> SEQUENCE: 231

```
ctgcacaaat ggggatg                                             17
```

<210> SEQ ID NO 232
<211> LENGTH: 14
<212> TYPE: DNA
<213> ORGANISM: Artificial Sequence
<220> FEATURE:
<223> OTHER INFORMATION: Synthetic

<400> SEQUENCE: 232

```
ctgcaatggg gatg                                                14
```

<210> SEQ ID NO 233
<211> LENGTH: 18
<212> TYPE: DNA
<213> ORGANISM: Artificial Sequence
<220> FEATURE:
<223> OTHER INFORMATION: Synthetic

<400> SEQUENCE: 233

```
ctgcacagaa tggggatg                                            18
```

<210> SEQ ID NO 234
<211> LENGTH: 18
<212> TYPE: DNA
<213> ORGANISM: Artificial Sequence
<220> FEATURE:
<223> OTHER INFORMATION: Synthetic

<400> SEQUENCE: 234

```
ctgcacagtc tggggatg                                            18
```

<210> SEQ ID NO 235
<211> LENGTH: 10
<212> TYPE: DNA

```
<213> ORGANISM: Artificial Sequence
<220> FEATURE:
<223> OTHER INFORMATION: Synthetic

<400> SEQUENCE: 235
ctgcacagtc                                                            10

<210> SEQ ID NO 236
<211> LENGTH: 10
<212> TYPE: DNA
<213> ORGANISM: Artificial Sequence
<220> FEATURE:
<223> OTHER INFORMATION: Synthetic

<400> SEQUENCE: 236
aatggggatg                                                            10

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
gccctgccaa gagggaagg                                                  20

<210> SEQ ID NO 238
<211> LENGTH: 21
<212> TYPE: DNA
<213> ORGANISM: Artificial Sequence
<220> FEATURE:
<223> OTHER INFORMATION: Synthetic

<400> SEQUENCE: 238
gccctgccaa agaagggaag g                                               21

<210> SEQ ID NO 239
<211> LENGTH: 19
<212> TYPE: DNA
<213> ORGANISM: Artificial Sequence
<220> FEATURE:
<223> OTHER INFORMATION: Synthetic

<400> SEQUENCE: 239
gccctgccag aagggaagg                                                  19

<210> SEQ ID NO 240
<211> LENGTH: 22
<212> TYPE: DNA
<213> ORGANISM: Artificial Sequence
<220> FEATURE:
<223> OTHER INFORMATION: Synthetic

<400> SEQUENCE: 240
gccctgccaa aagaagggaa gg                                              22
```

```
<210> SEQ ID NO 241
<211> LENGTH: 16
<212> TYPE: DNA
<213> ORGANISM: Artificial Sequence
<220> FEATURE:
<223> OTHER INFORMATION: Synthetic

<400> SEQUENCE: 241
gccctagaag ggaagg                                                 16
```

GENETICALLY ENGINEERED T CELLS HAVING IMPROVED PERSISTENCE IN CULTURE

CROSS-REFERENCE TO RELATED APPLICATIONS

This application claims the benefit of priority to U.S. Provisional Patent Application No. 62/897,016, filed Sep. 6, 2019, U.S. Provisional Patent Application No. 62/927,764, filed Oct. 30, 2019, and U.S. Provisional Patent Application No. 63/034,646, filed Jun. 4, 2020. Each of the prior applications is hereby incorporated by reference in its entirety.

SEQUENCE LISTING

The instant application contains a Sequence Listing, which has been filed electronically in ASCII format and is hereby incorporated by reference in its entirety. Said ASCII copy, created on Nov. 2, 2020, is named 095136-0015-001US01-SEQ.txt and is 69,300 bytes in size.

BACKGROUND OF THE INVENTION

Chimeric antigen receptor (CAR) T-cell therapy uses genetically-modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

T cells having improved persistence in culture are desired in CAR-T therapy. Such T cells live longer in both in vitro and in vivo, thereby conferring benefits in CAR-T cell manufacturing and clinical applications. However, it remains challenging to improve persistence of T cells in culture.

SUMMARY OF THE INVENTION

The present disclosure is based, at least in part, on the development of a T cell bank comprising T cells with genetic editing of certain genes (e.g., genes involved in cell self-renewal such as TET2, apoptosis such as FAS, T cell exhaustion or replicative senescence such as CD70, or a combination thereof) to improve T cell persistence in cell culture. The genetically edited T cells disclosed herein showed enhanced cell expansion and proliferation capacity in culture, reduced apoptosis (e.g., induced by FAS ligand), enhanced frequency of activation (e.g., enhanced cytotoxicity), and enhanced CAR-T efficacy in animal models (via, e.g., longer persistence). For example, CAR-T cells having a disrupted TET2 gene showed both growth advantage and CAR-T enrichment effects in vitro and allows CAR-T cells to persist longer in animal models having both liquid and solid tumors. Further, the genetically edited T cells having a disrupted TET2 gene showed cytokine-dependent growth, indicating safety. Such a T cell bank (e.g., having a disrupted TET2 gene) can be used for making therapeutic T cells, for example, CAR-T cells.

Accordingly, one aspect of the present disclosure provides a population of genetically engineered T cells (a T cell bank), comprising: (i) a mutated gene involved in cell self-renewal; (ii) a disrupted gene involved in apoptosis; (iii) a disrupted gene involved in regulation of T cell exhaustion or replicative senescence; or (iv) a combination of any one of (i)-(iii). The population of genetically engineered T cells, as compared to the non-engineered T counterparts, has one or more of the following superior features: (a) enhanced expansion capacity in culture, (b) enhanced proliferation capacity, (c) a reduced apoptosis level, and (d) an enhanced frequency of activation. The T cell bank as disclosed herein may be derived from primary T cells of one or more donors, for example, one or more human donors.

In some embodiments, genes involved in cell self-renewal may comprise the TET2 gene. A mutated TET2 gene may be a disrupted TET2 gene, which does not express a functional TET2 protein. Alternatively, a mutated TET2 gene may be a modulated TET2 gene that expresses a truncated version of TET2 (e.g., a truncated version having a molecular weight of around 170 kDa). Any of the mutated TET2 genes may be genetically edited by CRISPR/Cas mediated gene editing, for example, using a guide RNA (gRNA) targeting a desired site in the TET2 gene (either coding region or non-coding region). In some examples, the mutated TET2 gene may have one or more genetic editing events in one or more of exon 1, exon 3, exon 4, exon 5 and exon 6. In particular examples, the mutated TET2 gene is genetically edited using a gRNA comprising SEQ ID NO: 14, 18, 22, 26, 112, 116, or 120.

In some embodiments, genes involved in apoptosis may comprise FAS, and/or genes involved in T cell exhaustion may comprise CD70. Such genes may be disrupted, for example, via CRISPR/Cas-mediated gene editing. Exemplary gRNAs targeting FAS may comprise SEQ ID NO: 69, 73, 77, 81, or 85. Exemplary gRNAs targeting CD70 may comprise SEQ ID NO: 34, 38, 42, 46, 50, 54, or 58.

In some embodiments, the population of genetically engineered T cells described herein may comprise a combination at least one mutated gene involved in cell self-renewal (e.g., TET2), at least one gene involved in apoptosis (e.g., FAS), and/or at least one gene involved in T cell exhaustion (e.g., CD70).

Any of the population of genetically engineered T cells as disclosed herein may further comprise a disrupted beta-2-microglobulin (β2M) gene, a disrupted T cell receptor alpha chain constant region (TRAC) gene, or a combination thereof. In some embodiments, the T cells may be further engineered to express a chimeric antigen receptor (CAR), for example, comprising a nucleic acid encoding the CAR. In some examples, the nucleic acid is inserted in the genome of the T cells. In specific examples, the genetically engineered T cells may have a disrupted TRAC gene, in which a nucleotide acid encoding a chimeric antigen receptor may be inserted. In some embodiments, the CAR may target a tumor antigen. Examples include CD19, B cell maturation antigen (BCMA), or CD70.

In another aspect, the present disclosure provides a method for preparing T cell bank as disclosed herein. Such a method may comprise (a) providing a plurality of cells, which are T cells or precursor cells thereof; (b) genetically editing at least one gene involved in cell self-renewal (e.g., TET2), at least one gene involved in apoptosis (e.g., FAS), and/or at least one gene involved in regulation of T cell exhaustion (e.g., CD70); and (c) producing the population of genetically engineered T cells.

In some embodiments, the T cells of step (a) may be derived from one or more suitable donors, for example, one or more human donors. In some embodiments, the T cells show cytokine-dependent growth.

In some embodiments, step (b) can be performed by delivering to the cells of (a) one or more RNA-guided nucleases, and one or more gRNAs specific to the one or more target genes disclosed herein. In some examples, the RNA-guided nuclease can be a Cas9 nuclease, for example, a S. pyogenes Cas9 nuclease. In some examples, the RNA-guided nuclease and the one or more gRNAs can be complexed in a ribonucleoprotein particle (RNP). Step (b) may be performed by a single electroporation event. Alternatively, step (b) may be performed by two sequential electroporation events.

In some embodiments, the target gene comprises TET2. Exemplary gRNA targeting TET2 may be specific to exon 1, exon 3, exon 4, exon 5, and/or exon 6 of the TET2 gene. Such gRNAs may comprise the nucleotide sequence of SEQ ID NO: 14, 18, 22, or 26. Alternatively or in addition, the target genes may comprise FAS and/or CD70. Exemplary gRNAs targeting FAS may comprise the nucleotide sequence of SEQ ID NO: 69, 73, 77, 81, or 85. Exemplary gRNAs targeting CD70 may comprise the nucleotide sequence of SEQ ID NO: 34, 38, 42, 46, 50, 54, or 58.

In yet another aspect, the present disclosure provides a method for preparing genetically engineered T cells expressing a chimeric antigen receptor (CAR) using genetically engineered T cells from any of the T cell banks disclosed herein. Such a method may comprise: (a) providing a plurality of T cells from a T cell bank, which may comprise genetically engineered T cells having at least one gene involved in cell self-renewal (e.g., TET2), at least one gene involved in apoptosis (e.g., FAS), and/or at least one gene involved in regulation of T cell exhaustion (e.g., CD70); (b) delivering to the plurality of the T cells a nucleic acid encoding a CAR; and (c) producing genetically engineered T cells expressing the CAR.

In some embodiments, the plurality of T cells from the T cell bank further comprises a disrupted β2M gene. In other embodiments, the method may further comprise genetically editing a β2M gene, for example, delivering to the plurality of the T cells a gRNA targeting a β2M gene.

In some embodiments, the plurality of T cells from the T cell bank further comprises a disrupted TRAC gene. In other embodiments, the method may further comprise genetically editing a TRAC gene, for example, delivering to the plurality of the T cells a gRNA targeting a TRAC gene.

In any of the methods disclosed herein, a RNA-guided nuclease may be delivered to the plurality of the T cells from the T cell bank. In some examples, the RNA-guided nuclease can be a Cas9 nuclease, for example, a S. pyo genes Cas9 nuclease. In some examples, the RNA-guided nuclease and the gRNA(s) can be complexed in a ribonucleoprotein particle (RNP).

The genetically edited T cells prepared by any of the preparation methods disclosed herein are also within the scope of the present disclosure.

Any of the CAR-T cells disclosed herein may be used for therapeutic purposes (e.g., eliminating disease cells targeted by the CAR polypeptide on the CAR-T cells) at a dose lower than a standard dose of CAR-T therapy, which refers to the dose of CAR-T cells expressing the same CAR polypeptide and lacking the generic edits for enhancing T cell persistence as disclosed herein (e.g., with no genetic edits to TET2, FAS, and/or CD70).

Also within the scope of the present disclosures is a guide RNA (gRNA) targeting a TET2 gene. In some embodiments, the gRNA comprises a nucleotide sequence specific to exon exon 5 of the TET2 gene. In some examples, a TET2 gene edited by the gRNA may express a truncated version of TET2. Such a gRNA may target the site of GGGATGTCC-TATTGCTAAGT (SEQ ID NO: 125) in exon 5 of the TET2 gene. In one example, the gRNA may comprise the nucleotide sequence of SEQ ID NO: 18. Alternatively, the gRNA may target the site of AGGGATGTCCTATTGCTAAG (SEQ ID NO: 126) in exon 5 of the TET2 gene. In one example, the gRNA may comprise the nucleotide sequence of SEQ ID NO: 22.

In other embodiments, the gRNA may comprise a nucleotide sequence targeting exon 3 of the TET2 gene. For example, the gRNA may comprise a nucleotide sequence targeting GATTCCGCTTGGTGAAAACG (SEQ ID NO: 129) in exon 3 of the TET2 gene. Alternatively, the gRNA may comprise a nucleotide sequence targeting CAGGACT-CACACGACTATTC
(SEQ ID NO: 131) in exon 3 of the TET2 gene. In another example, the gRNA may comprise a nucleotide sequence targeting TTCCGCTTGGTGAAAACGAG (SEQ ID NO: 133) in exon 3 of the TET2 gene. Exemplary gRNAs may comprise the nucleotide sequence of SEQ ID NO: 112, 116, or 120.

In some embodiments, the gRNA may comprise a nucleotide sequence targeting exon 4 of the TET2 gene. For example, the gRNA may comprise a nucleotide sequence targeting CATTAGGACCTGCTCCTAGA (SEQ ID NO: 124) in exon 4 of the TET2 gene. In one example, the gRNA may comprise the nucleotide sequence of SEQ ID NO: 14.

In some embodiments, the gRNA may comprise a nucleotide sequence targeting exon 6 of the TET2 gene. For example, the gRNA may comprise a nucleotide sequence targeting ACGGCACGCTCACCAATCGC (SEQ ID NO: 127) in exon 6 of the TET2 gene. In one example, the gRNA may comprise the nucleotide sequence of SEQ ID NO: 26.

Any of the gRNAs disclosed herein may further comprise a scaffold sequence. In some instances, the gRNA may comprise one or more modified nucleotides, for example, one or more 2'-O-methyl phosphorothioate residues at the 5' and/or 3' terminus of the gRNA. Exemplary gRNAs targeting TET2 are provided in Table 3 (including unmodified sequences and modified sequences), all of which are within the scope of the present disclosure and can be used in any of the methods disclosed herein for genetic editing of the TET2 genes in a host cell such as a T cell.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1A: a picture showing presence of TET2 proteins in primary human T cells edited by gRNAs target exon 5 of the TET2 gene as determined by a Western Blot assay. No protein was detected in cells transfected with one of the gRNAs including TET2 exon 5_T1, and TET2 exon 5_T2. TET2 exon 5_T1 gRNA produced a truncated form of the TET2 protein. FIG. 1B: a picture showing presence of TET2 proteins in primary human T cells edited by gRNAs target exon 4 or exon 6 of the TET2 gene as determined by a Western Blot assay. No full-length protein was detected in cells transfected with TET2 exon 4_BG4, and TET2 exon 6_BG5. TET2 exon 6_BG5 treatment also produces truncated TET2 protein species. FIG. 1C: a graph showing that modulation of TET2 significantly enhanced T cell proliferation and expansion in culture. Deletion of TET2 by TET2 exon 5_T1 and TET2 exon 5_T2 increased T cell proliferation compared to the mock group. T cells with truncated TET2 (TET2 exon 5_T1) had greater proliferation compared to all other groups. FIG. 1D: a graph showing that modulation of TET2 significantly enhanced T cell proliferation in culture. Deletion of TET2 by either TET2 exon4_BG4 (B G4) or TET2 exon 6_BG5 (B G5) increased T cell proliferation and expansion compared to cells not receiving Cas9:sgRNA RNP.

FIG. 2A: a graph showing highly efficient FAS gene editing in primary human T cells. FMO-FAS group represents fluorescence minus one group, a negative control for FAS signal. FIG. 2B: a graph showing that knockout of FAS improved IL-2/IL-7 driven proliferation of anti-BCMA CAR T cell in vitro. FIG. 2C: a graph showing that knockout of FAS rescued anti-BCMA CAR+ T cells from apoptosis induced by anti-FAS antibody.

FIG. 3A: a graph showing that FAS/TET2/CD70 triple knockout increased cell killing function (48 hour) of anti-CD19 CAR T cells. FIG. 3B: a graph showing that cell proliferation continued in triple knockout T cells after four weeks in culture.

FIG. 5A: a plot showing increase survival with the addition of TET2 KO in CAR T cells. FIG. 5B: a graph showing the addition of a TET2 KO further reduces tumor burden in mice treated with CAR T cells.

FIG. 6A: a graph showing the protective effect of TET2 KO in anti-CD19 CAR T cells with tumor re-challenge. FIG. 6B: a graph showing the protective effect of TET2 KO in anti-BCMA CAR T cells. FIG. 6C: a graph showing the protective effect of TET2 KO in anti-BCMA CAR T cells with tumor re-challenge. FIG. 6D: a graph showing the protective effect of TET2 KO in anti-CD70 CAR T cells. FIG. 6E: a graph showing the protective effect of TET2 KO in anti-CD70 CAR T cells with tumor re-challenge.

FIG. 8A: a diagram showing expansion growth curves of anti-BCMA CAR-T cells+/−TET2 KO following 3 rounds of MM.1S target cell stimulation. FIG. 8B: a diagram showing viability curves of anti-BCMA CAR-T cells+/−TET2 KO following 3 rounds of MM.1S target cell stimulation. FIG. 8C: a diagram showing FACS surface expression curves of anti-BCMA CAR-T cells+/−TET2 KO following 3 rounds of MM.1S target cell stimulation. FIG. 8D: a chart showing cytokine secretion (IFNγ) response following MM1S stimulation of anti-BCMA CAR-T cells+/−TET2 KO.

FIG. 9A: a chart showing continued cell proliferation, which is cytokine dependent. FIG. 9B: a chart showing cell killing activity of the allogenic human anti-CD19 CAR-T cells one month post spleen isolation. FIG. 9C: a graph showing interferon gamma secretion by the allogenic human anti-CD19 CAR-T cells. FIG. 9D: a graph showing interleukin 2 (IL-2) secretion by the allogenic human anti-CD19 CAR-T cells. FIG. 9E: a chart showing survival of the allogenic human anti-CD19 CAR-T cells in the Nalm6/NOG mouse model.

DETAILED DESCRIPTION OF THE INVENTION

Figure 1A:
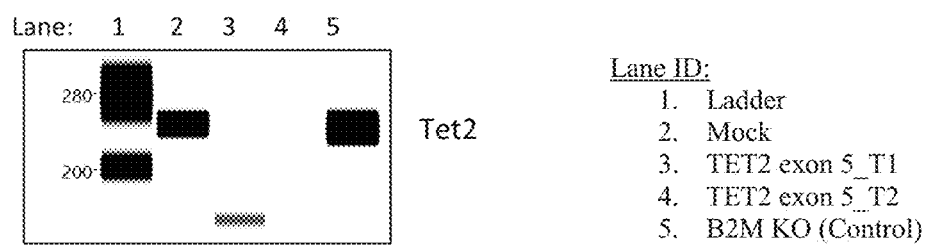
FIGS. 1A-1D include diagrams showing that mutations leading to either TET2 gene knockout (KO) or protein truncation increased proliferation and expansion, in primary human T cells.

The present disclosure aims at establishing a T cell bank comprising T cells having improved persistence, a long-felt need in CAR-T therapy. Such a T cell bank may use bona fide T cells as the starting material, for example, non-transformed T cells, terminally differentiated T cells, T cells having stable genome, and/or T cells that depend on cytokines and growth factors for proliferation and expansion. Alternatively, such a T cell bank may use T cells generated from precursor cells such as hematopoietic stem cells (e.g., iPSCs), e.g., in vitro culture. The T cell bank disclosed herein may confer one or more benefits in both CAR-T cell manufacturing and clinical applications.

Conventional allogenic CAR T cells are produced wherein a single donor leukopak is edited in most cases so that the cells can avoid components of the patient immune system and thus do not cause GvHD. The process of expanding these CAR T cells can yield 10s to 100s of vialed drug product. Patients may receive a single dose or multiple doses. During the manufacturing process, these CAR T cells lose potential due to various mechanisms, for example, apoptosis, exhaustion, replicative senescence, and other processes where the cells become less fit.

The edited T cell bank disclosed herein may provide a process whereby a single leukopak can create a cell bank of 10s to 100s of "vials" of cells, each of which can be used to create a multiple-vialed drug product of allogeneic CAR T cells. Both the banked cells and the CAR T cells produced from them are expected to retain more potential than CAR T cells produced by the standard (non-cell bank) process (without one or more of the genetic editing events disclosed herein).

Other unlimited advantageous features of the T cell bank provided herein include:

(a) Improved quality and consistency of drug products such as CAR-T products.

(b) Greater potency and longer-lived potency of CAR-T cells produced from the T cell bank cells in human patients.

(c) Reduced dosage requirement. Because the T cells disclosed herein have enhanced proliferation and expansion capacities, they can live longer in vivo. As such, a lower dose relative to standard CAR-T therapy could achieve substantially similar therapeutic effects as conventional CAR-T cells not having the gene edits disclosed herein (e.g., disruptions in TET2).

(d) Increase safety. The growth of the genetically engineered T cells disclosed herein were found to depend on cytokine, indicating no transformation. Further, since lower doses may be sufficient, use of the CAR-T cells disclosed herein would be expected to reduce side effects commonly associated with CART-T therapy, for example, cytokine release syndrome (CRS), macrophage activation syndrome (MAS), tumor lysis syndrome (TLS), and/or neurotoxic effects.

(e) Increased efficacy resulting from enhanced proliferation and expansion of the CAR-T cells disclosed herein, enhanced cytotoxicity, and prolonged persistence in vivo. Further, the T cell bank would provide the benefit of titratable dosing in patients to optimize safety and efficacy as noted above.

(f) Extended therapeutic effects due to reduced exhaustion and/or replicative senescence and prolonged persistence of the T cells in the T cell bank both in vitro and in vivo.

(g) Increasing the number of vialed drug product, such as allogeneic CAR T cell products, that can be created from a suitable natural source, such as a single leukopak.

Accordingly, provided herein are T cell banks that comprise T cells having improved persistence in culture, methods of producing such T cell banks, and methods of using such T cell banks for producing therapeutic T cells such as CAR-T cells. Components and processes (e.g., the CRISPR/Cas-mediated approach for gene editing and components used therein) for making the T cell banks disclosed herein are also within the scope of the present disclosure.

I. T Cell Bank Having Enhanced Persistence

The T cell bank disclosed herein comprises genetically engineered T cells having enhanced persistence in culture. Such genetically engineered T cells may have genetic editing of one or more genes involved in cell self-renewal, one or more genes involved in apoptosis, and/or one or more genes involved in T cell exhaustion. As shown by the studies disclosed herein, such genetically engineered T cells show one or more of the following superior features as relative to the non-edited T counterpart: enhanced expansion capacity in culture (e.g., expandable in culture for at least 4 weeks, e.g., at least 6 weeks; and/or at least 10-fold expandable, for example, at least 15-fold expandable, relative to the non-edited counterpart), enhanced proliferation capacity, greater T cell activation, and reduced apoptosis levels.

(i) Genetically Engineered T Cells in T Cell Banks

The genetically engineered T cells in the T cell bank disclosed herein comprise gene editing in one or more genes associated with T cell persistence in culture. "T cell persistence" as used herein refers to the tendency of T cells to continue to grow, proliferate, self-renew, expand, and maintain healthy activity in culture. In some instances, T cell persistence can be represented by the longevity that T cells can grow and expand in vitro, which can be measured by conventional methods and/or assays described herein. In other instances, T cell persistence can be represented by the reduction of cell death (e.g., apoptosis) or reduction in cell states characterized by exhaustion or replicative senescence. In yet other instances, T cell persistence can be presented by the maintenance of T cell activation capacity in culture.

T cell persistence of the genetically engineered T cells may be achieved by genetically editing one or more genes that function in regulating cell persistence via various pathways, for example, modulating cell self-renewal, apoptosis, and/or cell exhaustion. In some embodiments, the genetically engineered T cells may comprise gene editing of multiple genes involved in multiple pathways that regulate cell persistence. Such genetically engineered T cells may have increased longevity of growth in culture. Further, CAR-T cells derived from such genetically engineered T cells may also have enhanced in vivo therapeutic efficacy.

The genetically engineered T cells may be derived from parent T cells (e.g., non-edited wild-type T cells) obtained from a suitable source, for example, one or more mammal donors. In some examples, the parent T cells are primary T cells (e.g., non-transformed and terminally differentiated T cells) obtained from one or more human donors. Alternatively, the parent T cells may be differentiated from precursor T cells obtained from one or more suitable donor or stem cells such as hematopoietic stem cells or inducible pluripotent stem cells (iPSC), which may be cultured in vitro.

In some embodiments, the genetically engineered T cells comprise one or more mutated genes involved in cell self-renewal, one or more disrupted genes involved in apoptosis, and/or one or more disrupted genes involved in cell exhaustion. Such T cells may be generated via gene editing (including genomic editing), a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When a sequence of an endogenous gene is edited, for example by deletion, insertion or substitution of nucleotide(s)/nucleic acid(s), the endogenous gene comprising the affected sequence may be knocked-out or knocked-down due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

As used herein, a "mutated gene" encompasses any type of genetic mutations introduced into a target gene. In some instances, a "mutated gene" can include a genetic mutation that leads to expression of a mutated gene product (for example, a truncated gene product). In other instances, a "mutated gene" may be a disrupted gene, which may contain a genetic mutation that substantially or completely abolishes expression of the gene product.

As used herein, a "disrupted gene" refers to a gene comprising an insertion, deletion or substitution relative to an endogenous gene such that expression of a functional protein from the endogenous gene is reduced or inhibited. As used herein, "disrupting a gene" refers to a method of inserting, deleting or substituting at least one nucleotide/nucleic acid in an endogenous gene such that expression of a functional protein from the endogenous gene is reduced or inhibited. Methods of disrupting a gene are known to those of skill in the art and described herein.

In some embodiments, a cell that comprises a disrupted gene does not express (e.g., at the cell surface) a detectable level (e.g., in an immune assay using an antibody binding to the encoded protein or by flow cytometry) of the protein encoded by the gene. A cell that does not express a detectable level of the protein may be referred to as a knockout cell. In some embodiments, the genetically engineered T cells of the T cell bank disclosed herein may comprise a mutated TET2 gene, a disrupted FAS gene, a disrupted CD70 gene, or a combination thereof. In some instances, genetic editing of additional genes (e.g., β2M and/or TRAC) may also be included.

Tet Methylcytosine Dioxygenase 2 Gene (TET2) Editing

Self-renewal is the process by which cells (e.g., T cells) divide and maintain the same cell state/identity. Genes involved in cell self-renewal refer to those that either positively regulate or negatively regulate cell self-renewal. The genetically engineered T cells disclosed herein may comprise genetic editing of a gene that positively regulates cell self-renewal to enhance its expression and/or bioactivity of the encoded protein product. Alternatively or in addition, the genetically engineered T cells may comprise genetic editing of a gene that negatively regulates cell self-renewal to disrupt its expression.

In some embodiments, the genetically engineered T cells may comprise a mutated gene involved in cell self-renewal. Such a gene may be TET2 (Ten eleven translocation-2) a Methylcytosine Dioxygenase. Tet2 is a dioxygenase that catalyzes the conversion of the modified genomic base methylcytosine to 5-hydroxymethylcytosine and to further intermediates leading to cytosine demethylation. This enzyme is involved in myelopoiesis, and defects in TET2 have been reported to be associated with several myeloproliferative disorders. Structures of TET2 genes are known in the art. For example, human TET2 gene is located on chromosome 4q24. Additional information can be found in GenBank under Gene ID: 54790 or NCBI Reference Sequence: NM_001127208.2.

In some examples, the genetically engineered T cells may comprise a disrupted TET2 gene such that the expression of TET2 in the T cells is substantially reduced or eliminated completely. The disrupted TET2 gene may comprise one or more genetic edits at one or more suitable target sites (e.g., in coding regions or in non-coding regulatory regions such as promoter regions) that disrupt expression of the TET2 gene. Such target sites may be identified based on the gene editing approach for use in making the genetically engineered T cells. Exemplary target sites for the genetic edits may include exon 1, exon 3, exon 4, exon 5, exon 6, or a combination thereof. In some examples, one or more genetic edits may occur in exon 3, exon 4, exon 5, or exon 6. Such genetic editing may be induced by the CRISPR/Cas technology using a suitable guide RNA, for example, those listed in Table 3. The resultant edited TET2 gene using a gRNA listed in Table 3 may comprise one or more edited sequences provided in Tables 15-21 below.

In other examples, the genetically engineered T cells may comprise a mutated TET2 gene expressing a truncated version of TET2 protein, which may be a gain-of-function variant of TET2. Such a mutated TET2 gene may have a genetic edit in exon 5 and produces a truncated TET2 variant having a molecular weight of about 170 kDa, which can be determined by a conventional method such as SDS-PAGE.

The term "about" as used herein means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Where particular values are described in the application and claims, unless otherwise stated, the term "about" is implicit and in this context means within an acceptable error range for the particular value.

In some examples, the T cell bank as disclosed herein may comprise genetically engineered T cells, at least 50% of which comprise a disrupted TET2 gene (e.g., at least 60%, at least 70%, at least 80%, at least 90%, at least 95% or above). In some examples, the T cell bank as disclosed herein may comprise genetically engineered T cells, at least 50% of which comprise a mutated TET2 gene (e.g., at least 60%, at least 70%, at least 80%, at least 90%, at least 95% or above), which may express a truncated version of TET2 such as that disclosed above.

FAS Gene Editing

Apoptosis is a process of programmed cell death that occurs in multicellular organisms. Genes involved in apoptosis refer to those that either positively regulate or negatively regulate this biological process. The genetically engineered T cells disclosed herein may comprise genetic editing of a gene that positively regulates cell apoptosis to disrupt its expression. Alternatively or in addition, the genetically engineered T cells may comprise genetic editing of a gene that negatively regulates cell apoptosis to enhance its expression and/or biologic activity of the gene product.

In some embodiments, the genetically engineered T cells may comprise an edited gene involved in cell apoptosis, e.g., disruption of a gene that positively regulates apoptosis. Such a gene may be a FAS gene, also known as FAS receptor, CD95, or apoptosis antigen 1 (APO-1). The FAS gene encodes a death receptor on cell surface that leads to apoptosis when triggered by FAS ligand. FASL-FAS induced apoptosis is one of the multiple apoptotic pathways in cells (another major pathway being the mitochondrial pathway). Structures of FAS genes are known in the art. For example, human FAS gene is located on chromosome 10q24.1. Additional information can be found in GenBank under Gene ID: 355.

In some examples, the genetically engineered T cells may comprise a disrupted FAS gene such that the expression of FAS in the T cells is substantially reduced or eliminated completely. The disrupted FAS gene may comprise one or more genetic edits at one or more suitable target sites (e.g., in coding regions or in non-coding regulatory regions such as promoter regions) that disrupt expression of the FAS gene. Such target sites may be identified based on the gene editing approach for use in making the genetically engineered T cells. Exemplary target sites for the genetic edits may include exon 2, exon 3, or a combination thereof.

In some examples, the T cell bank as disclosed herein may comprise genetically engineered T cells, at least 50% of which comprise a disrupted FAS gene (e.g., at least 60%, at least 70%, at least 80%, at least 90%, at least 95% or above).

CD70 Gene Editing

T cell exhaustion is a process of stepwise and progressive loss of T cell functions, which may be induced by prolonged antigen stimulation or other factors. Genes involved in T cell exhaustion refer to those that either positively regulate or negatively regulate this biological process. The genetically engineered T cells disclosed herein may comprise genetic editing of a gene that positively regulates T cell exhaustion to disrupt its expression. Alternatively or in addition, the genetically engineered T cells may comprise genetic editing of a gene that negatively regulates T cell exhaustion to enhance its expression and/or biologic activity of the gene product.

In some embodiments, the genetically engineered T cells may comprise an edited gene involved in T cell exhaustion, e.g., disruption of a gene that positively regulates T cell exhaustion. Such a gene may be a Cluster of Differentiation 70 (CD70) gene. CD70 is a member of the tumor necrosis factor superfamily and its expression is restricted to activated T and B lymphocytes and mature dendritic cells. CD70 is implicated in tumor cell and regulatory T cell survival through interaction with its ligand, CD27. CD70 and its receptor CD27 have multiple roles in immune function in multiple cell types including T cells (activated and $T_{reg}$ cells), and B cells.

It was also found that disrupting the CD70 gene in immune cells engineered to express an antigen targeting moiety, enhanced anti-tumor efficacy against large tumors and induced a durable anti-cancer memory response. Specifically, the anti-cancer memory response prevented tumor growth upon re-challenge. Further, it has been demonstrated that disrupting the CD70 gene results in enhanced cytotoxicity of immune cells engineered to express an antigen targeting moiety at lower ratios of engineered immune cells to target cells, indicating the potential efficacy of low doses of engineered immune cells. See, e.g., WO2019/215500, the relevant disclosures of which are incorporated by reference for the purpose and subject matter referenced herein.

Structures of CD70 genes are known in the art. For example, human CD70 gene is located on chromosome 19p13.3. The gene contains four protein encoding exons. Additional information can be found in GenBank under Gene ID: 970.

In some examples, the genetically engineered T cells may comprise a disrupted CD70 gene such that the expression of CD70 in the T cells is substantially reduced or eliminated completely. The disrupted CD70 gene may comprise one or more genetic edits at one or more suitable target sites (e.g., in coding regions or in non-coding regulatory regions such as promoter regions) that disrupt expression of the CD70 gene. Such target sites may be identified based on the gene editing approach for use in making the genetically engineered T cells. Exemplary target sites for the genetic edits may include exon 1, exon 2, exon 3, exon 4, or a combination thereof. See also WO2019/215500, the relevant disclosures of which are incorporated by reference for the purpose and subject matter referenced herein.

In some examples, the T cell bank as disclosed herein may comprise genetically engineered T cells, at least 50% of which comprise a disrupted CD70 gene (e.g., at least 60%, at least 70%, at least 80%, at least 90%, at least 95% or above).

β2M Gene Edit

In some embodiments, the genetically engineered T cells in the T cell bank as disclosed herein may further comprise a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

In some embodiments, at least 50% (e.g., at least 60%, at least 70%, at least 80%, at least 90%, at least 95% or above) of the genetically engineered T cells in the T cell bank do not express a detectable level of β2M surface protein.

In some embodiments, an edited β2M gene may comprise a nucleotide sequence selected from the following sequences in Table 1. It is known to those skilled in the art that different nucleotide sequences in an edited gene such as an edited β2M gene (e.g., those in Table 1) may be generated by a single gRNA. See also WO2019097305, the relevant disclosures of which are incorporated by reference for the subject matter and purpose referenced herein.

TABLE 1

Sequences of exemplary gRNAs targeting β2M

| Sequences | SEQ ID NO: |
|---|---|
| CGTGGCCTTAGCTGTGCTCGCGCTACTCTCTCTTTCTGCCTGGA GGCTATCCAGCGTGAGTCTCTCCTACCCTCCCGCT | 1 |
| CGTGGCCTTAGCTGTGCTCGCGCTACTCTCTCTTTCGCCTGGAG GCTATCCAGCGTGAGTCTCTCCTACCCTCCCGCT | 2 |

TABLE 1-continued

Sequences of exemplary gRNAs targeting β2M

| Sequences | SEQ ID NO: |
|---|---|
| CGTGGCCTTAGCTGTGCTCGCGCTACTCTCTCTTTCTGGAGGCT ATCCAGCGTGAGTCTCTCCTACCCTCCCGCT | 3 |
| CGTGGCCTTAGCTGTGCTCGCGCTACTCTCTCTTTCTGGATAGC CTGGAGGCTATCCAGCGTGAGTCTCTCCTACCCTCCCGCT | 4 |
| CGTGGCCTTAGCTGTGCTCGCGCTATCCAGCGTGAGTCTCTCCT ACCCTCCCGCT | 5 |
| CGTGGCCTTAGCTGTGCTCGCGCTACTCTCTCTTTCTGTGGCCT GGAGGCTATCCAGCGGTCTCTCCTACCCTCCCGCT | 6 |

The genetically engineered T cells in the T cell bank disclosed herein may further comprise one or more additional gene edits (e.g., gene knock-in or knock-out) to improve T cell function. Examples include knock-in or knock-out genes to improve target cell lysis, knock-in or knock-out genes to enhance performance of therapeutic T cells such as CAR-T cells prepared from cells of the T cell bank. Examples include knock-out of an immune checkpoint gene such as PD-1.

TRAC Gene Edit

In some embodiments, the genetically engineered T cells in the T cell bank as disclosed herein may further comprise a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. See also WO2019097305, the relevant disclosures of which are incorporated by reference herein for the purpose and subject matter referenced herein.

It should be understood that more than one suitable target site/gRNA can be used for each target gene disclosed herein, for example, those known in the art or disclosed herein. Additional examples can be found in, e.g., WO2019097305, the relevant disclosures of which are incorporated by reference herein for the purpose and subject matter referenced herein.

Exemplary Genetically Engineered T cells in T cell Bank

In some embodiments, the T cell bank disclosed herein comprising a population of genetically engineered T cells that comprise a disrupted TET2 gene. Such genetically engineered T cells may further comprise a disrupted FAS gene, a disrupted CD70 gene, or both. In some embodiments, the T cell bank disclosed herein may comprise a population of genetically engineered T cells that comprise a combination of at least two of genetically edited genes selected from a mutated TET2 gene, a disrupted FAS gene, and a disrupted CD70 gene. Such genetically engineered T cells optionally may further comprise a disrupted β2M gene, a disrupted TRAC gene, or both.

In some examples, the T cell bank disclosed herein comprising a population of genetically engineered T cells that comprise a disrupted TET2 gene as disclosed herein. In some instances, at least 50% (e.g., 60%, 70%, 80%, 90%, or 95%) of the genetically engineered T cells in the T cell bank do not express surface TET2 at a detectable level as measured by a conventional assay.

In some examples, the T cell bank disclosed herein comprising a population of genetically engineered T cells that comprise a disrupted TET2 gene and a disrupted FAS gene. In some instances, at least 50% (e.g., 60%, 70%, 80%, 90%, or 95%) of the genetically engineered T cells in the T cell bank comprise the disrupted TET2 gene and the disrupted FAS gene.

In some examples, the T cell bank disclosed herein comprising a population of genetically engineered T cells that comprise that comprise a disrupted TET2 gene and a disrupted CD70 gene. In some instances, at least 50% (e.g., 60%, 70%, 80%, 90%, or 95%) of the genetically engineered T cells in the T cell bank comprise the mutated or disrupted TET2 gene and the disrupted CD70 gene.

In specific examples, the T cell bank disclosed herein comprising a population of genetically engineered T cells that comprise a disrupted TET2 gene, a disrupted FAS gene, and a disrupted CD70 gene. In some instances, at least 50% (e.g., 60%, 70%, 80%, 90%, or 95%) of the genetically engineered T cells in the T cell bank comprise the mutated or disrupted TET2 gene, the disrupted FAS gene, and the disrupted CD70 gene.

In some examples, the T cell bank disclosed herein comprising a population of genetically engineered T cells that comprise a mutated TET2 gene expressing any of the truncated TET2 polypeptide as disclosed herein and a disrupted FAS gene. In some instances, at least 50% (e.g., 60%, 70%, 80%, 90%, or 95%) of the genetically engineered T cells in the T cell bank comprise the mutated TET2 gene and the disrupted FAS gene.

In some examples, the T cell bank disclosed herein comprising a population of genetically engineered T cells that comprise a mutated TET2 gene expressing a truncated TET2 polypeptide as disclosed herein and a disrupted CD70 gene. In some instances, at least 50% (e.g., 60%, 70%, 80%, 90%, or 95%) of the genetically engineered T cells in the T cell bank comprise the mutated TET2 gene and the disrupted CD70 gene.

In specific examples, the T cell bank disclosed herein comprising a population of genetically engineered T cells that comprise a disrupted TET2 gene, a disrupted FAS gene, and a disrupted CD70 gene. In some instances, at least 50% (e.g., 60%, 70%, 80%, 90%, or 95%) of the genetically engineered T cells in the T cell bank comprise the disrupted TET2 gene, the disrupted FAS gene, and the disrupted CD70 gene.

In specific examples, the T cell bank disclosed herein comprising a population of genetically engineered T cells that comprise a mutated TET2 gene expressing any of the truncated TET2 polypeptide as disclosed herein, a disrupted FAS gene, and a disrupted CD70 gene. In some instances, at least 50% (e.g., 60%, 70%, 80%, 90%, or 95%) of the genetically engineered T cells in the T cell bank comprise the mutated TET2 gene, the disrupted FAS gene, and the disrupted CD70 gene.

In some embodiments, the genetically engineered T cells in the T cell bank, which may comprise one or more of a mutated TET2 gene (e.g., disrupted or mutated to express a truncated version of TET2 as disclosed herein), a disrupted FAS gene, and a disrupted CD70 may be expandable in culture for greater than 4 weeks, for example, greater than 5 weeks, greater than 6 weeks, greater than 8 weeks, and greater than 10 weeks. In some examples, the genetically engineered T cells in the T cell bank comprise a mutated TET2 gene expressing the truncated TET2 polypeptide as disclosed herein (optionally disruptions in FAS and/or CD70) and are expandable after 6 weeks (e.g., after 7 weeks, after 8 weeks, after 9 weeks, or after 10 weeks) in culture. Such genetically engineered T cells may maintain the ability to be activated after 6 weeks (e.g., after 7 weeks, after 8 weeks, after 9 weeks, or after 10 weeks) in culture. Further, such genetically engineered T cells have an increased expansion capacity, which can be at least 10-fold (e.g., at least 15-fold) higher than the non-engineered counterparts. Non-engineered counterparts refer to T cells having the same genetic background except for the gene involved in cell self-renewal (e.g., TET2), apoptosis (e.g., FAS), and/or T cell exhaustion (e.g., CD70) as disclosed herein, i.e., disrupted/mutated versus wild-type.

In some embodiments, the genetically engineered T cells in the T cell bank may comprise a disrupted FAS gene (optionally a mutated TET2 gene, e.g., disrupted or expressing the truncated TET2 polypeptide as disclosed herein and/or a disrupted CD70 gene) may have a reduced apoptosis tendency relative to the non-engineered counterparts. For example, the level of FAS/FAS ligand-induced apoptosis of the genetically engineered T cells in culture may be less than 50% (e.g., less than 40%, less than 30%, less than 20% or lower) of the FAS/FAS ligand induced apoptosis in non-engineered counterparts.

In some embodiments, CAR-T cells generated using the genetically engineered T cells in the T cell bank comprise a disrupted CD70 gene (optionally a mutated TET2 gene, e.g., disrupted or expressing the truncated TET2 polypeptide as disclosed herein and/or a disrupted FAS gene) may have an improved potency (e.g., at least 50% higher, at least one-fold higher, at least 2-folds higher, at least 5-folds higher, or at least 10-folds higher) both in vitro and in vivo relative to the non-engineered counterparts.

In some embodiments, the T cells in the T cell bank may further engineered to express a chimeric antigen receptor (CAR), which are described in detail below.

(ii) Methods of Making T Cell Banks

The genetically engineered T cells of the T cell bank disclosed herein can be prepared by genetic editing of parent T cells or precursor cells thereof via a conventional gene editing method or those described herein.

(a) T Cells

In some embodiments, T cells for use in making the T cell bank can be derived from one or more suitable mammals, for example, one or more human donors. T cells can be obtained from a number of sources, including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some examples, T cells can be isolated from a mixture of immune cells (e.g., those described herein) to produce an isolated T cell population, which can be used for making the T cell bank disclosed herein. For example, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, subpopulations of T cells may be isolated by positive or negative selection prior to genetic engineering and/or post genetic engineering.

An isolated population of T cells for use in making the T cell bank may express one or more of the T cell markers, including, but not limited to a CD3+, CD4+, CD8+, or a combination thereof. In some embodiments, the T cells are isolated from a donor, or subject, and first activated and stimulated to proliferate in vitro prior to undergoing gene editing.

In some instances, the T cell population for use in making the T cell bank comprises primary T cells isolated from one or more human donors. Such T cells are terminally differentiated, not transformed, depend on cytokines and/or growth factors for growth, and/or have stable genomes.

Alternatively, the T cells for use in making the T cell bank may be derived from stem cells (e.g., HSCs or iPSCs) via in vitro differentiation.

To achieve sufficient amount of T cells for making the T cell bank, T cells from a suitable source can be subjected to one or more rounds of stimulation, activation and/or expansion. T cells can be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; and 6,867,041. In some embodiments, T cells can be activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells. In some embodiments, T cells are activated at the same time that genome editing compositions are introduced into the T cells. In some instances, the T cell population can be expanded and/or activated after the genetic editing as disclosed herein. T cell populations or isolated T cells generated by any of the gene editing methods described herein are also within the scope of the present disclosure.

(b) Gene Editing Methods

Any of the genetically engineered T cells can be prepared using conventional gene editing methods or those described herein to edit one or more of the target genes disclosed herein (targeted editing). Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

In some embodiments, gene disruption may occur by deletion of a genomic sequence using two guide RNAs. Methods of using CRISPR-Cas gene editing technology to create a genomic deletion in a cell (e.g., to knock out a gene in a cell) are known (Bauer D E et al. Vis. Exp. 2015; 95;e52118).

Available endonucleases capable of introducing specific and targeted DSBs include, but not limited to, zinc-finger nucleases (ZFN), transcription activator-like effector nucleases (TALEN), and RNA-guided nuclease such as CRISPR/Cas (e.g., Clustered Regularly Interspaced Short Palindromic Repeats Associated protein 9 or CRISPR/Cas9). Additionally, DICE (dual integrase cassette exchange) system utilizing phiC31 and Bxb1 integrases may also be used for targeted integration. Some exemplary approaches are disclosed in detail below.

CRISPR-Cas9 Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

Endonuclease for Use in CRISPR

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 may be substituted with another RNA-guided endonuclease, such as Cpf1 (of a class II CRISPR/Cas system).

In some embodiments, the CRISPR/Cas system comprises components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease is from a Type-II CRISPR/Cas system (e.g., a Cas9 protein from a CRISPR/Cas9 system). In some embodiments, the Cas nuclease is from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

In some embodiments, a Cas nuclease may comprise more than one nuclease domain. For example, a Cas9 nuclease may comprise at least one RuvC-like nuclease domain (e.g., Cpf1) and at least one HNH-like nuclease domain (e.g., Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the S. pyogenes Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the S. pyogenes Cas9 nuclease).

In some embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

Guide RNAs (gRNAs)

The CRISPR technology involves the use of a genome-targeting nucleic acid that can direct the endonuclease to a specific target sequence within a target gene for gene editing at the specific target sequence. The genome-targeting nucleic acid can be an RNA. A genome-targeting RNA is referred to as a "guide RNA" or "gRNA" herein. A guide RNA comprises at least a spacer sequence that hybridizes to a target nucleic acid sequence within a target gene for editing, and a CRISPR repeat sequence.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

A spacer sequence in a gRNA is a sequence (e.g., a 20 nucleotide sequence) that defines the target sequence (e.g., a DNA target sequences, such as a genomic target sequence) of a target gene of interest. In some embodiments, the spacer sequence range from 15 to 30 nucleotides. For example, the spacer sequence may contain 15, 16, 17, 18, 19, 29, 21, 22, 23, 24, 25, 26, 27, 28, 29, or 30 nucleotides. In some embodiments, a spacer sequence contains 20 nucleotides.

The "target sequence" is in a target gene that is adjacent to a PAM sequence and is the sequence to be modified by an RNA-guided nuclease (e.g., Cas9). The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 7), then the gRNA spacer sequence is 5'-AGAGCAACAGUGCUGUGGCC-3' (SEQ ID NO: 8). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the S. pyogenes PAM.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

Non-limiting examples of gRNAs that may be used as provided herein are provided in WO2019097305, the relevant disclosures of which are herein incorporated by reference for the purposes and subject matter referenced herein. For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be an sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 2 below. In these exemplary sequences, the fragment of "n" refers to the spacer sequence at the 5' end.

TABLE 2

Exemplary sgRNA Formulas

| SEQ ID NO. | sgRNA sequence |
|---|---|
| 9 | nnnnnnnnnnnnnnnnnnnnguuuuagagcuagaaauagc aaguuaaaauaaggcuaguccguuaucaacuugaaaaagu ggcaccgagucggugcuuuu |
| 10 | nnnnnnnnnnnnnnnnnnnnguuuuagagcuagaaauagc aaguuaaaauaaggcuaguccguuaucaacuugaaaaagu ggcaccgagucggugc |

TABLE 2-continued

Exemplary sgRNA Formulas

| SEQ ID NO. | sgRNA sequence |
|---|---|
| 11 | n$_{(17-30)}$guuuuagagcuagaaauagcaaguuaaaauaaggcuaguccguuaucaacuugaaa aaguggcaccgagucggugcu$_{(1-8)}$ |

In some embodiments, the sgRNA comprises comprise no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

In some embodiments, the gRNAs disclosed herein target a TET2 gene, for example, target a site within exon 1, exon 2, exon 3, exon 4, exon 5, or exon 6 of the TET2 gene. Such a gRNA may comprise a spacer sequence complementary (complete or partially) to the target sequences in exon 3 or exon 5 of a TET2 gene, or a fragment thereof. Exemplary target sequences of TET2 and exemplary gRNA sequences are provided in Table 3 below:

TABLE 3

Exemplary TET2 gRNA Sequences/Target Sequences gRNA Sequences

| Name | Unmodified Sequence | Modified Sequence |
|---|---|---|
| TET2 exon4_BG4 (a.k.a., TET2-4) | CAUUAGGACCUGCUCCUAGAguuuuagagcuagaaauagcaaguuaaaauaaggcuaguccguuaucaacuugaaaaaguggcaccgagucggugcUUUU (SEQ ID NO: 12) | C*A*U*UAGGACCUGCUCCUAGAguuuuagagcuagaaauagcaaguuaaaauaaggcuaguccguuaucaacuugaaaaaguggcaccgagucggugcU*U*U*U (SEQ ID NO: 13) |
| TET2 exon 4_BG4 spacer | CAUUAGGACCUGCUCCUAGA (SEQ ID NO: 14) | C*A*U*UAGGACCUGCUCCUAGA (SEQ ID NO: 15) |
| TET2 exon 5_T1 (a.k.a., TET2-m5) | GGGAUGUCCUAUUGCUAAGUguuuuagagcuagaaauagcaaguuaaaauaaggcuaguccguuaucaacuugaaaaaguggcaccgagucggugcUUUU (SEQ ID NO: 16) | G*G*G*AUGUCCUAUUGCUAAGUguuuuagagcuagaaauagcaaguuaaaauaaggcuaguccguuaucaacuugaaaaaguggcaccgagucggugcU*U*U*U (SEQ ID NO: 17) |
| TET2 exon 5_T1spacer | GGGAUGUCCUAUUGCUAAGU (SEQ ID NO: 18) | G*G*G*AUGUCCUAUUGCUAAGU (SEQ ID NO: 19) |
| TET2 exon5 _T2 | AGGGAUGUCCUAUUGCUAAGguuuuagagcuagaaauagcaaguuaaaauaaggcuaguccguuaucaacuugaaaaaguggcaccgagucggugcUUUU (SEQ ID NO: 20) | A*G*G*GAUGUCCUAUUGCUAAGguuuuagagcuagaaauagcaaguuaaaauaaggcuaguccguuaucaacuugaaaaaguggcaccgagucggugcU*U*U*U (SEQ ID NO: 21) |
| TET2 exon 5_T2spacer | AGGGAUGUCCUAUUGCUAAG (SEQ ID NO: 22) | A*G*G*GAUGUCCUAUUGCUAAG (SEQ ID NO: 23) |
| TET2 exon 6_BG5 (a.k.a., TET2-5) | ACGGCACGCUCACCAAUCGCguuuugagcuagaaauagcaaguuaaaauaaggcuaguccguuaucaacuugaaaaagu ggcaccgagucggugcUUUU (SEQ ID NO: 24) | A*C*G*GCACGCUCACCAAUCGCguuuuagagcuagaaauagcaaguuaaaauaaggcuaguccguuaucaacuugaaaaagu ggcaccgagucggugcU*U*U*U (SEQ ID NO: 25) |
| TET2 exon 6_BG5 spacer | ACGGCACGCUCACCAAUCGC (SEQ ID NO: 26) | A*C*G*GCACGCUCACCAAUCGC (SEQ ID NO: 27) |
| TET2 exon 3_T1 spacer (a.k.a., TET2-1) | GAUUCCGCUUGGUGAAAACG (SEQ ID NO: 112) | G*A*U*UCCGCUUGGUGAAAACG (SEQ ID NO: 113) |

TABLE 3-continued

Exemplary TET2 gRNA Sequences/Target Sequences

| | | |
|---|---|---|
| TET2 exon 3_T1 | GAUUCCGCUUGGUGAAAACGguuu uagagcuagaaauagcaaguuaaa auaaggcuaguccguuaucaacuu gaaaaaguggcaccgagucggugc UUUU (SEQ ID NO: 114) | G*A*U*UCCGCUUGGUGAAAACGg uuuuagagcuagaaauagcaaguu aaaauaaggcuaguccguuaucaa cuugaaaaaguggcaccgagucgg ugcU*U*U*U (SEQ ID NO: 115) |
| TET2 exon 3_T2 spacer | CAGGACUCACACGACUAUUC (SEQ ID NO: 116) | C*A*G*GACUCACACGACUAUUC (SEQ ID NO: 117) |
| TET2 exon 3_T2 | CAGGACUCACACGACUAUUCguuu uagagcuagaaauagcaaguuaaa auaaggcuaguccguuaucaacuu gaaaaaguggcaccgagucggugc UUUU (SEQ ID NO: 118) | C*A*G*GACUCACACGACUAUUCg uuuuagagcuagaaauagcaaguu aaaauaaggcuaguccguuaucaa cuugaaaaaguggcaccgagucgg ugcU*U*U*U (SEQ ID NO: 119) |
| TET2 exon 3_T3 spacer | UUCCGCUUGGUGAAAACGAG (SEQ ID NO: 120) | U*U*C*CGCUUGGUGAAAACGAG (SEQ ID NO: 121) |
| TET2 exon 3_T3 | UUCCGCUUGGUGAAAACGAGguuu uagagcuagaaauagcaaguuaaa auaaggcuaguccguuaucaacuu gaaaaaguggcaccgagucggugc UUUU (SEQ ID NO: 122) | U*U*C*CGCUUGGUGAAAACGAGg uuuuagagcuagaaauagcaaguu aaaauaaggcuaguccguuaucaa cuugaaaaaguggcaccgagucgg ugcU*U*U*U (SEQ ID NO: 123) |

Target Sequences

| Name | Target Sequence (PAM) |
|---|---|
| TET2 exon 4_BG4 (a.k.a., TET2-4) | CATTAGGACCTGCTCCTAGA (TGG) (SEQ ID NO: 28) CATTAGGACCTGCTCCTAGA (SEQ ID NO: 124) |
| TET2 exon 5_T1 | GGGATGTCCTATTGCTAAGT (GGG) (SEQ ID NO: 29) GGGATGTCCTATTGCTAAGT (SEQ ID NO: 125) |
| TET2 exon5_T2 | AGGGATGTCCTATTGCTAAG (TGG) (SEQ ID NO: 30) AGGGATGTCCTATTGCTAAG (SEQ ID NO: 126) |
| TET2 exon 6_BG5 | ACGGCACGCTCACCAATCGC (CGG) (SEQ ID NO: 31) ACGGCACGCTCACCAATCGC (SEQ ID NO: 127) |
| TET2 exon 3_T1 | GATTCCGCTTGGTGAAAACG (AGG) (SEQ ID NO: 128) GATTCCGCTTGGTGAAAACG (SEQ ID NO: 129) |
| TET2 exon 3_T2 | CAGGACTCACACGACTATTC (TGG) (SEQ ID NO: 130) CAGGACTCACACGACTATTC (SEQ ID NO: 131) |
| TET2 exon 3_T3 | TTCCGCTTGGTGAAAACGAG (GGG) (SEQ ID NO: 132) TTCCGCTTGGTGAAAACGAG (SEQ ID NO: 133) |

*2'-O-methyl phosphorothioate residue

In some embodiments, a gRNA targeting a site in exon 3 of TET2 (e.g., those listed in Table 3 above) may be used for editing the TET2 gene. For example, a gRNA targeting the site of GATTCCGCTTGGTGAAAACG (SEQ ID NO: 129) may be used, e.g., a gRNA comprising a spacer of SEQ ID NO: 112 (unmodified) or SEQ ID NO: 113 (modified). Such a gRNA may comprise (e.g., consists of) the nucleotide sequence of SEQ ID NO: 114 (unmodified) or SEQ ID NO: 115 (modified). T cells edited by a gRNA targeting the site of SEQ ID NO: 129 may comprise a modified TET2 gene having at least one of the modifications listed in Table 15 below.

In another specific example, a gRNA targeting the site of CAGGACTCACACGACTATTC (SEQ ID NO: 131) may be used, e.g., a gRNA comprising a spacer of SEQ ID NO: 116 (unmodified) or SEQ ID NO: 117 (modified). Such a gRNA may comprise (e.g., consists of) the nucleotide sequence of SEQ ID NO: 118 (unmodified) or SEQ ID NO: 119 (modified). T cells edited by a gRNA targeting the site of SEQ ID NO: 131 may comprise a modified TET2 gene having at least one of the modifications listed in Table 16 below.

In another specific example, a gRNA targeting the site of TTCCGCTTGGTGAAAACGAG (SEQ ID NO: 133) may be used, e.g., a gRNA comprising a spacer of SEQ ID NO: 120 (unmodified) or SEQ ID NO: 121 (modified). Such a gRNA may comprise (e.g., consists of) the nucleotide sequence of SEQ ID NO: 122 (unmodified) or SEQ ID NO: 123 (modified). T cells edited by a gRNA targeting the site of SEQ ID NO: 133 may comprise a modified TET2 gene having at least one of the modifications listed in Table 17 below.

In other embodiments, a gRNA specific to the TET2 gene may target a site within exon 5. For example, a gRNA targeting the site of GGGATGTCCTATTGCTAAGT (SEQ ID NO: 125) in exon 5 may be used, e.g., a gRNA comprising a spacer of SEQ ID NO: 18 (unmodified) or SEQ ID NO: 19 (modified). Such a gRNA may comprise (e.g., consisting of) the nucleotide sequence of SEQ ID NO:16 (unmodified) or SEQ ID NO: 17 (modified). T cells edited by a gRNA targeting the site of SEQ ID NO: 125 may comprise a modified TET2 gene having at least one of the modifications listed in Table 19 below. In some instances, the genetic editing of the TET2 gene using such a gRNA may lead to expression of a truncated version of a TET2 protein, which may have a molecular weight about 170 kDa.

In other examples, a gRNA targeting the site of AGGGATGTCCTATTGCTAAG (SEQ ID NO: 126) in exon 5 may be used, e.g., a gRNA comprising a spacer of SEQ ID NO: 22 (unmodified) or SEQ ID NO: 23 (modified). Such a gRNA may comprise (e.g., consisting of) the nucleotide sequence of SEQ ID NO: 20 (unmodified) or SEQ ID NO: 21 (modified). T cells edited by a gRNA targeting the site of SEQ ID NO: 126 may comprise a modified TET2 gene having at least one of the modifications listed in Table 20 below.

In other embodiments, a gRNA specific to the TET2 gene may target a site within exon 4. For example, a gRNA targeting the site of CATTAGGACCTGCTCCTAGA (SEQ ID NO: 124) in exon 4 may be used, e.g., a gRNA comprising a spacer of SEQ ID NO: 14 (unmodified) or SEQ ID NO: 15 (modified). Such a gRNA may comprise (e.g., consisting of) the nucleotide sequence of SEQ ID NO:12 (unmodified) or SEQ ID NO: 13 (modified). T cells edited by a gRNA targeting the site of SEQ ID NO: 124 may comprise a modified TET2 gene having at least one of the modifications listed in Table 21 below.

In other embodiments, a gRNA specific to the TET2 gene may target a site within exon 6. For example, a gRNA targeting the site of ACGGCACGCTCACCAATCGC (SEQ ID NO: 127) in exon 6 may be used, e.g., a gRNA comprising a spacer of SEQ ID NO: 26 (unmodified) or SEQ ID NO: 27 (modified). Such a gRNA may comprise (e.g., consisting of) the nucleotide sequence of SEQ ID NO:24 (unmodified) or SEQ ID NO:25 (modified). T cells edited by a gRNA targeting the site of SEQ ID NO: 127 may comprise a modified TET2 gene having at least one of the modifications listed in Table 18 below.

In some embodiments, the gRNAs disclosed herein target a CD70 gene, for example, target a site within exon 1 or exon 3 of a CD70 gene. Such a gRNA may comprise a spacer sequence complementary (complete or partially) to the target sequences in exon 1 or exon 3 of a CD70 gene, or a fragment thereof. Exemplary target sequences in a CD70 gene and exemplary gRNAs specific to the CD70 gene are provided in Table 4 below.

TABLE 4

Exemplary CD70 gRNA Sequences/Target Sequences gRNA Sequences

| Name | Unmodified Sequence | Modified Sequence |
| --- | --- | --- |
| CD70 sgRNA (E1_T1) | UCACCAAGCCCGCGACCAA Uguuuuagagcuagaaauagcaaguuaa aauaaggcuaguccguuaucaacuugaa aaaguggcaccgagucggugcUUUU (SEQ ID NO: 32) | U*C*A*CCAAGCCCGCGACC AAUguuuuagagcuagaaauagcaag uuaaaauaaggcuaguccguuaucaacu ugaaaaaguggcaccgagucggugcU* U*U*U (SEQ ID NO: 33) |
| CD70 sgRNA (E1_T1) spacer | UCACCAAGCCCGCGACCAA U (SEQ ID NO: 34) | U*C*A*CCAAGCCCGCGACC AAU (SEQ ID NO: 35) |
| CD70 sgRNA (E1_T3) | AUCACCAAGCCCGCGACCA Aguuuuagagcuagaaauagcaaguuaa aauaaggcuaguccguuaucaacuugaa aaaguggcaccgagucggugcUUUU (SEQ ID NO: 36) | A*U*C*ACCAAGCCCGCGAC CAAguuuuagagcuagaaauagcaagu uaaaauaaggcuaguccguuaucaacuu gaaaaaguggcaccgagucggugcU*U *U*U (SEQ ID NO: 37) |
| CD70 sgRNA (E1_T3) spacer | AUCACCAAGCCCGCGACCA A (SEQ ID NO: 38) | A*U*C*ACCAAGCCCGCGAC CAA (SEQ ID NO: 39) |
| CD70 sgRNA (E1_T4) | CGGUGCGGCGCAGGCCCUA Uguuuuagagcuagaaauagcaaguuaa aauaaggcuaguccguuaucaacuugaa aaaguggcaccgagucggugcUUUU (SEQ ID NO: 40) | C*G*G*UGCGGCGCAGGCCC UAUguuuuagagcuagaaauagcaag uuaaaauaaggcuaguccguuaucaacu ugaaaaagugge accgagucggu gcU* U*U*U (SEQ ID NO: 41) |
| CD70 sgRNA (E1_T4) spacer | CGGUGCGGCGCAGGCCCUA U (SEQ ID NO: 42) | C*G*G*UGCGGCGCAGGCCC UAU (SEQ ID NO: 43) |
| CD70 sgRNA (E1_T7)); also referred to as: T7 | GCUUUGGUCCCAUUGGUCG Cguuuuagagcuagaaauagcaaguuaa aauaaggcuaguccguuaucaacuugaa aaaguggcaccgagucggugcUUUU (SEQ ID NO: 44) | G*C*U*UUGGUCCCAUUGG UCGCguuuuagagcuagaaauagcaa guuaaaauaaggcuaguccguuaucaac uugaaaaaguggcaccgagucggugcU *U*U*U (SEQ ID NO: 45) |
| CD70 sgRNA (E1_T7) spacer | GCUUUGGUCCCAUUGGUCG C (SEQ ID NO: 46) | G*C*U*UUGGUCCCAUUGG UCGC (SEQ ID NO: 47) |

TABLE 4-continued

Exemplary CD70 gRNA Sequences/Target Sequences

| | | |
|---|---|---|
| CD70 sgRNA (E1_T8); also referred to as: T8 | GCCCGCAGGACGCACCCAU Aguuuuagagcuagaaauagcaaguuaa aauaaggcuaguccguuaucaacuugaa aaaguggcaccgagucggugcUUUU (SEQ ID NO: 48) | G*C*C*CGCAGGACGCACCC AUAguuuuagagcuagaaauagcaag uuaaaauaaggcuaguccguuaucaacu ugaaaaaguggc accgagucggu gcU* U*U*U (SEQ ID NO: 49) |
| CD70 sgRNA (E1_T8) spacer | GCCCGCAGGACGCACCCAU A (SEQ ID NO: 50) | G*C*C*CGCAGGACGCACCC AUA (SEQ ID NO: 51) |
| CD70 sgRNA (E1_T10) | GUGCAUCCAGCGCUUCGCA Cguuuuagagcuagaaauagcaaguuaa aauaaggcuaguccguuaucaacuugaa aaaguggcaccgagucggugcUUUU (SEQ ID NO: 52) | G*U*G*CAUCCAGCGCUUCG CACguuuuagagcuagaaauagcaagu uaaaauaaggcuaguccguuaucaacuu gaaaaaguggcaccgagucggugcU*U *U*U (SEQ ID NO: 53) |
| CD70 sgRNA (E1_T10) spacer | GUGCAUCCAGCGCUUCGCA C (SEQ ID NO: 54) | G*U*G*CAUCCAGCGCUUCG CAC (SEQ ID NO: 55) |
| CD70 sgRNA (E3_T1) | CAGCUACGUAUCCAUCGUG Aguuuuagagcuagaaauagcaaguuaa aauaaggcuaguccguuaucaacuugaa aaaguggcaccgagucggugcUUUU (SEQ ID NO: 56) | C*A*G*CUACGUAUCCAUCG UGAguuuuagagcuagaaauagcaag uuaaaauaaggcuaguccguuaucaacu ugaaaaaguggc accgagucggu gcU* U*U*U (SEQ ID NO: 57) |
| CD70 sgRNA (E3_T1) spacer | CAGCUACGUAUCCAUCGUG A (SEQ ID NO: 58) | C*A*G*CUACGUAUCCAUCG UGA (SEQ ID NO: 59) |

Target Sequences

| Name | Target Sequence (PAM) | |
|---|---|---|
| CD70 target sequence with and without (PAM)(E1_T1) | TCACCAAGCCCGCGACCAAT (GGG) (SEQ ID NO: 60) TCACCAAGCCCGCGACCAAT (SEQ ID NO:134) | |
| CD70 target sequence with and without (PAM)(E1_T3) | ATCACCAAGCCCGCGACCAA (TGG) (SEQ ID NO: 61) ATCACCAAGCCCGCGACCAA (SEQ ID NO:135) | |
| CD70 target sequence with and without (PAM)(E1_T4) | CGGTGCGGCGCAGGCCCTAT (GGG) (SEQ ID NO: 62) CGGTGCGGCGCAGGCCCTAT (SEQ ID NO:136) | |
| CD70 target sequence with and without (PAM)(E1_T7) | GCTTTGGTCCCATTGGTCGC (GGG) (SEQ ID NO: 63) GCTTTGGTCCCATTGGTCGC (SEQ ID NO:137) | |
| CD70 target sequence with and without (PAM)(E1_T8) | GCCCGCAGGACGCACCCATA (GGG) (SEQ ID NO: 64) GCCCGCAGGACGCACCCATA (SEQ ID NO: 138) | |
| CD70 target sequence with and without (PAM)(E1_T10) | GTGCATCCAGCGCTTCGCAC (AGG) (SEQ ID NO: 65) GTGCATCCAGCGCTTCGCAC (SEQ ID NO: 139) | |
| CD70 target sequence with and without (PAM)(E3_T1) | CAGCTACGTATCCATCGTGA (TGG) (SEQ ID NO: 66) CAGCTACGTATCCATCGTGA (SEQ ID NO: 140) | |

*2'-O-methyl phosphorothioate residue

In some embodiments, the gRNAs disclosed herein target a FAS gene, for example, target a site within exon 1, exon 2, or exon 3 of a FAS gene. Such a gRNA may comprise a spacer sequence complementary (complete or partially) to the target sequences in exon 1, exon 2, or exon 3 of a FAS gene, or a fragment thereof. Exemplary target sequences in a FAS gene and exemplary gRNAs specific to the FAS gene are provided in Table 5 below.

TABLE 5

Exemplary FAS gRNA Sequences/Target Sequences gRNA Sequences

| Name | Unmodified Sequence | Modified Sequence |
|---|---|---|
| FAS sgRNA (FAS_Ex2_T1) | GUGACUGACAUCAACUCCAAguuu uagagcuagaaauagcaaguuaaa auaaggcuaguccguuaucaacuu gaaaaaguggcaccgagucggugc UUUU (SEQ ID NO: 67) | G*U*G*ACUGACAUCAACUCCAAg uuuuagagcuagaaauagcaaguu aaaauaaggcuaguccguuaucaa cuugaaaaaguggcaccgagucgg ugcU*U*U*U (SEQ ID NO: 68) |

TABLE 5-continued

Exemplary FAS gRNA Sequences/Target Sequences

| | | |
|---|---|---|
| FAS sgRNA (FAS_Ex2_T1) spacer | GUGACUGACAUCAACUCCAA (SEQ ID NO: 69) | G*U*G*ACUGACAUCAACUCCAA (SEQ ID NO: 70) |
| FAS sgRNA (FAS_Ex2_T2) | CACUUGGGCAUUAACACUUUguuu uagagcuagaaauagcaaguuaaa auaaggcuaguccguuaucaacuu gaaaaaguggcaccgagucggugc UUUU (SEQ ID NO: 71) | C*A*C*UUGGGCAUUAACACUUUg uuuuagagcuagaaauagcaaguu aaaauaaggcuaguccguuaucaa cuugaaaaaguggcaccgagucgg ugcU*U*U*U (SEQ ID NO: 72) |
| FAS sgRNA (FAS_Ex2_T2) spacer | CACUUGGGCAUUAACACUUU (SEQ ID NO: 73) | C*A*C*UUGGGCAUUAACACUUU (SEQ ID NO: 74) |
| FAS sgRNA (FAS_Ex2_T3) | UUGGAAGGCCUGCAUCAUGAguuu uagagcuagaaauagcaaguuaaa auaaggcuaguccguuaucaacuu gaaaaaguggcaccgagucggugc UUUU (SEQ ID NO: 75) | U*U*G*GAAGGCCUGCAUCAUGAg uuuuagagcuagaaauagcaaguu aaaauaaggcuaguccguuaucaa cuugaaaaaguggcaccgagucgg ugcU*U*U*U (SEQ ID NO: 76) |
| FAS sgRNA (FAS_Ex2_T3) spacer | UUGGAAGGCCUGCAUCAUGA (SEQ ID NO: 77) | U*U*G*GAAGGCCUGCAUCAUGA (SEQ ID NO: 78) |
| FAS sgRNA (FAS_Ex3_T1) | CUAGGGACUGCACAGUCAAUguuu uagagcuagaaauagcaaguuaaa auaaggcuaguccguuaucaacuu gaaaaaguggcaccgagucggugc UUUU (SEQ ID NO: 79) | C*U*A*GGGACUGCACAGUCAAUg uuuuagagcuagaaauagcaaguu aaaauaaggcuaguccguuaucaa cuugaaaaaguggcaccgagucgg ugcU*U*U*U (SEQ ID NO: 80) |
| FAS sgRNA (FAS_Ex3_T1) spacer | CUAGGGACUGCACAGUCAAU (SEQ ID NO: 81) | C*U*A*GGGACUGCACAGUCAAU (SEQ ID NO: 82) |
| FAS sgRNA (FAS_Ex3_T2) | ACUGCGUGCCCUGCCAAGAAguuu uagagcuagaaauagcaaguuaaa auaaggcuaguccguuaucaacuu gaaaaaguggcaccgagucggugc UUUU (SEQ ID NO: 83) | A*C*U*GCGUGCCCUGCCAAGAAg uuuuagagcuagaaauagcaaguu aaaauaaggcuaguccguuaucaa cuugaaaaaguggcaccgagucgg ugcU*U*U*U (SEQ ID NO: 84) |
| FAS sgRNA (FAS_Ex3_T2) spacer | ACUGCGUGCCCUGCCAAGAA (SEQ ID NO: 85) | A*C*U*GCGUGCCCUGCCAAGAA (SEQ ID NO: 86) |

Target sequences

| Name | Target Sequence (PAM) |
|---|---|
| FAS_Ex2_T1 target sequence with and without (PAM) | GTGACTGACATCAACTCCAA (GGG) (SEQ ID NO: 87) GTGACTGACATCAACTCCAA (SEQ ID NO: 141) |
| FAS_Ex2_T2 target sequence with and without (PAM) | CACTTGGGCATTAACACTTT (TGG) (SEQ ID NO: 88) CACTTGGGCATTAACACTTT (SEQ ID NO: 142) |
| FAS_Ex2_T3 target sequence with and without (PAM) | TTGGAAGGCCTGCATCATGA (TGG) (SEQ ID NO: 89) TTGGAAGGCCTGCATCATGA (SEQ ID NO: 143) |
| FAS_Ex3_T1 target sequence with and without (PAM) | CTAGGGACTGCACAGTCAAT (GGG) (SEQ ID NO: 90) CTAGGGACTGCACAGTCAAT (SEQ ID NO: 144) |
| FAS_Ex3_T2 target sequence with and without (PAM) | ACTGCGTGCCCTGCCAAGAA (GGG) (SEQ ID NO: 91) ACTGCGTGCCCTGCCAAGAA (SEQ ID NO: 145) |

*2'-O-methyl phosphorothioate residue

In other embodiments, a gRNA specific to the FAS gene may target a site within exon 2. For example, a gRNA targeting the site of SEQ ID NO: 142 in exon 2 of the FAS gene may be used, e.g., a gRNA comprising a spacer of SEQ ID NO: 73 (unmodified) or SEQ ID NO: 74 (modified). Such a gRNA may comprise (e.g., consisting of) the nucleotide sequence of SEQ ID NO: 71 (unmodified) or SEQ ID NO: 72 (modified) (e.g., FAS-Exon2-T2 gRNA). T cells edited by a gRNA targeting the site of SEQ ID NO: 142 may comprise a modified FAS gene having at least one of the modifications listed in Table 26 below.

In other embodiments, a gRNA specific to the FAS gene may target a site within exon 3. For example, a gRNA targeting the site of SEQ ID NO: 144 in exon 3 of the FAS gene may be used, e.g., a gRNA comprising a spacer of SEQ ID NO: 81 (unmodified) or SEQ ID NO: 82 (modified). Such a gRNA may comprise (e.g., consisting of) the nucleotide sequence of SEQ ID NO: 79 (unmodified) or SEQ ID NO: 80 (modified) (e.g., FAS-Exon3-T1 gRNA). T cells edited by a gRNA targeting the site of SEQ ID NO: 144 may comprise a modified FAS gene having at least one of the modifications listed in Table 27 below.

In other embodiments, a gRNA specific to the FAS gene may target a site within exon 3. For example, a gRNA targeting the site of SEQ ID NO: 145 in exon 3 of the FAS gene may be used, e.g., a gRNA comprising a spacer of SEQ ID NO: 85 (unmodified) or SEQ ID NO: 86 (modified). Such a gRNA may comprise (e.g., consisting of) the nucleotide sequence of SEQ ID NO: 83 (unmodified) or SEQ ID NO: 84 (modified) (e.g., FAS-Exon3-T2 gRNA). T cells edited by a gRNA targeting the site of SEQ ID NO: 145 may comprise a modified FAS gene having at least one of the modifications listed in Table 28 below.

In some embodiments, the gRNAs disclosed herein target a β2M gene, for example, target a suitable site within a β2M gene. See also International Application No. PCT/US2018/032334, filed May 11, 2018, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In some embodiments, the gRNAs disclosed herein target a TRAC gene. See also International Application No. PCT/US2018/032334, filed May 11, 2018, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and RNA-guided nuclease create breaks in the TRAC genomic region resulting Indels in the TRAC gene disrupting expression of the mRNA or protein.

Exemplary spacer sequences and gRNAs targeting a β2M gene or TRAC gene are provided in Table 6 below.

TABLE 6 gRNA Sequences/Target Sequences

| Name | Unmodified Sequence | Modified Sequence |
|---|---|---|
| TRAC sgRNA | AGAGCAACAGUGCUGUGGCCguuu uagagcuagaaauagcaaguuaaa auaaggcuaguccguuaucaacuu gaaaaaguggcaccgagucggugc UUUU (SEQ ID NO: 92) | A*G*A*GCAACAGUGCUGUGGCCg uuuuagagcuagaaauagcaaguu aaaauaaggcuaguccguuaucaa cuugaaaaaguggcaccgagucgg ugcU*U*U*U (SEQ ID NO: 93) |
| TRAC sgRNA spacer | AGAGCAACAGUGCUGUGGCC (SEQ ID NO: 94) | A*G*A*GCAACAGUGCUGUGGCC (SEQ ID NO: 95) |
| β2M sgRNA | GCUACUCUCUCUUUCUGGCCguuu uagagcuagaaauagcaaguuaaa auaaggcuaguccguuaucaacuu gaaaaaguggcaccgagucggugc UUUU (SEQ ID NO: 96) | G*C*U*ACUCUCUCUUUCUGGCCg uuuuagagcuagaaauagcaaguu aaaauaaggcuaguccguuaucaa cuugaaaaaguggcaccgagucgg ugcU*U*U*U (SEQ ID NO: 97) |
| β2M sgRNA spacer | GCUACUCUCUCUUUCUGGCC (SEQ ID NO: 98) | G*C*U*ACUCUCUCUUUCUGGCC (SEQ ID NO: 99) |

Target Sequences

| Name | Target Sequence (PAM) | |
|---|---|---|
| TRAC target sequence with and without (PAM) | AGAGCAACAGTGCTGTGGCC (TGG) (SEQ ID NO: 100) AGAGCAACAGTGCTGTGGCC (SEQ ID NO: 146) | |
| β2M target sequence with and without (PAM) | GCTACTCTCTCTTTCTGGCC (TGG) (SEQ ID NO: 101) GCTACTCTCTCTTTCTGGCC (SEQ ID NO: 147) | |

*2'-O-methyl phosphorothioate residue

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some examples, the gRNAs of the present disclosure can be are produced in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in WO2013/151666. Accordingly, the present disclosure also includes polynucleotides, e.g., DNA, constructs and vectors are used to in vitro transcribe a gRNA described herein.

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art. In some embodiments, non-natural modified nucleobases can be introduced into any of the gRNAs disclosed herein during synthesis or post-synthesis. In certain embodiments, modifications are on internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, enzymatic or chemical ligation methods can be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

In some embodiments of the present disclosure, a CRISPR/Cas nuclease system for use in genetically editing any of the target genes disclosed here may include at least one guide RNA. In some examples, the CRISPR/Cas nuclease system may contain multiple gRNAs, for example, 2, 3, or 4 gRNAs. Such multiple gRNAs may target different sites in a same target gene. Alternatively, the multiple gRNAs may target different genes. In some embodiments, the guide RNA(s) and the Cas protein may form a ribonucleoprotein (RNP), e.g., a CRISPR/Cas complex. The guide RNA(s) may guide the Cas protein to a target sequence(s) on one or more target genes as those disclosed herein, where the Cas protein cleaves the target gene at the target site. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

In some embodiments, the indel frequency (editing frequency) of a particular CRISPR/Cas nuclease system, comprising one or more specific gRNAs, may be determined using a TIDE analysis, which can be used to identify highly efficient gRNA molecules for editing a target gene. In some embodiments, a highly efficient gRNA yields a gene editing frequency of higher than 80%. For example, a gRNA is considered to be highly efficient if it yields a gene editing frequency of at least 80%, at least 85%, at least 90%, at least 95%, or 100%.

Delivery of Guide RNAs and Nucleases to T Cells

The CRISPR/Cas nuclease system disclosed herein, comprising one or more gRNAs and at least one RNA-guided nuclease, optionally a donor template as disclosed below, can be delivered to a target cell (e.g., a T cell) for genetic editing of a target gene, via a conventional method. In some embodiments, components of a CRISPR/Cas nuclease system as disclosed herein may be delivered to a target cell separately, either simultaneously or sequentially. In other embodiments, the components of the CRISPR/Cas nuclease system may be delivered into a target together, for example, as a complex. In some instances, gRNA and an RNA-guided nuclease can be pre-complexed together to form a ribonucleoprotein (RNP), which can be delivered into a target cell.

RNPs are useful for gene editing, at least because they minimize the risk of promiscuous interactions in a nucleic acid-rich cellular environment and protect the RNA from degradation. Methods for forming RNPs are known in the art. In some embodiments, an RNP containing an RNA-guided nuclease (e.g., a Cas nuclease, such as a Cas9 nuclease) and one or more gRNAs targeting one or more genes of interest can be delivered to a cell (e.g., a T cell). In some embodiments, an RNP can be delivered to a T cell by electroporation.

In some embodiments, an RNA-guided nuclease can be delivered to a cell in a DNA vector that expresses the RNA-guided nuclease in the cell. In other examples, an RNA-guided nuclease can be delivered to a cell in an RNA that encodes the RNA-guided nuclease and expresses the nuclease in the cell. Alternatively or in addition, a gRNA targeting a gene can be delivered to a cell as a RNA, or a DNA vector that expresses the gRNA in the cell.

Delivery of an RNA-guided nuclease, gRNA, and/or an RNP may be through direct injection or cell transfection using known methods, for example, electroporation or chemical transfection. Other cell transfection methods may be used.

Other Gene Editing Methods

Besides the CRISPR method disclosed herein, additional gene editing methods as known in the art can also be used in making the genetically engineered T cells disclosed herein. Some examples include gene editing approaching involve zinc finger nuclease (ZFN), transcription activator-like effector nucleases (TALEN), restriction endonucleases, meganucleases homing endonucleases, and the like.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination.

Any of the nucleases disclosed herein may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids. Some specific examples are provided below.

II. Use of T Cell Banks for Generating Therapeutic T Cells

The genetically engineered T cells from the T cell bank disclosed herein can be used to produce therapeutic T cells such as CAR-T cells. In some embodiments, a nucleic acid encoding a therapeutic agent such as a CAR may be introduced into cells from the T cell bank to generate the therapeutic T cells. In other embodiments, the T cells in the T cell bank have been engineered to express a therapeutic agent such as a CAR. Such T cells may be obtained from the T cell bank, and optionally expanded in vitro, to produce the therapeutic T cells for use in subjects in need of the treatment. Therapeutic T cells generated from the T cell bank are expected to live longer and be more potent in vivo. As such, a lower dose of such therapeutic T cells would be needed in therapy, which would result in lower side effects. In addition, a higher number of CAR-T cells can be generated from T cells isolated from a suitable natural source such as a single leukopak, as compared with conventional approaches using T cells (e.g., with a wild-type TET2 gene, a wild-type FAS gene, and/or a wild-type CD70 gene).

Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR T cells the ability to recognize an antigen independent of antigen processing, thus bypassing a major mechanism of tumor escape. Moreover, when expressed on T cells, CARs advantageously do not dimerize with endogenous T Cell Receptor (TCR) alpha and beta chains.

There are various generations of CARs, each of which contains different components. First generation CARs join an antibody-derived scFv to the CD3zeta or z) intracellular signaling domain of the T cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., *Blood*. 2015; 125(26):4017-4023; Kakarla and Gottschalk, *Cancer J*. 2014; 20(2):151-155). Any of the various generations of CAR constructs is within the scope of the present disclosure.

Generally, a CAR is a fusion polypeptide comprising an extracellular domain that recognizes a target antigen (e.g., a single chain fragment (scFv) of an antibody or other antibody fragment) and an intracellular domain comprising a signaling domain of the T Cell Receptor (TCR) complex (e.g., CD3) and, in most cases, a co-stimulatory domain. (Enblad et al., Human Gene Therapy. 2015; 26(8):498-505). A CAR construct may further comprise a hinge and transmembrane domain between the extracellular domain and the intracellular domain, as well as a signal peptide at the N-terminus for surface expression. Examples of signal peptides include MLLLVTSLLLCELPHPAFLLIP (SEQ ID NO: 102) and MALPVTALLLPLALLLHAARP (SEQ ID NO: 103). Other signal peptides may be used.

(i) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

Exemplary tumor antigens include, but are not limited to, CD19, CD33, BCMA, and CD70. Any known antibodies specific to such tumor antigens, for example, those approved for marketing and those in clinical trials, can be used for making the CAR constructs disclosed herein.

(ii) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain containing the sequence of FVPVFLPAKPTTTPAPRPPTPAPTIASQPLSLRPEACRPAAGG AVHTRGLDFACDIYIWA PLAGTCGVLLLSLVITLYCNHRNR (SEQ ID NO: 104) or IYIWAPLAGTCGVLLLSLVITLY (SEQ ID NO: 105). Other transmembrane domains may be used.

(iii) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(iv) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3. In some examples, the CAR disclosed herein comprises a CD28 co-stimulatory molecule. In other examples, the CAR disclosed herein comprises a 4-1BB co-stimulatory molecule. In some embodiments, a CAR includes a CD3ζ signaling domain and a CD28 co-stimulatory domain. In other embodiments, a CAR includes a CD3ζ signaling domain and 4-1BB co-stimulatory domain. In still other embodiments, a CAR includes a CD3ζ signaling domain, a CD28 co-stimulatory domain, and a 4-1BB co-stimulatory domain.

Table 7 provides examples of signaling domains derived from 4-1BB, CD28 and CD3-zeta that may be used herein.

TABLE 7

Exemplary Intracellular Signaling Domain Sequences

| Name | Sequence | SEQ ID NO: |
|---|---|---|
| 4-1BB | AAACGGGGCAGAAAGAAACTCCTGTATATATTCAAACAACCATTTATGAGACCAGTACAAACTACTCAAGAGGAAGATGGCTGTAGCTGCCGATTTCCAGAAGAAGAAGAAGGAGGATGTGAACTG | 106 |
|  | KRGRKKLLYIFKQPFMRPVQTTQEEDGCSCRFPEEEEGGCEL | 107 |
| CD28 | TCAAAGCGGAGTAGGTTGTTGCATTCCGATTACATGAATATGACTCCTCGCCGGCCTGGGCCGACAAGAAAACATTACCAACCCTATGCCCCCCCACGAGACTTCGCTGCGTACAGGTCC | 108 |
|  | SKRSRLLHSDYMNMTPRRPGPTRKHYQPYAPPRDFAAYRS | 109 |

TABLE 7-continued

Exemplary Intracellular Signaling Domain Sequences

| Name | Sequence | SEQ ID NO: |
|------|----------|------------|
| CD3ζ | CGAGTGAAGTTTTCCCGAAGCGCAGACGCTCCGGCATATCAGCAAGGACAG<br>AATCAGCTGTATAACGAACTGAATTTGGGACGCCGCGAGGAGTATGACGTG<br>CTTGATAAACGCCGGGGGAGAGACCCGGAAATGGGGGGTAAACCCCGAAGA<br>AAGAATCCCCAAGAAGGACTCTACAATGAACTCCAGAAGGATAAGATGGCG<br>GAGGCCTACTCAGAAATAGGTATGAAGGGCGAACGACGACGGGGAAAAGGT<br>CACGATGGCCTCTACCAAGGGTTGAGTACGGCAACCAAAGATACGTACGAT<br>GCACTGCATATGCAGGCCCTGCCTCCCAGA | 110 |
| | RVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYD<br>ALHMQALPPR | 111 |

Non-limiting examples of CAR constructs are provided in WO2019097305 and WO2019215500, and WO2020/095107, the relevant disclosures of which are herein incorporated by reference for the purposes and subject matter referenced herein. Some examples are provided below:

Anti-CD19 CAR (SEQ ID NO: 148):
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSAAAFVPVFLPAKPTTTPAPRPPTPAPTIASQPLS

LRPEACRPAAGGAVHTRGLDFACDIYIWAPLAGTCGVLLLSLVITLYCNH

RNRSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQ

ALPPR

Anti-BCMA CAR (SEQ ID NO: 149):
MALPVTALLLPLALLLHAARPQVQLVQSGAELKKPGASVKVSCKASGNTL

TNYVIHWVRQAPGQRLEWMGYILPYNDLTKYSQKFQGRVTITRDKSASTA

YMELSSLRSEDTAVYYCTRWDWDGFFDPWGQGTTVTVSSGGGGSGGGGSG

GGGSEIVMTQSPATLSVSPGERASISCRASQSLVHSNGNTHLHWYQQRPG

QAPRLLIYSVSNRFSEVPARFSGSGSGTDFTLTISSVESEDFAVYYCSQT

SHIPYTFGGGTKLEIKSAAAFVPVFLPAKPTTTPAPRPPTPAPTIASQPLS

LRPEACRPAAGGAVHTRGLDFACDIYIWAPLAGTCGVLLLSLVITLYCNH

RNRKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALH

MQALPPR

Anti-CD 70 CAR (SEQ ID NO: 150):
MALPVTALLLPLALLLHAARPQVQLVQSGAEVKKPGASVKVSCKASGYTF

TNYGMNWVRQAPGQGLKWMGWINTYTGEPTYADAFKGRVTMTRDTSISTA

YMELSRLRSDDTAVYYCARDYGDYGMDYWGQGTTVTVSSGGGGSGGGGSG

GGGSGDIVMTQSPDSLAVSLGERATINCRASKSVSTSGYSFMHWYQQKPG

QPPKLLIYLASNLESGVPDRFSGSGSGTDFTLTISSLQAEDVAVYYCQHS

REVPWTFGQGTKVEIKSAAAFVPVFLPAKPTTTPAPRPPTPAPTIASQPL

SLRPEACRPAAGGAVHTRGLDFACDIYIWAPLAGTCGVLLLSLVITLYCN

HRNRKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPR

Exemplary anti-CD33 CAR constructs can be found in WO2020095107, the relevant disclosures of which are incorporated by reference for the subject matter and purpose referenced herein.

Delivery of CAR Construct to T Cells

In some embodiments, a nucleic acid encoding a CAR can be introduced into any of the genetically engineered T cells from the T cell bank disclosed herein by methods known to those of skill in the art. For example, a coding sequence of the CAR may be cloned into a vector, which may be introduced into the genetically engineered T cells for expression of the CAR. A variety of different methods known in the art can be used to introduce any of the nucleic acids or expression vectors disclosed herein into an immune effector cell. Non-limiting examples of methods for introducing nucleic acid into a cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

In specific examples, a nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions disclosed herein can be used for this purpose.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some embodiments, a disruption in the TRAC gene can be created with an endonuclease as those disclosed herein and one or more gRNAs targeting one or more TRAC genomic regions, and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using a gene editing method known in the art. In some examples, a CRISPR-based method can be used. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, can be inserted at a site nearby an endogenous prompter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

When needed, additional gene editing (e.g., gene knock-in or knock-out) can be introduced into therapeutic T cells produced from the T cell bank as disclosed herein to improve T cell function and therapeutic efficacy. For example, if β2M knockout can be performed to reduce the risk of or prevent a host-versus-graft response. Other examples include knock-in or knock-out genes to improve target cell lysis, knock-in or knock-out genes to enhance performance of therapeutic T cells such as CAR-T cells prepared from cells of the T cell bank. Examples include knock-out of an immune checkpoint gene such as PD-1.

III. Therapeutic Applications

The therapeutic T cells generated using the genetically engineered T cells of the T cell bank would be expected to maintain T cell health enabled by the mutation in the TET2 gene, the disruption of the FAS gene, the disruption of the CD70 gene, or a combination thereof. For example, maintaining T cell health may extend expansion during manufacturing, thereby increasing yield and consistency. In another example, maintaining T cell health may rescue exhausted/unhealthy T cells, thereby enabling potentially lower doses in patients and more robust responses.

The therapeutic T cells generated using the T cell bank disclosed herein can be administered to a subject for therapeutic purposes, for example, treatment of a solid tumor targeted by the CAR construct expressed by the therapeutic T cells.

The step of administering may include the placement (e.g., transplantation) of the therapeutic T cells into a subject by a method or route that results in at least partial localization of the therapeutic T cells at a desired site, such as a tumor site, such that a desired effect(s) can be produced. Therapeutic T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of the therapeutic T cells can be administered via a systemic route of administration, such as an intraperitoneal or intravenous route.

In some embodiments, the therapeutic T cells are administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

A subject may be any subject for whom diagnosis, treatment, or therapy is desired. In some embodiments, the subject is a mammal. In some embodiments, the subject is a human.

In some instances, the therapeutic T cells may be autologous ("self") to the subject, i.e., the cells are from the same subject. Alternatively, the therapeutic T cells can be non-autologous ("non-self," e.g., allogeneic, syngeneic or xenogeneic) to the subject. "Allogeneic" means that the therapeutic T cells are not derived from the subject who receives the treatment but from different individuals (donors) of the same species as the subject. A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient (e.g., subject). For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

Because of the enhanced persistence and efficacy of the therapeutic T cells produced from the T cell bank disclosed herein, the dose of the therapeutic T cells provided herein may be lower than the standard dose of CAR-T cells prepared by conventional approaches (e.g., using T cells that do not have one or more of the genetic editing events disclosed herein, including a mutated TET2 gene, a disrupted FAS gene, and/or a disrupted CD70 gene). In some examples, the effective amount of the therapeutic T cells disclosed herein may be at least 2-fold lower, at least 5-fold lower, at least 10-fold lower, at least 20-fold lower, at least 50-fold lower, or at least 100-fold lower than a standard dose of a CAR-T therapy. In some examples, an effective amount of the therapeutic T cells disclosed herein may be less than $10^6$ cells, e.g., $10^5$ cells, $5\times10^4$ cells, $10^4$ cells, $5\times10^3$ cells, or $10^3$ cells. In some examples described herein, the cells are expanded in culture prior to administration to a subject in need thereof.

The efficacy of a treatment using the therapeutic T cells disclosed herein can be determined by the skilled clinician. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Combination therapies are also encompassed by the present disclosure. For example, the therapeutic T cells disclosed herein may be co-used with other therapeutic agents, for treating the same indication, or for enhancing efficacy of the therapeutic T cells and/or reducing side effects of the therapeutic T cells.

Kits

The present disclosure also provides kits for use in producing the T cell bank, the therapeutic T cells, and for therapeutic uses, In some embodiments, a kit provided herein may comprise components for performing genetic edit of one or more of TET2 gene, FAS gene, and CD70 gene, and optionally a population of immune cells to which the genetic editing will be performed (e.g., a leukopak). A leukopak sample may be an enriched leukapheresis product collected from peripheral blood. It typically contains a variety of blood cells including monocytes, lymphocytes, platelets, plasma, and red cells. The components for genetically editing one or more of the target genes may comprise a suitable endonuclease such as an RNA-guided endonuclease and one or more nucleic acid guides, which direct cleavage of one or more suitable genomic sites by the endonuclease. For example, the kit may comprise a Cas enzyme such as Cas 9 and one or more gRNAs targeting a TET2 gene, a FAS gene, and/or a CD70 gene. Any of the gRNAs specific to these target genes can be included in the kit. Such a kit may further comprise components for further gene editing, for example, gRNAs and optionally additional endonucleases for editing other target genes such as β2M and/or TRAC.

In some embodiments, a kit provided herein may comprise a population of genetically engineered T cells of the T cell bank as disclosed herein, and one or more components for producing the therapeutic T cells as also disclosed herein. Such components may comprise an endonuclease suitable for gene editing and a nucleic acid coding for a CAR construct of interest. The CAR-coding nucleic acid may be part of a donor template as disclosed herein, which may contain homologous arms flanking the CAR-coding sequence. In some instances, the donor template may be carried by a viral vector such as an AAV vector. The kit may further comprise gRNAs specific to a TRAC gene for inserting the CAR-coding sequence into the TRAC gene.

In yet other embodiments, the kit disclosed herein may comprise a population of therapeutic T cells as disclosed for the intended therapeutic purposes.

Any of the kit disclosed herein may further comprise instructions for making the T cell bank, the therapeutic T cells, or therapeutic applications of the therapeutic T cells. In some examples, the included instructions may comprise a description of using the gene editing components to genetically engineer one or more of the target genes (e.g., TET2, FAS, CD70, or a combination thereof) for making the T cell bank from parent T cells of a suitable source (e.g., those described herein). In other examples, the included instructions may comprise a description of how to introduce a nucleic acid encoding a CAR construction into the T cells of the T cell bank for making therapeutic T cells.

Alternatively, the kit may further comprise instructions for administration of the therapeutic T cells as disclosed herein to achieve the intended activity, e.g., eliminating disease cells targeted by the CAR expressed on the therapeutic T cells. The kit may further comprise a description of selecting a subject suitable for treatment based on identifying whether the subject is in need of the treatment. The instructions relating to the use of the therapeutic T cells described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the therapeutic T cells are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an infusion device for administration of the therapeutic T cells. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Effects of TET2 Knockout (KO) or Mutation on Primary Human T Cells (i) Efficient Knockout or Mutation of TET2 by Cas9: sgRNA RNPs in T Cells This example describes efficient editing of the TET2 gene in T cells derived from primary human PBMC cells ex vivo using CRISPR/Cas9 gene editing. Genomic segments of the TET2 gene containing the fourth, fifth and sixth protein coding exons were used as input in gRNA design software. Desired gRNAs were those that would lead to deletions in the coding sequence, disrupting the amino acid sequence of TET2, and leading to out of frame/loss of function allele (referred to as "TET2 knockout" alleles or truncation of the TET2 protein). Four (4) in silico-identified gRNA spacer sequences targeting the TET2 gene were synthesized and the gRNAs were specifically modified, as indicated in Table 1. While the gRNAs in Table 1 were modified with 2'-O-methyl phosphorothioate modifications, unmodified gRNAs, or gRNAs with other modifications, may be used. See also WO2019097305, the relevant disclosures of which are incorporated by reference for the purpose and subject matter referenced herein.

Activated T cells derived from primary human PBMC cells were transfected (electroporated) with a ribonucleoprotein particle (RNP) containing Cas9 nuclease and a synthetic modified sgRNA targeting the TET2 gene (sequences in Table 3 above) or controls (no Cas9, no gRNA). Six (6) days post transfection, cells were immunoblotted to assess indel efficiency.

Figure 1B:
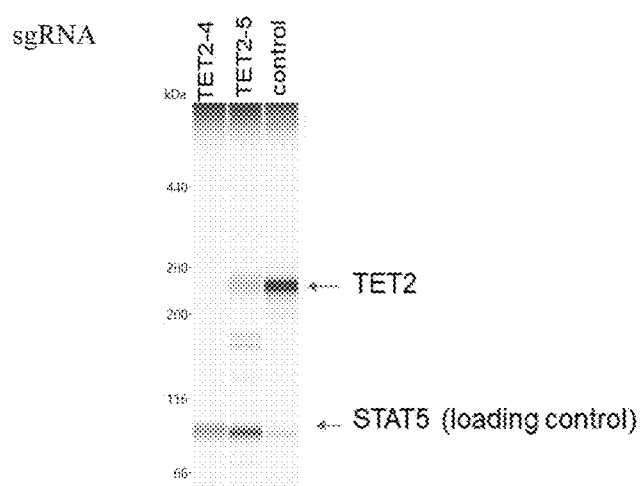
Figure 1C:
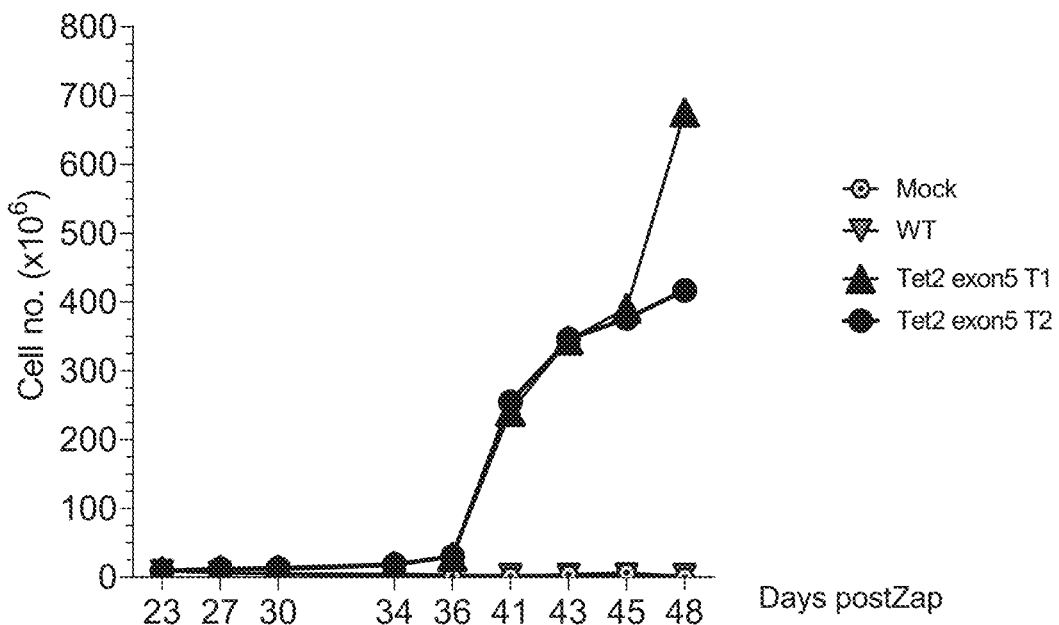

As show in FIGS. 1A-1B, no TET2 protein was detected determined by a capillary-based size-separation immunoassay termed Simple Western (protein simple, San Jose, CA) in cells treated with gRNAs TET2 exon 4_BG4, TET2 exon 5_T1, TET2 exon 5_T2, or TET2 exon 6_BG5, and a truncated form(s) of the TET2 protein (having a lower apparent molecular weight than wild-type TET2) was detected in cells treated with either the TET2 exon 5_T1 gRNA or Exon 6_BG5 gRNA.

(ii) TET2 KO or Mutation Increased T Cell Proliferation and Expansion

To assess the effect of TET2 modulation (including disruption or truncated mutation) on the ability of T cells to expand in cytokine containing media (IL-2+IL-7), cells with disrupted or mutated TET2 gene were generated as described above. Equal numbers of cells were plated at $1.5 \times 10^6$ cells/ml of cytokine containing media (IL-2+IL-7), cell counts were recorded every 2-3 days, and cells density was adjusted at $1.5 \times 10^6$ cells/ml in fresh cytokine containing media (IL-2+IL-7). T cells containing a disruption in the TET2 gene induced by TET2 exon5_T1 or TET2 exon5_T2 expanded to greater levels as compared to control cells without a TET2 gene disruption (FIG. 1B). More than 6 weeks post-transfection, TET2 edited cells with TET2 exon5_T1 or TET2 exon5_T2 gRNAs kept proliferating and the modulation of TET2 by TET2 exon5_T1 gRNA (resulting in a truncated form of TET2) results in greater cell yields in culture compared to other groups and caused an increase of more than 250 fold in the cell yield compared to non-transfected cells (WT). FIG. 1B.

Figure 1D:
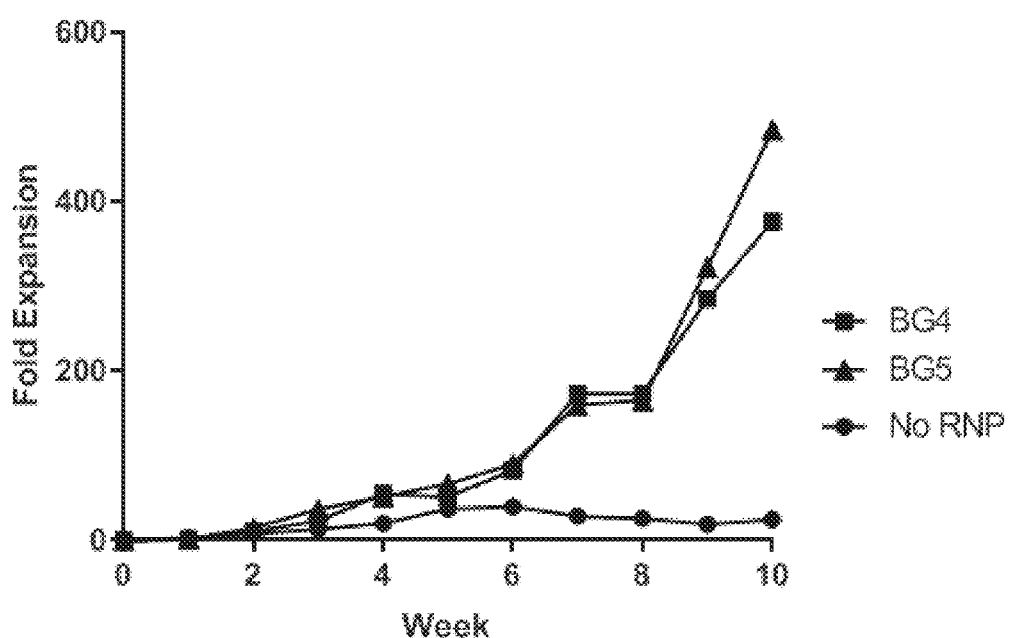

To assess if disruptions of other TET2 coding exons leads to greater T cell expansion T cells were generated with disruptions in the TET2 gene after treatment with TET2 exon 4_BG4 and TET2 exon 6_BG5 gRNAs. After the T cells were edited they were grown for 4 weeks under standard T-cell culture conditions (X-vivo medium (04-744, Lonza), supplemented with 5% human AB serum (HP1022, Valley Biomedical), 50 ng/ml IL-2 (rhIL-2; 130-097-745, Miltenyi Biotech) and 10 ng/ml IL-7 (rhIL-7; Cellgenix 001410-050). After four weeks, $3 \times 10^6$ cells were plated into a G-Rex (Gas Permeable Rapid Expansion, Wilson Wolf P/N80660M) 6 well plate. Cell expansion was assessed as by counting viable cells once a week for a ten-week period. The expansion was recorded as a fold change of the initial plating of $3 \times 10^6$ cells to the most current cell count (i.e. current cell count/$3 \times 10^6$ cells). Cells were maintained at $1 \times 10^6$ cells per mL in complete media. As shown in FIG. 1D, TET2 KO produced by disrupting either exon 4 or exon6 of the TET2 gene led to 15-19 fold expansion over the No RNP treated control T-Cells during a 10 week enumeration period (14 weeks total in culture).

In sum, TET2 modified T cells were found to be expandable in culture for greater than 4 weeks, much longer than non-modified T cells.

(iii) TET2 KO or Truncated Mutation Reduces Apoptotic Cell Numbers in Extended Cell Cultures The number of TET2 deficient cells undergoing apoptosis in extended cell culture was evaluated at day 36 post-electroporation. Briefly, an aliquot of cells was washed and stained with FITC-conjugated annexin V along with 7-AAD in annexin V binding buffer (BioLegend) for 15 minutes at room temperature. Cells were then washed and resuspend in annexin V binding buffer for analysis by flow cytometry. As shown in Table 8 below, T cells edited with TET2 exon5_T1 or TET2 exon5_T2 gRNAs showed a reduction in apoptotic cells and an increase in the percentage of healthy cells by 7-8 folds compared to unedited cells.

TABLE 8

Percentage of Healthy Cells at Day 36 Post-Electroporation

| | Healthy Cells | Annexin-V$^+$ Cells | 7-AAD$^+$ Cells | Annexin-V$^+$/7-AAD$^+$ Cells |
|---|---|---|---|---|
| Mock | 8.48% | 60.3% | 0.48% | 30.7% |
| TET2 exon5_T1 | 61.3% | 21.1% | 0.21% | 17.4% |
| TET2 exon5_T2 | 64.3% | 20.5% | 0.13% | 16.1% |

(iv) TET2 KO and Truncated Mutation Increased the Number of Activatable T Cells in Extended Cell Cultures To assess the ability of TET2–modified T cells to be activated in extended cell cultures, cells with disrupted TET2 gene were generated as described above. At day forty-five (45) post-transfection, $0.5 \times 10^6$ T cells were treated with BD Golgiplug for one (1) hour followed by activation with PMA/Ionomycin for four (4) hours in the presence of Golgiplug. Cells were collected and surface-stained for activation markers and intracellularly-stained for IFN-γ production. T cells containing a disruption and truncated mutation in the TET2 gene caused by TET2 exon3_T3 and TET2 exon5_T1, respectively, showed a greater frequency of activated and IFN-γ-positive cells (CD25$^+$, IFN-γ$^+$ cells), as compared to control cells without a TET2 gene disruption or T cells transfected with other gRNAs. See the results in Table 9 below.

TABLE 9

Percentage of IFN-γ$^+$/CD25$^+$ T cells in Genetically Edited T cells

| | Mock | TET2 exon5_T1 | TET2 exon5_T2 |
|---|---|---|---|
| CD25$^+$/IFN-γ$^+$ cell % | 0 | 13.1 | 4.75 |

Example 2

FAS Knockout (KO) Increased Proliferation and Reduced Apoptosis (i) Knockout of FAS by Cas9:sgRNA RNPs in T Cells This example describes efficient editing of the FAS gene in primary human T cells ex vivo using the CRISPR/Cas9 gene editing approach. Desired gRNAs were those that would lead to insertions or deletions in the coding sequence, disrupting the amino acid sequence of FAS, leading to out of frame/loss of function allele(s) (referred to as "FAS knockout" alleles). All five (5) in silico-identified gRNA spacer sequences targeting the FAS gene were synthesized.

Primary human T cells from two healthy donors were transfected (electroporated) with a ribonucleoprotein particle (RNP) containing a Cas9 nuclease and a synthetic modified sgRNA (with 2'-O-methyl phosphorothioate modifications) targeting the FAS gene (sequences in Table 5 above) or controls (no Cas9, no gRNA). Six (6) days post transfection, cells were processed by flow cytometry (primary antibody: PE Dazzle 594 anti-human FAS antibody, clone DX2, Biolegend) to assess FAS expression levels at the cell surface.

Figure 2A:
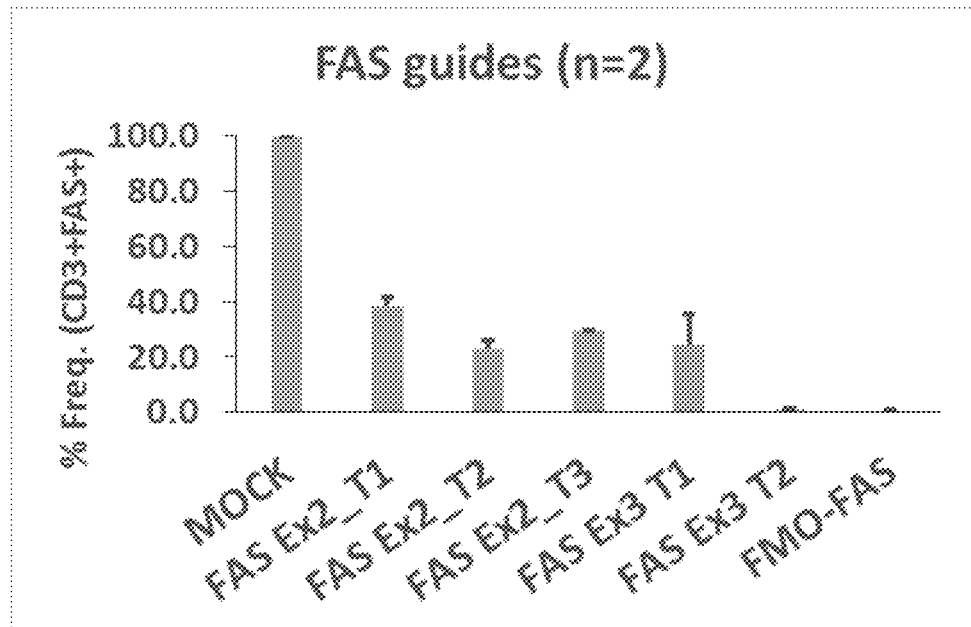
FIGS. 2A-2C include diagrams showing that FAS knockout (KO) increased cytokine driven proliferation and rescued apoptosis in anti-BCMA CAR T cells in vitro.

As shown in FIG. 2A, the gRNAs listed in Table 5 above all led to certain level of FAS knockout with gRNA FAS Ex3_T2 having the highest editing efficiency.

(ii) FAS KO Increased Cytokine Driven Proliferation of Anti-BCMA CAR T Cells

To evaluate the effect of FAS and/or CD70 knockout on cell proliferation, anti-BCMA CAR T cells were utilized. The following groups of edited T BCMA-CAR T cells were generated:

TRAC-/B2M-/anti-BCMA CAR+ (Control; 2KO, BCMA CAR+)

TRAC-/B2M-/FAS-/anti-BCMA CAR+ (3K0 (FAS), BCMA CAR+)

TRAC-/B2M-/CD70-/anti-BCMA CAR+ (3K0 (CD70), BCMA CAR+)

TRAC-/B2M-/FAS-/CD70-/anti-BCMA CAR+ (4KO, BCMA CAR+)

Edited cells were enriched for TRAC-/B2M- cells by magnetic depletion of CD3+B2M+cells. Briefly, cells were labeled with anti-CD3 Biotin (Biolegend Cat #300404) anti-02M Biotin (Biolegend Cat #316308) antibodies, each at 0.5 µg per $1\times10^6$ cells in 100 µl volume at 4° C. for 15 min, washed and incubated with Streptavidin labeled magnetic microbeads (Miltenyi Biotech, 130-048-101) for 15 min at 4° C. Cells were resuspended in buffer and passed through LS columns (Miltenyi Biotech, 130-042-401) according to the manufacturer's protocol.

To determine the effect of FAS or CD70 on IL-2/IL-7 driven T cell proliferation, the edited T cells ($1\times10^6$ cells/ml) were cultured in growth medium (X-vivo medium (04-744, Lonza), supplemented with 5% human AB serum (HP1022, Valley Biomedical), 50 ng/ml IL-2 (rhIL-2; 130-097-745, Miltenyi Biotech) and 10 ng/ml IL-7 (rhIL-7; Cellgenix 001410-050) for up to four weeks. At indicated days, the cells were counted and re-seeded in fresh medium at $1.5\times10^6$ cells/ml in appropriate culture dishes.

Figure 2B:
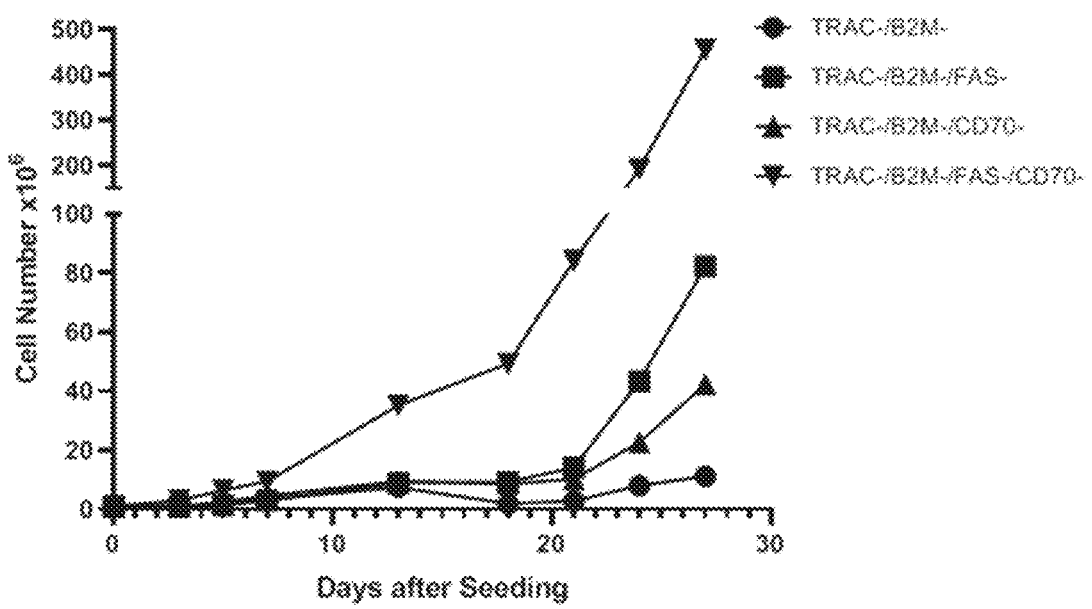

As shown in FIG. 2B, knockout of FAS or CD70 improved IL-2/IL-7 driven proliferation of anti-BCMA CAR T cells in vitro as compared to controls (i.e., anti-BCMA CAR T cells comprising endogenous FAS and CD70). Knockout of both FAS and CD70 showed a synergistic effect on proliferation competence of anti-BCMA CAR T cells as relative to knockout of only FAS or CD70. FIG. 2B.

(iii) FAS KO Rescued Anti-BCMA CAR T Cells from Anti-FAS Antibody Induced Apoptosis The effect of FAS KO on apoptotic cell death of anti-BCMA CAR+ T cells following exposure to anti-FAS antibody was evaluated. Briefly, to activate FAS-FASL signaling pathway, anti-BCMA CAR+ T cells were exposed to anti-FAS antibody (1 µg/ml, BioLegend, Cat No. 305704) for 48 hrs. At the end of the treatment, an aliquot of cells was washed and stained with fluorochrome-conjugated annexin V along with 7-AAD in annexin V binding buffer (BioLegend) for 15 minutes at room temperature. Cells were then washed and resuspended in annexin V binding buffer for analysis by flow cytometry.

Figure 2C:
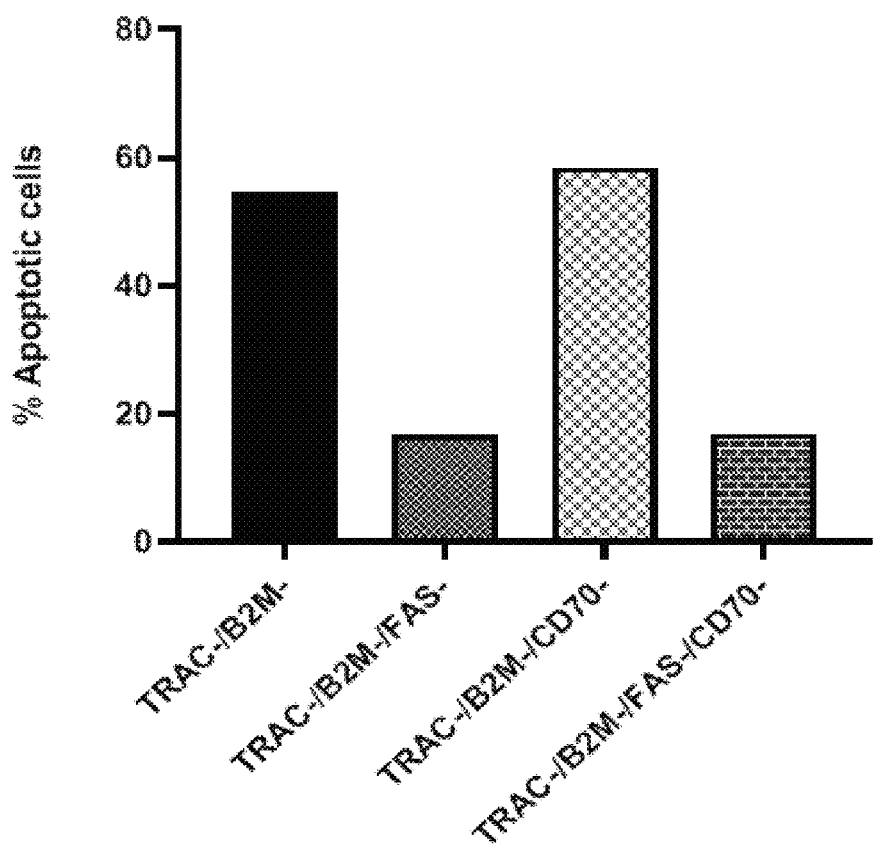

As shown in FIG. 2C, deletion of FAS (FAS KO) rescued anti-BCMA CAR+ T cells from apoptosis induced by anti-FAS antibody, as demonstrated by the decrease in the percentage of apoptotic cells both in the 3KO (TRAC-/B2M-/FAS-) and 4KO (TRAC-/B2M-/FAS-/CD70-) cells.

Example 3

Triple Knockout of CD70, TET2, and FAS Enhanced Cytolytic Activity of Anti-CD19 CAR T Cells Following preparation of edited anti-CD19 CAR T cells, the functional activity of the CAR T cells was verified using a flow cytometry-based cytotoxicity assay. See WO2019/097305 for disclosures of anti-CD19 CAR, the relevant disclosures of which are incorporated by reference for the purpose and subject matter referenced herein. The anti-CD19 CAR T cells (TRAC-/132M-/CD19 CAR+ and TRAC-/132M-/CD70-/TET2-/FAS-/CD19 CAR+) were co-cultured with a CD19-expressing cancer cell line (target cells): Raji (ATCC cc1-86). The target cells were labeled with 5 µM efluor670 (eBiosciences), washed and incubated in co-cultures with the TRAC-/β2M-/anti-CD19 CAR+, or TRAC-/(β2M-/CD70-/TET2-/FAS-/anti-CD19 CAR+ at varying ratios (0.01, 0.05, 0.1, 0.5, 1:1 T cells:target cells). The target cells were seeded at 100,000 cells per well in a 96-well, U-bottom plate. The co-culture was incubated for 48 hours. After incubation, wells were washed and media was replaced with 200 µL of media containing a 1:500 dilution of 5 mg/mL DAPI (Molecular Probes). Twenty five (25) µL of CountBright beads (Life Technologies) were then added to each well and the cell cultures were analyzed for cell viability by flow cytometry (i.e., viable cells being negative for DAPI staining).

Percent cell lysis of the target cells (e.g., Nalm6 or Raji cells) was then determined using the following formula:

Percent cell lysis=(1−((total number of target cells in a test sample)−(total number of target cells in a control sample))×100;

In this formula, a test sample refers to target cells (e.g., Raji cells) co-cultured with (1) TRAC-/β2M-/CD19 CAR+ T cells, or (2) TRAC-/β2M-/CD70-/TET2−/FAS-/anti-CD19 CAR+ cells; and a control sample refers to target cells alone that had not been co-cultured with CAR-T cells.

Figure 3A:
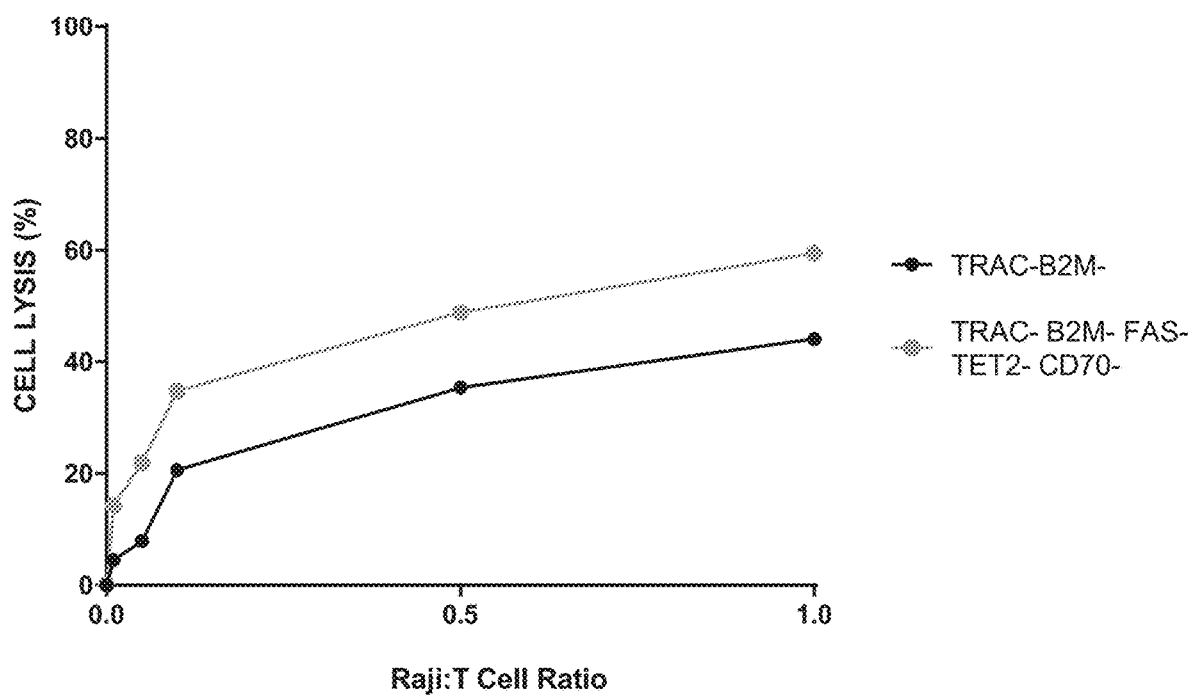
FIGS. 3A and 3B include diagrams showing increased cell killing and cell proliferation in triple knockout (FAS/TET2/CD70 knockouts) T cells.

Disruption of the CD70, TET2 and FAS genes led to enhanced cytolytic activity of the anti-CD19 CAR-T cells against the Raji cell line at low CAR-T to target ratios. FIG. 3A. See WO2019097305 for descriptions of anti-CD19 CAR-T cells (e.g., TC1 cells). The relevant disclosures of this PCT publication is hereby incorporated by reference for the purpose and subject matter referenced herein. The increased activity conferred by CD70, TET2 and FAS loss against the Raji cell line indicates that in challenging tumor environments, particularly when CAR-T to tumor ratios are low, CD70, TET2, and FAS loss may have substantial benefit to the CAR-T cells in eradicating tumor cells.

Generation of T cell Bank and Serial Edits After Cell Bank Expansion

Further, the use of CRISPR/Cas9 gene editing technology is explored for producing a human T cell bank, where the TET2 gene is initially knocked-out, and then is further edited after four weeks in culture. Specifically, the FAS Cell Surface Death Receptor (FAS) gene, and the Cluster of Differentiation 70 (CD70) gene were edited at four weeks by CRISPR/Cas9 gene editing to produce T cells deficient in an additional one or two more genes. Initial editing was conducted in activated primary human T cells and included the electroporation of control T Cells (no RNP) and T cells with a TET2 Cas9/gRNA RNP complex. The nucleofection mix contained the Nucleofector™ Solution, $5 \times 10^6$ cells, 1 μM Cas9, and 5 μM gRNA (as described in Hendel et al., *Nat Biotechnol.* 2015; 33(9):985-989, PMID: 26121415).

Editing conducted after four weeks included re-electroporating the TET2 knockout T cells and the control T cells without RNP. For the generation of double knockout T cells, the TET2 knockout cells were electroporated with an RNP complex, containing Cas9 protein and one of the following sgRNAs: FAS or CD70. For the generation of triple knockout T cells, the TET2 knockout cells were electroporated with two different RNP complexes, each RNA complex containing Cas protein and one of the following sgRNAs: FAS and CD70. The exemplary gRNAs for use in gene editing of the TET2, FAS, and CD70 genes are provided in Table 10 below:

TABLE 10

TET2 FAS CD70 gRNA Sequences
gRNA Sequences

| Name | Unmodified Sequence | Modified Sequence |
|---|---|---|
| TET2 sgRNA (TET2 exon 4_BC4) | cauuaggaccugcuccuag aguuuuagagcuagaaaua gcaaguuaaaauaaggcua guccguuaucaacuugaaa aaguggcaccgagucggug cuuuu (SEQ ID NO: 12) | c*a*u*uaggaccugcuccua gaguuuuagagcuagaaaug caaguuaaaauaaggcuaguc cguuaucaacuugaaaaagug gcaccgagucggugcu*u*u* u (SEQ ID NO: 13) |
| FAS sgRNA | acugcgugcccugccaaga aguuuuagagcuagaaaua gcaaguuaaaauaaggcua guccguuaucaacuugaaa aaguggcaccgagucggug cuuuu (SEQ ID NO: 83) | a*c*u*gcgugcccugccaag aaguuuuagagcuagaaaug caaguuaaaauaaggcuaguc cguuaucaacuugaaaaagug gcaccgagucggugcu*u*u* u (SEQ ID NO: 84) |
| CD70 sgRNA | GCUUUGGUCCCAUUGGUCGCguu uuagagcuagaaauagcaaguua aaauaaggcuaguccguuaucaa cuugaaaaaguggcaccgagucg gugcUUUU (SEQ ID NO: 44) | G*C*U*UUGGUCCCAUUGGUCGCgu uuuagagcuagaaauagcaaguuaa aauaaggcuaguccguuaucaacuu gaaaaaguggcaccgagucggugcU *U*U*U (SEQ ID NO: 45) |

*2'-O-methyl phosphorothioate residue

To assess whether further editing the cell bank affects cell expansion, cell numbers were enumerated among, single, double, triple gene edited T cells (unedited T cells were used as a control) over a seven-week period of post editing. $1 \times 10^6$ cells were generated and plated for each genotype of T cells. After electroporation, cell expansion was assessed as by counting viable cells once a week for a seven-week period. Cells were maintained at $1 \times 10^6$ cells per mL in complete media.

Figure 3B:
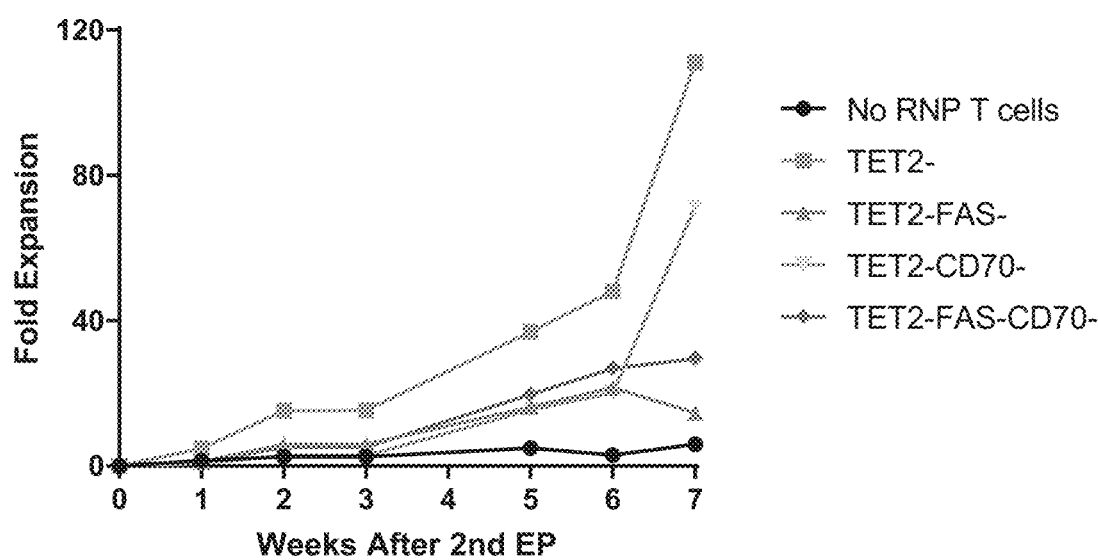

As shown in FIG. 3B, cell proliferation (expansion) continued after the post second electroporation in the edited cell bank conditions. Cell proliferation was observed among the single TET2 (cell bank), double (TET2-/CD70-) or (TET2-/FAS-), or triple (TET2-/CD70-/FAS), knockout T cells, as indicated by the number of viable cells. These data suggest that serial gene editing to a TET2-T cell bank does not impact T cell health as measured by T cell proliferation after a period of recovery.

Example 4

In vivo effect of TET2, FAS and CD70 KO on Allogeneic CAR T Cells in the Intravenous Disseminated Nalm-6 Human Acute Lymphoblastic Leukemia Tumor Xenograft Model A disseminated mouse model was utilized to further assess the in vivo efficacy of allogeneic CAR T cells lacking B2M and TRAC, as well as TET2, FAS and/or CD70. The intravenous disseminated model (disseminated model) using a CD19+ B-ALL derived Nalm-6 Human Acute Lymphoblastic Leukemia tumor cell line in NOG mice was used to demonstrate the efficacy of anti-CD19/TRAC⁻B2M⁻ CAR T cells (anti-CD19 CAR T cells) with or without the additional gene edits disclosed herein (e.g., TET2, FAS and/or CD70). The anti-CD19 CAR T cells were made as described in Example 3. See also WO2019/097305.

Efficacy of the anti-CD19 CART cells was evaluated in the disseminated model using methods employed by Translations Drug Development, LLC (Scottsdale, AZ) and described herein. In brief, 40, 5-8 week old female CIEA NOG (NOD.Cg-Prkdc$^{scid}$I12rg$^{tm1Sug}$/JicTac) mice were individually housed in ventilated microisolator cages, maintained under pathogen-free conditions, 5-7 days prior to the start of the study. At the start of the study, the mice were divided into 8 treatment groups as shown in Table 11. The mice were inoculated with Nalm6-Fluc-GFP (Nalm6-Fluc-Neo/eGFP-Puro) cells intravenously to model disseminated disease. On Day 1, all mice received an intravenous injection of $0.5 \times 10^6$ Nalm6 cells/mouse. On Day 4, Groups 2-8 received an intravenous injection of CAR T cells (4×10⁶ CAR+ cells/mouse) as indicated in Table 11.

TABLE 11

Treatment groups

| Group | Nalm6 tumor cells 0.5 × 10⁶ cells/mouse | CAR T cells (i.v.) 4 × 10⁶ cells/mouse | N |
|---|---|---|---|
| 1 | X | NA | 5 |
| 2 | X | anti-CD19 CAR/TRAC−/B2M− | 5 |
| 3 | X | anti-CD19 CAR/TRAC−/B2M−/CD70− | 5 |
| 4 | X | anti-CD19 CAR/TRAC−/B2M−/TET2− | 5 |
| 5 | X | anti-CD19 CAR/TRAC−/B2M−/FAS− | 5 |
| 6 | X | anti-CD19 CAR/TRAC−/B2M−/TET2−/CD70− | 5 |
| 7 | X | anti-CD19 CAR/TRAC−/B2M−/FAS−/CD70− | 5 |
| 8 | X | anti-CD19 CAR/TRAC−/B2M−/FAS−/TET2−/CD70− | 5 |

During the course of the study, the mice were monitored daily and body weight was measured two times weekly. Blood samples (0.1 ml/mouse) were collected from all mice by submandibular bleed at days 2, 7, 14, 21, 42 and 50 to assess CAR T cell expansion over the course of the study. Bioluminescence (BLI; total ROI, photon/s) was measured twice weekly beginning on Day 4 of the study. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;

Tumors that inhibit normal physiological function such as eating, drinking, mobility and ability to urinate and or defecate;

Prolonged, excessive diarrhea leading to excessive weight loss (>20%); or

Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

(i) In Vivo Survival Rate

Mice in groups receiving TRAC⁻/B2M⁻CAR T cells with an additional TET2 knockout, either alone or in combination with CD70 and/or FAS (Groups 4, 6 and 8), exhibited an increase in survival relative to mice in both the untreated (Group 1) and those treated with TRAC⁻/B2M⁻ allogeneic anti-CD19 CAR T cells with a wild-type TET2 allele (Group 2) and did not succumb to Nalm6 leukemia even out to 153 days after treatment. While CD70 loss (Group 3; anti-CD19 CAR/TRAC⁻/B2M⁻/CD70⁻) did not increase survival relative to Group 2 mice, the addition of the TET2 knock-out prolonged survival of mice in Group 6 (anti-CD19 CAR/TRAC⁻/B2M⁻/TET2⁻/CD70⁻) and group 8 (anti-CD19 CAR/TRAC⁻/B2M⁻/FAS⁻/TET2⁻/CD70⁻) as compared to the Group 2 mice. See Table 12 below.

TABLE 12

Survival Days of Mice Treated by CAR-T Cells

| Group | CART cells (i.v.) 4 × 10⁶ cells/mouse | Median Survival (Days) |
|---|---|---|
| 1 | NA | 24 |
| 2 | anti-CD19 CAR/TRAC−/B2M− | 102 |
| 3 | anti-CD19 CAR/TRAC−/B2M−/CD70− | 46 |
| 4 | anti-CD19 CAR/TRAC−/B2M−/TET2− | >153 |
| 5 | anti-CD19 CAR/TRAC−/B2M−/FAS− | >153 |
| 6 | anti-CD19 CAR/TRAC−/B2M−/TET2−/CD70− | >153 |
| 7 | anti-CD19 CAR/TRAC−/B2M−/FAS−/CD70− | 55 |
| 8 | anti-CD19 CAR/TRAC−/B2M−/FAS−/TET2−/CD70− | 137 |

Figure 5A:
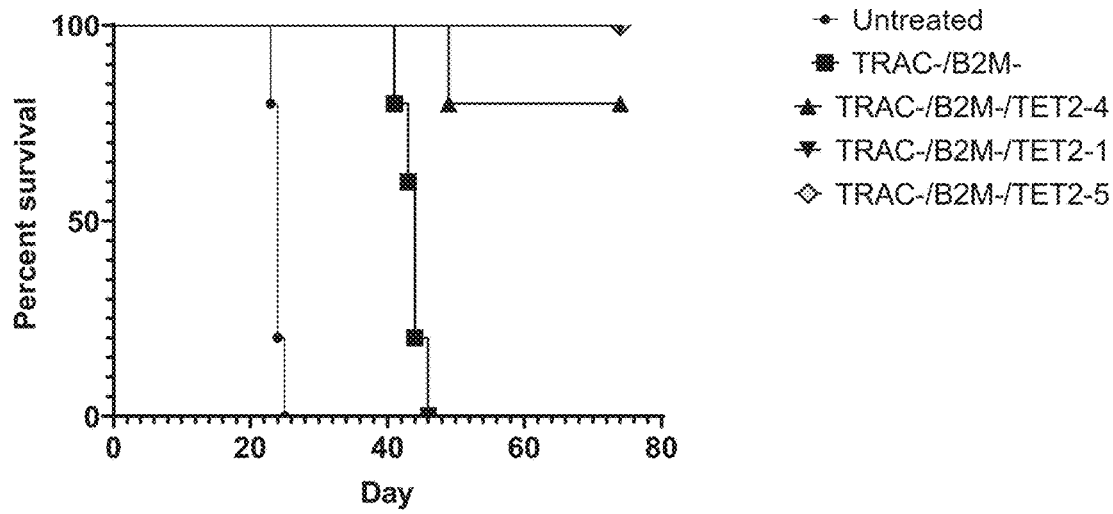
FIGS. 5A-5B include graphs showing increase survival and tumor inhibition by CAR-T cells in mice with acute lymphoblastic leukemia.
Figure 5B:
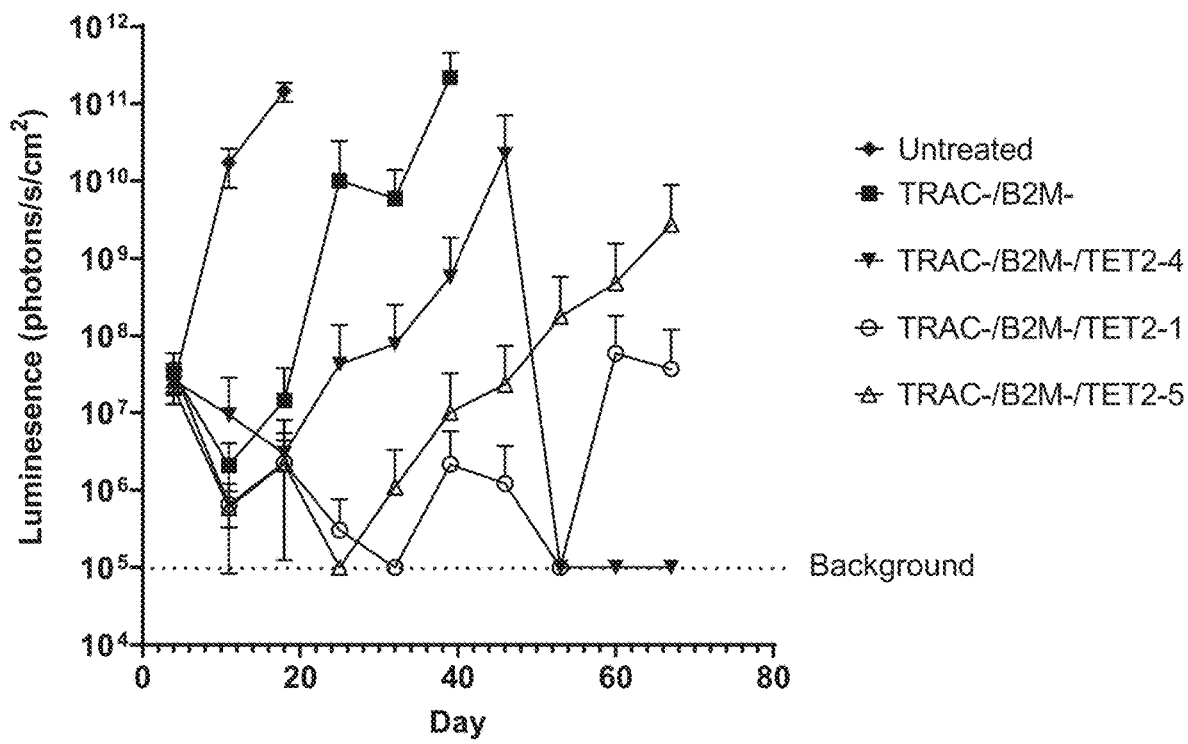

To assess if the effects of the TET2 KO observed in allogeneic anti-CD19 CAR+/TRAC−/B2M− T cells were specific to sgRNA TET2 exon4 BG4, a separate lot of cells was prepared from a different healthy donor and tested in the Nalm6/in vivo model as above. Mice treated with 4×10⁶CAR+ cells that had disruption of the TET2 locus with either of the following sgRNAs (TET2 exon6_BG5, TET2 exon4_BG4 or TET2 exon3_T1) all prolonged survival of mice longer than mice receiving TRAC−/B2M−/CAR+ T cells (FIG. 5A; All TET2−groups showed statistically significant survival vs TRAC−/B2M−/CAR+ T cells (p=0.0021); Log-Rank test) and showed reduced Nalm6-luciferase activity over time (FIG. 5B). Thus, Tet2 improved CAR T efficacy in the Nalm6 disseminated mouse model.

Taken together, TET2 knockout leads to marked cell expansion, leading to enhancement of the function of CAR T cells in an in vivo model of CD19⁺ malignancy. Furthermore, TET2 KO allows CAR-T cells to carry edits in other genes that may have additional benefits to the cells (e.g., anti-apoptosis/anti-senescence) but do not prolong survival in this leukemia model on their own.

(ii) CAR T Cell Expansion In Vivo

CAR T cell expansion was assessed by measuring the CAR copy number by ddPCR of DNA isolated from blood samples collected throughout the study as described above.

DNA was isolated from mouse tissue using the Qiagen Dneasy blood and tissue kit (Qiagen, Venlo, Netherlands). Total mass of nucleic acid from RBC-lysed samples was quantitated using either Nanodrop (Thermo Fisher Scientific) or DropSense96 (trinean, Gentbrugge, Belgium) machines. Primers and 6-carboxyfluorescein (FAM)-labeled probe sets (provided in Table 12 below) were designed to quantitate the levels of the integrated CAR construct into the human TRAC locus by droplet digital PCR (ddPCR). ddPCR was performed using the Bio-Rad Automated Droplet Generator, Bio-Rad T100 Thermal Cycler, and Bio-Rad QX200 Droplet Reader machine(s) (Bio-rad Laboratories, Hercules, CA). QuantaSoft Version 1.7.4.0917 (Bio-rad Laboratories) software was used to calculate the absolute number of integrated CAR copies per sample. Finally, the number of detected CAR alleles was divided by the input total DNA amount to compute the absolute number of CAR copies per mass of input sample. The ddPCR assay detects the number of copies of integrated CAR transgene per mass of genomic DNA (gDNA) by amplifying an 866 bp amplicon spanning endogenous TRAC sequence and the CAR expression cassette promoter (EF-1a). In brief, qualification of the assay yielded linear data ($R^2$>0.95) within the range tested (2 to 300,000 copies per µg of gDNA) as well as generated a % relative error (% RE) and % coefficient of variation (% CV) within normal ranges (% RE≤100% and % CV≤20%) for conditions ≥LLOQ. The LLOD and LLOQ were calculated based on the available data and the LLOD was set to 5 copies per 0.2 μg of gDNA and the LLOQ was set to 40 copies per 0.2 μg.

TABLE 13

Primers and probes used for ddPCR CAR primers and probe

| | |
|---|---|
| Anti-CD19 CAR-20-30_dd_1 Forward | GGCACCATATTCATTTTGC AGGTGAA (SEQ ID NO: 151) |
| Anti-CD19 CAR-20-30_dd_1 Reverse | ATGTGCGCTCTGCCCACTG ACGGGC (SEQ ID NO: 152) |
| Anti-CD19 CAR-20-30_dd_1 Probe (FAM) | AGACATGAGGTCTATGGAC TTCAGGCTCC (SEQ ID NO: 153) |

Figure 4:
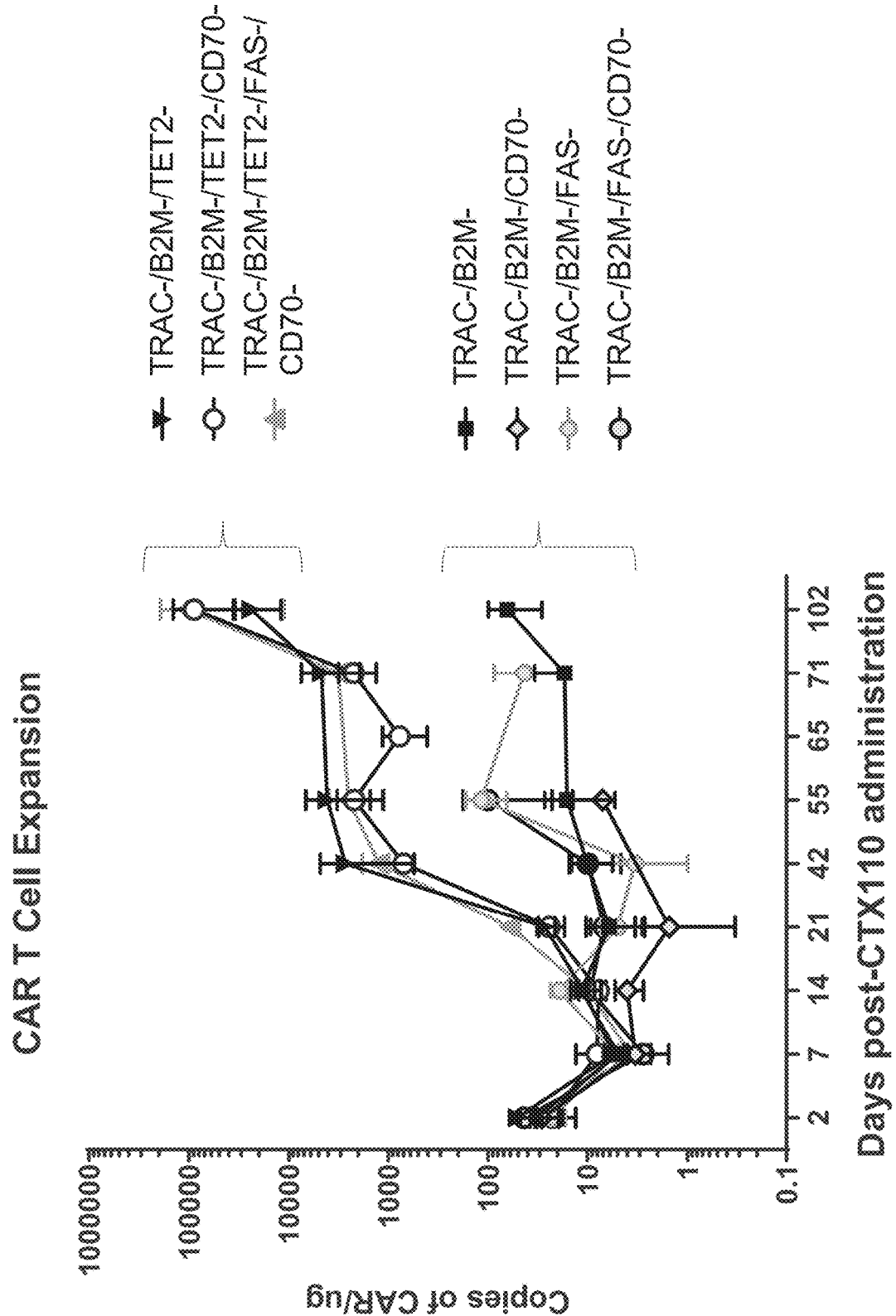
FIG. 4 includes a graph showing expansion of CAR-T cells in mice with acute lymphoblastic leukemia. The mice were treated with anti-CD19 CAR-T cells having disrupted TRAC and B2M genes, and optionally in combination with disrupted TET2, CD70, and/or FAS as indicated.

These analysis demonstrate that the addition of a TET2 KO to allogeneic CAR T cells (TRAC⁻/B2M⁻) allowed the T cells to expand to larger levels in the blood of treated mice (e.g., Groups 4, 6, and 8) compared to groups treated with the allogeneic CAR T cells without a TET2 KO (e.g., Groups 2, 3, 5, and 7) (FIG. 4). This expansion was apparent at day 21 of the study and passed day 100. FAS KO also appeared to give a more modest expansion to CAR T cells apparent at day 50 (e.g., Group 5 or 7 vs. Group 2) (FIG. 4).

In sum, all groups with loss of TET2 had expanded CAR-T cells in the peripheral blood and groups with loss of FAS displayed increased levels at relatively later time points.

Example 5

Figure 6A:
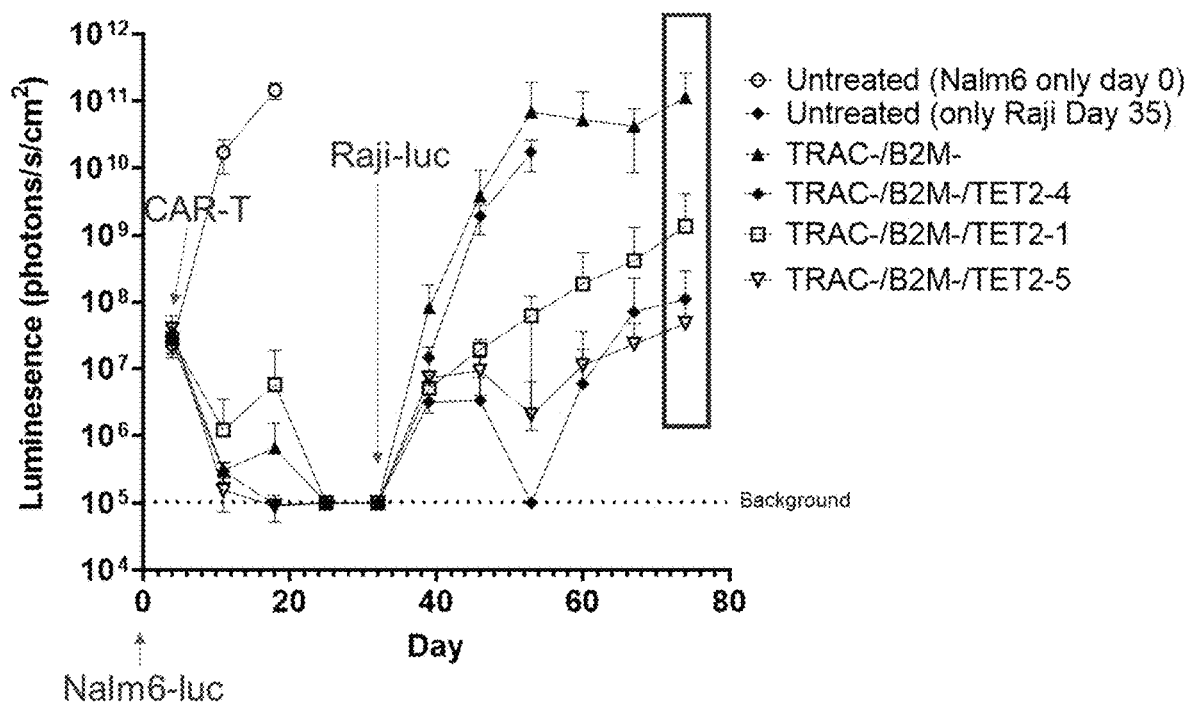
FIGS. 6A-6E include graphs showing a protective effect of CAR T cells containing a TET2 KO when exposed to a tumor re-challenge.

Knock-Out of TET2 Increases the Persistence of Functional CAR-T Cells in Liquid and Solid Tumor Models To assess the mechanism of how TET2 KO increases CAR-T potency, the effects of TET2 disruption on CAR T cells persistence was examined in several re challenge models. In a re-challenge model of CD19+ malignancy NOG mice first received Nalm6-luciferase cells and were dosed with CAR-T cells as described above. Mice were dosed with $8\times10^6$ CAR+ CD19 CAR-T cells that were all TRAC-/B2M-along with groups that had an additional disruption of TET2 induced using one of three gRNAs: TET2 exon4_BG4, TET2 exon3_T1, of TET2 exon6_BG5. While untreated mice had quickly succumb to leukemia all CAR-T cell groups cleared the initial Nalm6-luciferease leukemia within a 30 day period (FIG. 6A). At Day 35 of the study all mice received a second dose of cancer cells, using a more aggressive cancer cell line. The CD19+ Burkitt lymphoma derived Raji-luciferase cell line was injected into mice at $0.5\times10^6$ cells per mouse intravenously (i.v.). Naïve mice (mice that had not received Nalm-luc cells) quickly succumb to Raji lymphomas. However, mice that had previously cleared Nalm6 tumors after receiving the TRAC-/B2M-/TET2-cells better controlled the second tumor than mice that had received just TRAC-/B2M-CAR T cells (FIG. 6A). These data provide evidence that TET2 disruption allows for the continued persistence of functional CAR-T cells. This effect is independent of the TET2 genomic segment disrupted as cells edited with several distinct sgRNAs gave similar results.

Figure 6B:
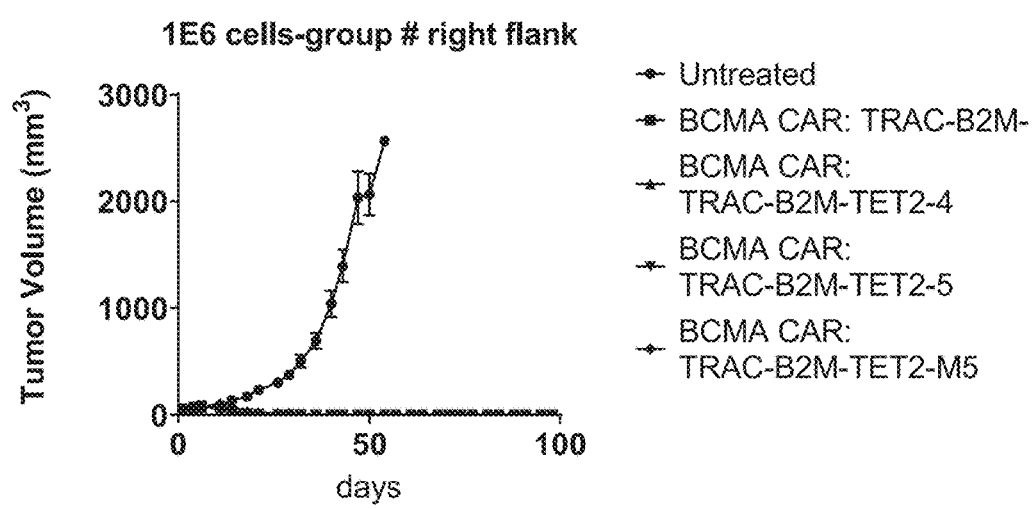
Figure 6C:
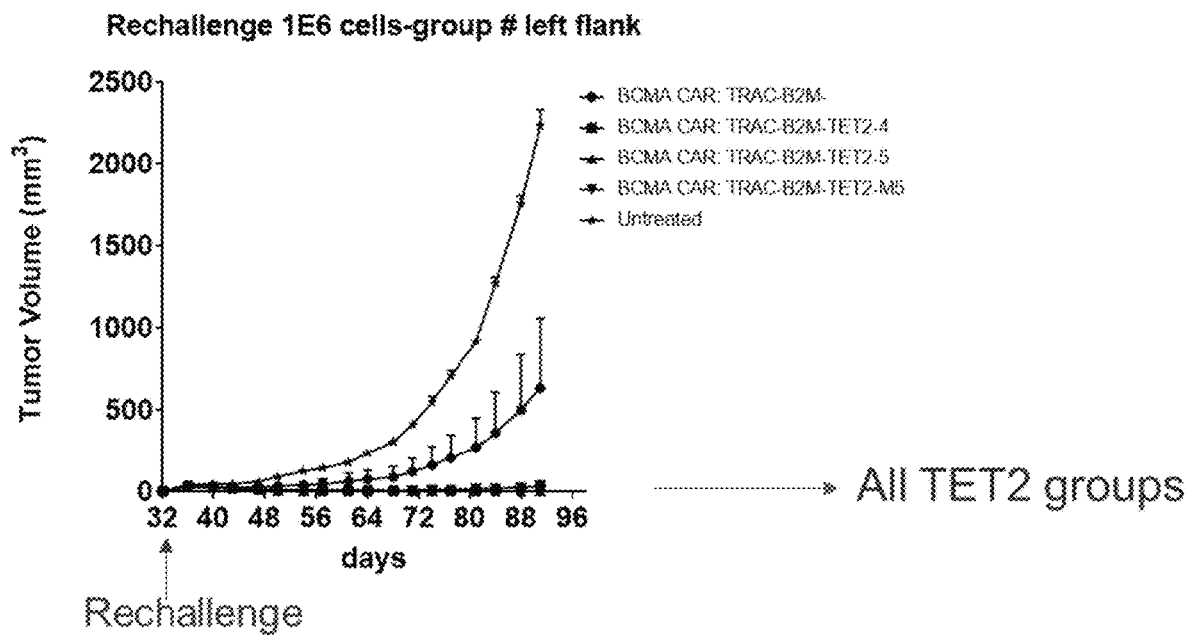

To assess the ability of TET2 KO to increase the persistence of CAR-T cells in a different liquid tumor model (multiple myeloma) in the context of a different CAR construct (anti-BCMA CAR) BCMA targeting CAR-T cells were made from a healthy donor. Anti-BCMA CAR T Cells were made as previously described. Groups of CAR-T cells were made that were TRAC-/B2M- and TRAC-/B2M-/TET2-(using either TET2 exon4_BG4, TET2 exon6_BG5 or TET2 exon5_T1 sgRNA). NOG mice were initially inoculated subcutaneously in their right flanks with $1\times10^7$ multiple myeloma derived RPMI-8226 cells. After 9 days, when tumors were palpable, $1\times10^6$ CAR+ cells were injected i.v. While untreated mice quickly had succumb to tumor endpoint (2000 mm3) both TRAC-/B2M- and TRAC-/B2M-/TET2-groups efficiently cleared the primary RPMI-8226 tumors (FIG. 6B). On day 32 of the study mice previously treated with CAR+ T cells were subjected to a tumor re-challenge by injecting $1\times10^7$ fresh RPMI-8226 cells into the left flank of mice. A new group of naïve mice were injecting $1\times10^7$ fresh RPMI-8226 cells into the left flank (untreated group). While TRAC-/B2M-BCMA-CAR-T cells could control of the re-challenge to some extent, TRAC-/B2M-/TET2-BCMA-CAR-T cells quickly eliminated these new tumor cells (FIG. 6C). Taken together TET2 disruption allows CAR-T cells to persist longer in aggressive re-challenge models in multiple liquid tumor models. This effect multiple CAR T cells targeting different cancer antigens.

Figure 6D:
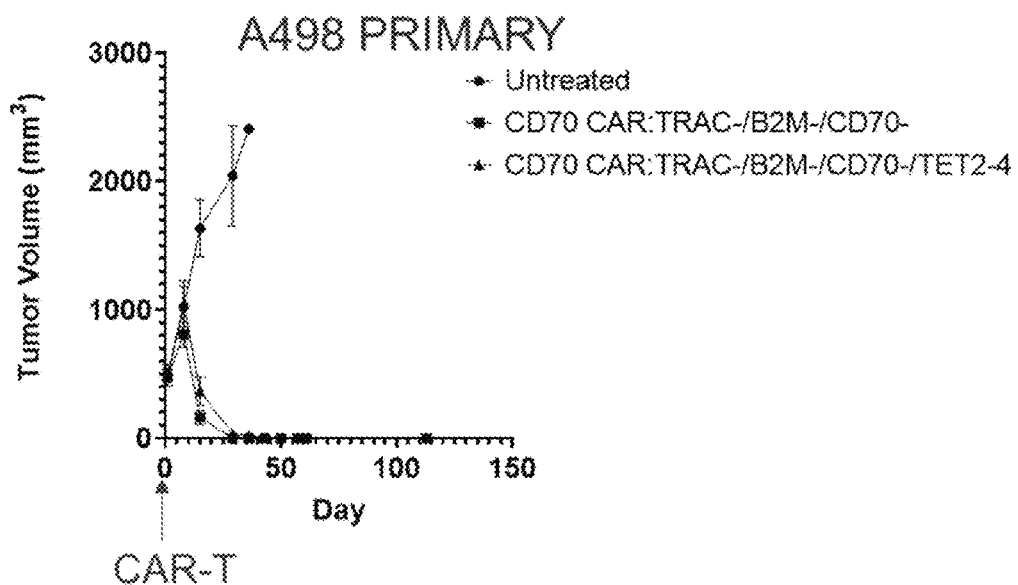
Figure 6E:
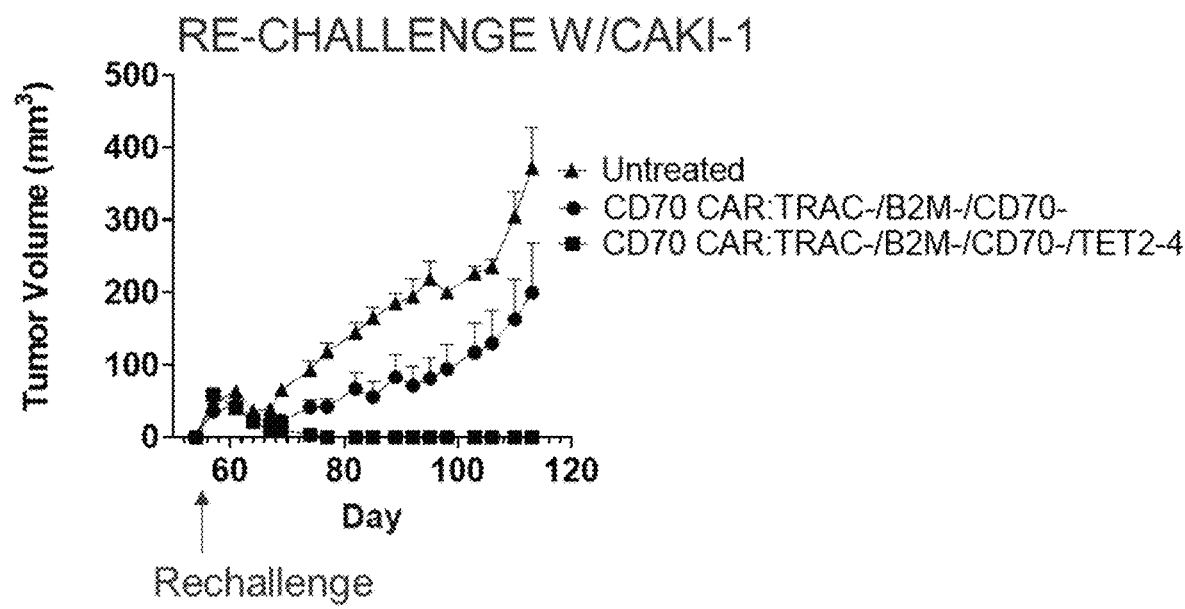

To assess the ability of TET2 loss to increase the persistence of CAR-T cells in solid tumors CD70 targeting CAR T cells (anti-CD70 CAR T cells) were made from a healthy donor. Groups of CAR-T cells were made that were TRAC-/B2M-/CD70- and TRAC-/B2M-/CD70-/TET2-(e.g.: TET2 exon4) BG4 sgRNA). NOG mice were initially inoculated subcutaneously in their right flanks with $5\times10^6$ renal cell carcinoma (RCC) derived A498 cells. When tumors reached 500 mm³ $13\times10^7$ CAR-T cells were injected i.v.. While untreated mice quickly had succumb to tumor endpoint (2000 mm³) both TRAC-/B2M-/CD70- and TRAC-/B2M-/CD70-/TET2-efficiently cleared the primary A498 tumors (FIG. 6D). On day 54 of the study mice were subjected to a tumor re-challenge by injecting $5\times10^6$ RCC-derived Caki-1 cells into the left flank of mice. A new group of naïve mice were injecting $1\times10^7$ fresh RPMI-8226 cells into the left flank (untreated group). While TRAC-/B2M-/CD70-/CD70-/CAR-T cells showed modest control of the Caki-1 tumors TRAC-/B2M-/CD70-/TET2-/CD70-/CAR-T cells quickly eliminated these tumor cells (FIG. 6E). Taken together TET2 disruption allows CAR-T cells to persist longer in aggressive re-challenge models of both liquid and solid tumors.

Example 6

TET2 Deficient CAR-T Cells Depend on Cytokines for Growth

Figure 7:
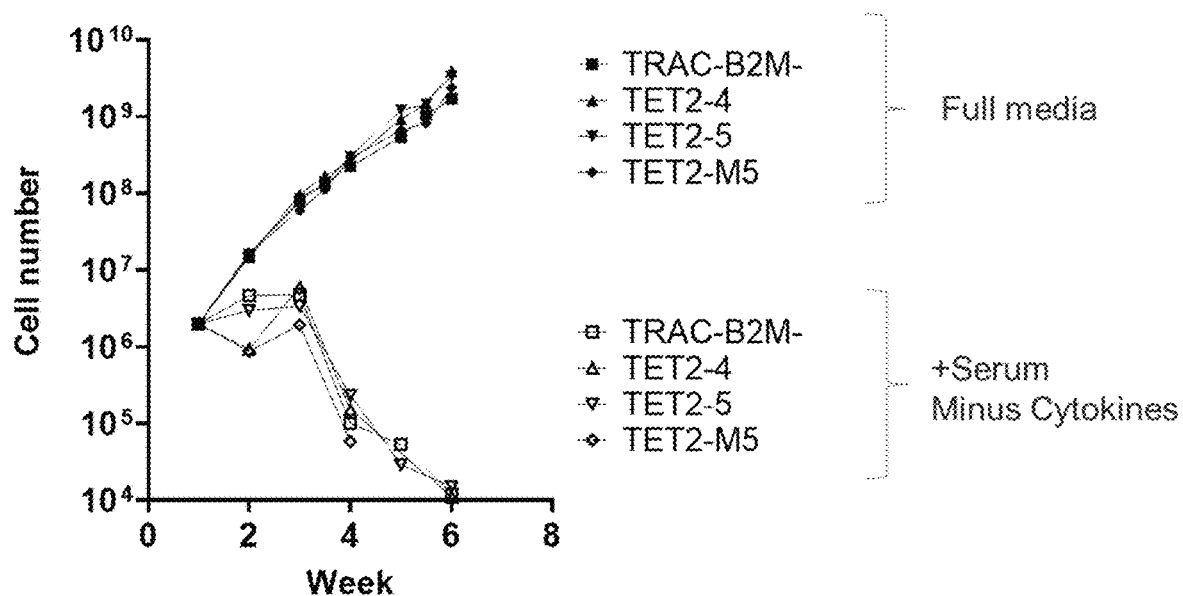
FIG. 7 includes a graph showing cytokine independent growth of TRAC-/B2M-/TET2–CAR T cells.

To assess the tumorigenic potential of CAR-T cells that lack TET2, anti-CD19 CAR T cells were produced that were TRAC-/B2M- and either wild type for TET2 or had a TET2 disruption (TET2 disruption was generating using either TET2 exon4_BG4, TET2 exon6_BG5, TET2-exon5_T1). Cells were then used to assess for the ability of genome edited cells to display growth factor and/or cytokine independent growth in culture. 2×10⁶ cells were placed in either full T cell media (containing 5% human serum+ IL2 and IL7) or in media containing serum but lacking IL-2 and IL-7. Cells were then counted weekly using trypan blue and a Countess automated cell counter (Thermo Fisher Scientific). While all groups of cells could grow in media containing serum and cytokines, no outgrowths were detected over a 6 week period from any of the groups. FIG. 7. These data demonstrate that TET2 disruption does not lead to direct oncogenic transformation of human peripheral blood derived T cells as these cells continue to depend on cytokines for their growth.

capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions indicating repair following CRISPR/Cas9-mediated gene editing.

The results are provided in Table 14 below.

TABLE 14

On and Off Target Results by Hybrid Capture

| Guide | gRNA target sequence + (PAM) | Number of predicted off target sites tested | On-target mean editing hyb cap$^a$ | Effect of editing on Tet2 protein expression | Detected off-targets |
|---|---|---|---|---|---|
| TET2-exon3-T1 | GATTCCGCTTGGTGAAAACG (AGG) (SEQ ID NO: 128) | 36 | 89.0% | KO | NO |
| TET2-exon3-12 | CAGGACTCACACGACTATTC (TGG) (SEQ ID NO: 130) | 57 | 87.7% | Reduced | NO |
| TET2-exon3-13 | TTCCGCTTGGTGAAAACGAG (GGG) (SEQ ID NO: 132) | 54 | 80.0% | KO/truncation | NO |
| TET2-exon6-BG5 | ACGGCACGCTCACCAATCGC (CGG) (SEQ ID NO: 31) | 6 | 93.8% | KO/truncation | Yes, one: intronic to PRKAR1B, a regulatory subunit of PKA |
| TET2-exon5-T1 | GGGATGTCCTATTGCTAAGT (GGG) (SEQ ID NO: 29) | 59 | 93.0% | KO/truncation | Yes, one: exonic to TET1 with 3 mismatches relative to guide |
| TET2-exon5-12 | AGGGATGTCCTATTGCTAAG (TGG) (SEQ ID NO: 30) | 103 | 96.0% | KO | Yes, one |
| TET2-exon4-BG4 | CATTAGGACCTGCTCCTAGA (TGG) (SEQ ID NO: 28) | 90 | 94.9% | KO | Yes, two |

$^a$Average across donors 1 and 2.

Example 7

On-Target and Off-Target Editing of TET-2 Guide RNAs

On-target and off-target editing efficiencies of various TET2–targeting gRNAs were examined following the method disclosed in Example 1 above. Briefly, activated T cells derived from primary human PBMC cells were transfected (electroporated) with a ribonucleoprotein particle (RNP) containing Cas9 nuclease and a synthetic modified sgRNA targeting the TET2 gene (sequences in Table 3 above) or controls (no Cas9, no gRNA). Six (6) days post transfection, cells were immunoblotted to assess the effect of on-target TET2 editing on protein expression.

For genomic on- and off-target assessment, the same electroporation methods were used to generate two cell populations of edited cells from two different donor T cells (termed 1 and 2).

Cells were gene edited with each of the seven guides listed in Tables 3 and 14, and then collected six (6) days post transfection. These samples were analyzed with hybrid Analysis of On-Target Indel Profiles in T Cells The data used to quantify off-target editing were also used to quantify and summarize the most frequent on-target indels for all TET2 guides listed in Table 14. This data was generated from hybrid capture of the TET2 locus combined with next-generation sequencing in two donors (termed Donor 1 and Donor 2).

Following gene editing, hybrid capture analysis of the TET2 locus in a population of T cells following CRISPR/Cas9 gene editing to produce TET2-T cells results in specific indel frequencies and edited gene sequences at the TET2 locus (Tables 15-21; deletions as dashes and insertions in bold).

For the purposes of individual sequence quantification from hybrid capture data, sequence reads aligning across the TET2 on-target site, 20 bp upstream and downstream of the cut site, were selected and considered for indel sequence quantification. From the selected reads, the sequence within 10 bp upstream and downstream of each putative cut site ('-3bp upstream of the PAM (Jinek, et al., Science 2012) was quantified as a representative region of on-target non-homologous end joining (NHEJ) editing. The data on these on-target gene edited sequences is presented in the tables below, with the frequencies of these sequences representing the percent of all sequences spanning the on-target site within 20 bp upstream and downstream of each cut site. The indels for each guide are shown relative to an on-target reference sequence in Tables 15-21. The reference sequence is centered on the cleavage site with 10 bp in either direction, ending 4 by 3' of the PAM.

TABLE 15

On-Target Gene Edited Sequences >1% Frequency in At Least One Gene Edited T Cell Donor for the TET2-Exon3-T1 gRNA.
Reference on-target sequence[a]: <u>CTTGGTGAAAACG</u>(AGG)GGCC
(SEQ ID NO: 154)

| SEQ ID NO: | Gene Edited Sequence[b] | Reference Sequence[c] (SEQ ID NO: 154) | Donor 1 (%) | Donor 2 (%) | Mean (%) | Std. Dev. (%) |
|---|---|---|---|---|---|---|
| 155 | CTTGGTGAAA-CGAGGGGCC | CTTGGTGAAAACGAGGGGCC | 27.7 | 25.6 | 26.7 | 1.5 |
| 156 | CTTGGTGAAAAaCGAGGGGCC | CTTGGTGAAAA-CGAGGGGCC | 13.7 | 15.5 | 14.6 | 1.3 |
| 157 | CTTGGTGAA--CGAGGGGCC | CTTGGTGAAAACGAGGGGCC | 4.8 | 4.2 | 4.5 | 0.4 |
| 158 | CTTGGTGA------GGGGCC | CTTGGTGAAAACGAGGGGCC | 4.8 | 3.7 | 4.2 | 0.8 |
|  | -------------------- | CTTGGTGAAAACGAGGGGCC | 2.9 | 3.2 | 3.0 | 0.2 |
|  | CTTGG-----------GGCC | CTTGGTGAAAACGAGGGGCC | 2.9 | 2.1 | 2.5 | 0.6 |
|  | -------------AGGGGCC | CTTGGTGAAAACGAGGGGCC | 2.4 | 2.4 | 2.4 | 0.0 |
|  | CTTGG-------------CC | CTTGGTGAAAACGAGGGGCC | 1.8 | 1.6 | 1.7 | 0.1 |
|  | C------------------C | CTTGGTGAAAACGAGGGGCC | 1.2 | 1.4 | 1.3 | 0.1 |
|  | CTTGG------------GCC | CTTGGTGAAAACGAGGGGCC | 1.2 | 1.6 | 1.4 | 0.3 |
|  | CTT----------------- | CTTGGTGAAAACGAGGGGCC | 1.2 | 1.7 | 1.4 | 0.3 |
|  | -----------------GCC | CTTGGTGAAAACGAGGGGCC | 0.9 | 1.2 | 1.0 | 0.2 |
|  | ------------------CC | CTTGGTGAAAACGAGGGGCC | 0.6 | 1.2 | 0.9 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 16

On-Target Gene Edited Sequences >1% Frequency in At Least One Gene Edited T Cell Donor for the TET2-exon3-T2 gRNA.
Reference on-target sequence[a]: <u>CACACGACTATTC</u>(TGG)CTTC
(SEQ ID NO: 159)

| SEQ ID NO: | Gene Edited Sequence[b] | Reference Sequence[c] (SEQ ID NO: 159) | Donor 1 (%) | Donor 2 (%) | Mean (%) | Std. Dev. (%) |
|---|---|---|---|---|---|---|
| 160 | CACACGACT-----GGCTTC | CACACGACTATTCTGGCTTC | 14.1 | 14.7 | 14.4 | 0.4 |
| 161 | CACACGACT---------TC | CACACGACTATTCTGGCTTC | 11.5 | 11.8 | 11.6 | 0.2 |
| 162 | CACACGACT--TCTGGCTTC | CACACGACTATTCTGGCTTC | 5.1 | 3.4 | 4.2 | 1.2 |
| 163 | CACACGACTAT-CTGGCTTC | CACACGACTATTCTGGCTTC | 2.9 | 3.7 | 3.3 | 0.6 |
| 164 | CACACGACTAaTTCTGGCTTC | CACACGACTA-TTCTGGCTTC | 4.1 | 2.5 | 3.3 | 1.1 |
| 165 | CACACGACTATTtCTGGCTTC | CACACGACTATT-CTGGCTTC | 3 | 3.4 | 3.2 | 0.3 |
| 166 | CACACGACT-TTCTGGCTTC | CACACGACTATTCTGGCTTC | 3.4 | 2.2 | 2.8 | 0.8 |
|  | CACACGACT----------- | CACACGACTATTCTGGCTTC | 2.9 | 2.2 | 2.6 | 0.5 |
|  | -------------------- | CACACGACTATTCTGGCTTC | 2.4 | 2.7 | 2.6 | 0.2 |
|  | ----------------CTTC | CACACGACTATTCTGGCTTC | 1.5 | 1.6 | 1.6 | 0.1 |
|  | CACAC--------------- | CACACGACTATTCTGGCTTC | 1.6 | 1.5 | 1.6 | 0.1 |

TABLE 16-continued

On-Target Gene Edited Sequences >1% Frequency in At Least One Gene Edited T Cell Donor for the TET2-exon3-T2 gRNA.
Reference on-target sequence[a]: CACACGACTATTC(TGG)CTTC
(SEQ ID NO: 159)

| SEQ ID NO: | Gene Edited Sequence[b] | Reference Sequence[c] (SEQ ID NO: 159) | Donor 1 (%) | Donor 2 (%) | Mean (%) | Std. Dev. (%) |
|---|---|---|---|---|---|---|
| 167 | CACACG----TTCTGGCTTC | CACACGACTATTCTGGCTTC | 1.8 | 1 | 1.4 | 0.6 |
|  | CAC----------------- | CACACGACTATTCTGGCTTC | 1.3 | 1.4 | 1.4 | 0.1 |
|  | ----------TTCTGGCTTC | CACACGACTATTCTGGCTTC | 1.5 | 1.4 | 1.4 | 0.1 |
|  | C------------------- | CACACGACTATTCTGGCTTC | 1.4 | 1 | 1.2 | 0.3 |
| 168 | CACAC--------TGGCTTC | CACACGACTATTCTGGCTTC | 1.1 | 1.2 | 1.2 | 0.1 |
|  | CACACG---------GCTTC | CACACGACTATTCTGGCTTC | 1.2 | 1 | 1.1 | 0.1 |
|  | ------------------TC | CACACGACTATTCTGGCTTC | 1.1 | 1.1 | 1.1 | 0 |
| 169 | CACACGACTA--CTGGCTTC | CACACGACTATTCTGGCTTC | 1.1 | 1 | 1 | 0.1 |
|  | --------------GGCTTC | CACACGACTATTCTGGCTTC | 1.2 | 0.7 | 1 | 0.4 |
|  | CACACGAC------------ | CACACGACTATTCTGGCTTC | 0.7 | 1.1 | 0.9 | 0.3 |
| 170 | CACACGACT---CTGGCTTC | CACACGACTATTCTGGCTTC | 1.2 | 0.6 | 0.9 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 17

On-Target Gene Edited Sequences >1% Frequency in At Least One Gene Edited T Cell Donor for the TET2-exon3-T3 gRNA.
Reference on-target sequence[a]: TGGTGAAAACGAG(GGG)CCTT
(SEQ ID NO: 171)

| SEQ ID NO: | Gene Edited Sequence[b] | Reference Sequence[c] (SEQ ID NO: 171) | Donor 1 (%) | Donor 2 (%) | Mean (%) | Std. Dev. (%) |
|---|---|---|---|---|---|---|
| 172 | TGGTGAAAACCGAGGGGCCTT | TGGTGAAAAC-GAGGGGCCTT | 17.3 | 19.9 | 18.6 | 1.8 |
|  | TGG------------ CCTT | TGGTGAAAACGAGGGGCCTT | 3.9 | 4 | 4 | 0.1 |
|  | -------------------- | TGGTGAAAACGAGGGGCCTT | 3.8 | 3.7 | 3.8 | 0.1 |
|  | -----------------CTT | TGGTGAAAACGAGGGGCCTT | 3.2 | 2.7 | 3 | 0.4 |
| 173 | TGG-----------GGCCTT | TGGTGAAAACGAGGGGCCTT | 3.3 | 2.7 | 3 | 0.4 |
| 174 | TGGTGA------GGGGCCTT | TGGTGAAAACGAGGGGCCTT | 3.6 | 2.3 | 3 | 0.9 |
|  | TGGTGAAA-CGAGGGGCCTT | TGGTGAAAACGAGGGGCCTT | 3.5 | 2.3 | 2.9 | 0.8 |
|  | T------------------- | TGGTGAAAACGAGGGGCCTT | 2.2 | 2.3 | 2.2 | 0.1 |
|  | TGG------------GCCTT | TGGTGAAAACGAGGGGCCTT | 1.7 | 1.6 | 1.6 | 0.1 |
|  | TGGTGAA------------- | TGGTGAAAACGAGGGGCCTT | 1 | 1.2 | 1.1 | 0.1 |

TABLE 17-continued

On-Target Gene Edited Sequences >1% Frequency in At Least One Gene Edited T Cell Donor for the TET2-exon3-T3 gRNA.
Reference on-target sequence[a]: TGGTGAAAACGAG(GGG)CCTT
(SEQ ID NO: 171)

| SEQ ID NO: | Gene Edited Sequence[b] | Reference Sequence[c] (SEQ ID NO: 171) | Donor 1 (%) | Donor 2 (%) | Mean (%) | Std. Dev. (%) |
|---|---|---|---|---|---|---|
| 175 | TGGTGAAA------------ | TGGTGAAAACGAGGGGCCTT | 1.3 | 0.9 | 1.1 | 0.3 |
|  | TGGTGAA--CGAGGGGCCTT | TGGTGAAAACGAGGGGCCTT | 1.1 | 0.9 | 1 | 0.1 |
|  | ----------------CCTT | TGGTGAAAACGAGGGGCCTT | 1.2 | 0.8 | 1 | 0.3 |
|  | ------------------TT | TGGTGAAAACGAGGGGCCTT | 0.7 | 1.1 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 18

On-Target Gene Edited Sequences >1% Frequency in At Least One Gene Edited T Cell donor for the TET2-exon6-BG5 gRNA.
Reference on-target sequence[a]: GCTCACCAATCGC(CGG)TGTG
(SEQ ID NO: 176)

| SEQ ID NO: | Gene Edited Sequence[b] | Reference Sequence[c] (SEQ ID NO: 176) | Donor 1 (%) | Donor 2 (%) | Mean (%) | Std. Dev. (%) |
|---|---|---|---|---|---|---|
|  | ----------CGCCGGTGTG | GCTCACCAATCGCCGGTGTG | 20.8 | 22 | 21.4 | 0.8 |
| 177 | GCTCACCAA-CGCCGGTGTG | GCTCACCAATCGCCGGTGTG | 7.3 | 8.2 | 7.8 | 0.6 |
| 178 | GCTCACCAATTCGCCGGTGTG | GCTCACCAA-TCGCCGGTGTG | 6.1 | 7.4 | 6.8 | 0.9 |
| 179 | GCTCACCA--CGCCGGTGTG | GCTCACCAATCGCCGGTGTG | 4.3 | 5.6 | 4.9 | 0.9 |
|  | -------------CGGTGTG | GCTCACCAATCGCCGGTGTG | 5.8 | 3.5 | 4.6 | 1.6 |
| 180 | GCTCA-------CCGGTGTG | GCTCACCAATCGCCGGTGTG | 3.6 | 3.8 | 3.7 | 0.1 |
| 181 | GCTCACC---CGCCGGTGTG | GCTCACCAATCGCCGGTGTG | 2.3 | 2.2 | 2.2 | 0.1 |
|  | -----------GCCGGTGTG | GCTCACCAATCGCCGGTGTG | 2.2 | 1.7 | 2 | 0.4 |
| 182 | GCTCAC----CGCCGGTGTG | GCTCACCAATCGCCGGTGTG | 2.3 | 1.5 | 1.9 | 0.6 |
|  | -------------------G | GCTCACCAATCGCCGGTGTG | 2.1 | 1.4 | 1.8 | 0.5 |
| 183 | GCTCACCAATACGCCGGTGTG | GCTCACCAAT-CGCCGGTGTG | 2 | 1.4 | 1.7 | 0.4 |
| 184 | GCTCA-----CGCCGGTGTG | GCTCACCAATCGCCGGTGTG | 1.3 | 1.8 | 1.6 | 0.4 |
| 185 | GCTCACCAATGCGCCGGTGTG | GCTCACCAAT-CGCCGGTGTG | 1.1 | 1.9 | 1.5 | 0.6 |
|  | -------------------- | GCTCACCAATCGCCGGTGTG | 2 | 0.9 | 1.4 | 0.8 |
|  | GCTCA--------------- | GCTCACCAATCGCCGGTGTG | 1.2 | 0.8 | 1 | 0.3 |
| 186 | GCTCACCAATCCGCCGGTGTG | GCTCACCAAT-CGCCGGTGTG | 1.2 | 0.5 | 0.8 | 0.5 |
| 187 | GCTCACCAATTCAAGGCACGCCGGTGTG | GCTCACCAAT--------CGCCGGTGTG | 1.1 | 0 | 0.6 | 0.8 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 19

On-Target Gene Edited Sequences >1% Frequency in At Least One Gene Edited T Cell Donor for the TET2-exon5-T1 gRNA. Reference on-target sequence[a]: CCTATTGCTAAGT(GGG)TAAG (SEQ ID NO: 188)

| SEQ ID NO: | Gene Edited Sequence[b] | Reference Sequence[c] (SEQ ID NO: 188) | Donor 1 (%) | Donor 2 (%) | Mean (%) | Std. Dev. (%) |
|---|---|---|---|---|---|---|
| 189 | CCTATTGCT-AGTGGGTAAG | CCTATTGCTAAGTGGGTAAG | 10.1 | 9.6 | 9.8 | 0.4 |
| 190 | CCTATTGCTAAAGTGGGTAAG | CCTATTGCT-AAGTGGGTAAG | 7.4 | 9.3 | 8.4 | 1.3 |
| 191 | CCTAT-------TGGGTAAG | CCTATTGCTAAGTGGGTAAG | 6.9 | 6 | 6.4 | 0.6 |
|  | -------------------- | CCTATTGCTAAGTGGGTAAG | 4.1 | 5.8 | 4.9 | 1.2 |
|  | ----------AGTGGGTAAG | CCTATTGCTAAGTGGGTAAG | 4 | 4.8 | 4.4 | 0.6 |
|  | -------------GGGTAAG | CCTATTGCTAAGTGGGTAAG | 3.7 | 2.2 | 3 | 1.1 |
| 192 | CCTATTGC--AGTGGGTAAG | CCTATTGCTAAGTGGGTAAG | 2.3 | 1.8 | 2 | 0.4 |
|  | ---------------GTAAG | CCTATTGCTAAGTGGGTAAG | 1.9 | 1.9 | 1.9 | 0 |
|  | CCTATTGCTA---------- | CCTATTGCTAAGTGGGTAAG | 1.1 | 2 | 1.6 | 0.6 |
| 193 | C---------AGTGGGTAAG | CCTATTGCTAAGTGGGTAAG | 1.3 | 1.8 | 1.6 | 0.4 |
|  | --------------GGTAAG | CCTATTGCTAAGTGGGTAAG | 1.4 | 1.5 | 1.4 | 0.1 |
| 194 | CCTATTGC--------TAAG | CCTATTGCTAAGTGGGTAAG | 1.5 | 1.4 | 1.4 | 0.1 |
| 195 | CCTATTGCTATAGTGGGTAAG | CCTATTGCTA-AGTGGGTAAG | 1.4 | 1.3 | 1.4 | 0.1 |
|  | CCTAT--------------- | CCTATTGCTAAGTGGGTAAG | 1.1 | 1.5 | 1.3 | 0.3 |
| 196 | CCTATTG---AGTGGGTAAG | CCTATTGCTAAGTGGGTAAG | 1.2 | 1.2 | 1.2 | 0 |
|  | ------------TGGGTAAG | CCTATTGCTAAGTGGGTAAG | 0.9 | 1.4 | 1.2 | 0.4 |
| 197 | CC--------AGTGGGTAAG | CCTATTGCTAAGTGGGTAAG | 1.2 | 1.2 | 1.2 | 0 |
|  | -----------GTGGGTAAG | CCTATTGCTAAGTGGGTAAG | 1.8 | 0.7 | 1.2 | 0.8 |
| 198 | CCTATT-----GTGGGTAAG | CCTATTGCTAAGTGGGTAAG | 1.5 | 0.8 | 1.2 | 0.5 |
| 199 | CCT-------AGTGGGTAAG | CCTATTGCTAAGTGGGTAAG | 1 | 1.3 | 1.2 | 0.2 |
| 200 | CCTAT-----AGTGGGTAAG | CCTATTGCTAAGTGGGTAAG | 1.2 | 1 | 1.1 | 0.1 |
|  | CCTA---------------- | CCTATTGCTAAGTGGGTAAG | 0.7 | 1.2 | 1 | 0.4 |
| 201 | CCTATTGCTA--TGGGTAAG | CCTATTGCTAAGTGGGTAAG | 1.3 | 0.7 | 1 | 0.4 |
|  | CC--------------TAAG | CCTATTGCTAAGTGGGTAAG | 0.9 | 1.2 | 1 | 0.2 |
| 202 | CCTATTGCTACAGTGGGTAAG | CCTATTGCTA-AGTGGGTAAG | 0.9 | 1.1 | 1 | 0.1 |
|  | ---------AAGTGGGTAAG | CCTATTGCTAAGTGGGTAAG | 1.1 | 0.8 | 1 | 0.2 |
| 203 | CCTATTGCTA------TAAG | CCTATTGCTAAGTGGGTAAG | 1.2 | 0.5 | 0.8 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 20

On-Target Gene Edited Sequences >1% Frequency in At Least One
Gene Edited T Cell Donor for the TET2-exon5-T2 gRNA.
Reference on-target sequence[a]: TCCTATTGCTAAG(TGG)GTAA
(SEQ ID NO: 204)

| SEQ ID NO: | Gene Edited Sequence[b] | Reference Sequence[c] (SEQ ID NO: 204) | Donor 1 (%) | Donor 2 (%) | Mean (%) | Std. Dev. (%) |
|---|---|---|---|---|---|---|
| 205 | TCCTATTGCTTAAGTGGGTAA | TCCTATTGC-TAAGTGGGTAA | 60.7 | 67.1 | 63.9 | 4.5 |
| 206 | TCCTAT---TAAGTGGGTAA | TCCTATTGCTAAGTGGGTAA | 2.5 | 1.7 | 2.1 | 0.6 |
|  | ---------------GGGTAA | TCCTATTGCTAAGTGGGTAA | 2.6 | 1.5 | 2 | 0.8 |
| 207 | TCCTATTGC-AAGTGGGTAA | TCCTATTGCTAAGTGGGTAA | 2.1 | 1.5 | 1.8 | 0.4 |
|  | -------------------- | TCCTATTGCTAAGTGGGTAA | 1.9 | 1.8 | 1.8 | 0.1 |
| 208 | TCCTATTG-TAAGTGGGTAA | TCCTATTGCTAAGTGGGTAA | 1.6 | 1.5 | 1.6 | 0.1 |
| 209 | TCCTAT-------TGGGTAA | TCCTATTGCTAAGTGGGTAA | 1.7 | 1 | 1.4 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 21

On-Target Gene Edited Sequences >1% Frequency in At Least One
Gene Edited T Cell Donor for the TET2-exon4-BG4 gRNA.
Reference on-target sequence[a]: ACCTGCTCCTAGA(TGG)GTAT
(SEQ ID NO: 210)

| SEQ ID NO: | Gene Edited Sequence[b] | Reference Sequence[c] (SEQ ID NO: 210) | Donor 1 (%) | Donor 2 (%) | Mean (%) | Std. Dev. (%) |
|---|---|---|---|---|---|---|
| 211 | ACCTGCTCCTTAGATGGGTAT | ACCTGCTCCT-AGATGGGTAT | 48.4 | 51.3 | 49.8 | 2.1 |
|  | ACCT---------------- | ACCTGCTCCTAGATGGGTAT | 8.6 | 6.4 | 7.5 | 1.6 |
| 212 | ACCTGCTCC-AGATGGGTAT | ACCTGCTCCTAGATGGGTAT | 3.8 | 3.3 | 3.6 | 0.4 |
| 213 | ACCTGCT---AGATGGGTAT | ACCTGCTCCTAGATGGGTAT | 2.7 | 3.5 | 3.1 | 0.6 |
|  | ACCTG----------GGTAT | ACCTGCTCCTAGATGGGTAT | 2.4 | 2.2 | 2.3 | 0.1 |
|  | -------------------- | ACCTGCTCCTAGATGGGTAT | 2.2 | 2 | 2.1 | 0.1 |
| 214 | ACCTGCTC-TAGATGGGTAT | ACCTGCTCCTAGATGGGTAT | 1.7 | 1 | 1.4 | 0.5 |
|  | A------------TGGGTAT | ACCTGCTCCTAGATGGGTAT | 1.2 | 1.3 | 1.2 | 0.1 |
| 215 | ACCTG----TAGATGGGTAT | ACCTGCTCCTAGATGGGTAT | 1.5 | 0.7 | 1.1 | 0.6 |
| 216 | ACCTGCTCCTA--TGGGTAT | ACCTGCTCCTAGATGGGTAT | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence Example 8

TET2 Knock-Out in Anti-BCMA CAR-T Cells Confer Growth Advantage and CAR-T Enrichment Chimeric antigen receptor (CAR) T-cell therapy uses genetically modified T cells to target and kill cancer cells more specifically and efficiently. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

This example further explores advantageous features arising from TET2 knock-out via gene editing in CAR-T cells, for example, with multiple rounds of target antigen stimulation.

(1) Generating TET2 KO (TET2−) or TET2 W7' (TET2+) anti-BCMA CAR-T Cells

Activated primary human T cells were electroporated (EP1) with Cas9: TET2 sgRNA 1 RNP complex to generate a polyclonal TET2 KO population. 72 hours later these cells or wild type (WT) activated primary T cells were electroporated again (EP2) with Cas9: gRNA RNP complexes (RNPs) and adeno-associated adenoviral vectors (AAVs) to generate TET2−/TRAC−/β2M−/anti-BCMA CAR+ (TET2−/anti-BCMA CAR) or TRAC−/β2M−/anti-BCMA CAR+ T cells (TET2+/anti-BCMA CAR). Two control groups were generated where either AAV or RNP were excluded in EP2 (TET2−/AAV− and TET2−/RNP−, respectively). Recombinant AAV serotype 6 (AAV6) comprising one of the nucleotide sequences encoding an anti-BCMA CAR (SEQ ID NO: 149) were delivered with Cas9:sgRNA RNPs (1 μM Cas9, 5 μM gRNA) to activated allogeneic human T cells. The following sgRNAs were used: TET2 (SEQ ID NO: 13), TRAC (SEQ ID NO: 93) and β2M (SEQ ID NO: 97).

About one (1) week post electroporation (EP1), cells were assessed for TET2 protein knockdown by automated Western blot (Wes™, Proteinsimple) using anti-TET2 polyclonal antibody (Diagenode #C15410255-100) at 1:500 dilution. The results obtained from this assay confirm no detection of TET2 in TET2 KO (TET2−) anti-BCMA CAR-T cells, while TET2 expression was detected in control cells and in TET2 WT (TET2+) anti-BCMA CAR-T cells.

On Day 9 after EP2 the cells were also processed for flow cytometry to assess TRAC and β2M knockout levels, and anti-BCMA CAR expression levels at the cell surface of the edited cell population. The cells were stained with a panel of antibodies indicated in Table 22 below.

TABLE 22

Antibody Panel for Detecting CAR-T Cell Surface Proteins

| Antibody | Source | Fluor | Dilution |
| --- | --- | --- | --- |
| IgG, F(ab')$_2$ fragment specific | Jackson Immunoresearch, #109-006-097 | Biotinylated; detected with SA-APC | 1:20 |
| TCRαβ | Miltenyi, #130-099-661 | PE | 1:100 |
| β2M | Biolegend, #316318 | PECy7 | 1:100 |
| CD8 | Biolegend, #344742 | BV605 | 1:100 |
| CD4 | Biolegend, #300546 | BV510 | 1:100 |
| Streptavidin-APC (SA-APC) | ThermoFisher (eBioscience), #17-4317-82 | APC | 1:100 |
| 7-AAD | BD Biosciences, 559925 | PerCP range | 1:500 |

The results are shown in Table 23 below. For all anti-BCMA CAR-T cells and TRAC−/β2M-control cells (TET2−/AAV−), >85% of viable cells lacked expression of TCR and >74% lacked expression of β2M, with >72% of anti-BCMA CAR-T cell populations being both TRAC−/B2M−. Live CAR-T cells were gated by their forward scatter (FSC) and side scatter (SSC) profiles, and with 7-AAD dye.

TABLE 23

Percent positive populations of surface anti-BCMA CAR expression and TRAC/B2M knockdown 9 days after EP2

| Sample | % BCMA CAR positive | TRAC− | B2M− | TRAC−B2M−− |
| --- | --- | --- | --- | --- |
| TET2−/anti-BCMA CAR-T | 34.80% | 89.50% | 81.90% | 74.70% |
| TET2+/anti-BCMA CAR-T | 41.30% | 85.00% | 83.20% | 72.30% |
| TET2−/AAV− | 0.11% | 84.90% | 74.70% | 63.80% |
| TET2−/RNP− | 0.62% | 11.27% | 0.18% | 0.07% |

(II). Antigen Stimulation of TET2 KO (TET2−) or TET2 WT (TET2+) Anti-BCMA CAR-T Cells The different cell populations were expanded for a week after determining CAR expression. 1 million cells of each CAR-T population (TET2−/anti-BCMA CAR-T, TET2+/anti-BCMA CAR-T, TET2−/AAV− and TET2−/RNP−) were then co-cultured with target cell line MM.1S at a 1:1 E:T ratio, in triplicate, in a 12-well tissue culture plate in full T cell media, and incubated at 37° C. for 48 hours (stimulation round 1) or 72 hours (stimulation rounds 2 & 3), a sufficient time period previously established to ensure all target cells were killed by the cocultured CAR-T cells. A total of 3 rounds of stimulation were performed where, after each stimulation CAR-T cells were collected, washed, counted with Trypan Blue (for viability assessment) and replated at 1 million cells/well with fresh target cells at an E:T of 1:1, in triplicate. Additionally, a portion of the cells were evaluated for CAR-T expression by FACS using an antibody panel indicated in Table 24 below. After 3 rounds of stimulation, CAR-T cells were collected and expanded to monitor for growth and % viability, as well as periodic FACS evaluation of surface CAR expression using the antibody panel indicated in Table 24.

TABLE 24

Antibody Panel for Detecting CAR-T Cell Surface Proteins

| Antibody | Source | Fluor | Dilution |
| --- | --- | --- | --- |
| Anti-BCMA CAR | US63/069889 | APC | 1:100 |
| CD8 | Biolegend, #344742 | BV605 | 1:100 |
| CD4 | Biolegend, #300546 | BV510 | 1:100 |
| CD57 | BioLegend, #322306 | FITC | 1:100 |
| Lag3 | BioLegend, #369310 | PE-Cy7 | 1:100 |
| CD45RA | BioLegend, #304128 | APC-Cy7 | 1:100 |
| CCR7 | BioLegend, #353210 | PacBlue | 1:100 |
| PD1 | BioLegend, #329906 | PE | 1:100 |
| 7-AAD | BD Biosciences, #559925 | PerCP range | 1:500 |

Figure 8A:
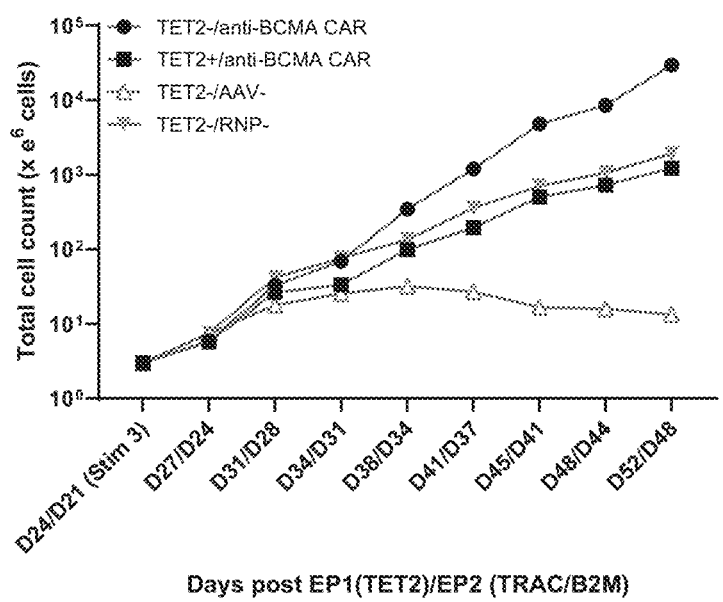
FIGS. 8A-8D include graphs showing advantageous features conferred by TET KO in anti-BCMA CAR-T cells as compared with TET WT anti-BCMA CAR-T cells.
Figure 8B:
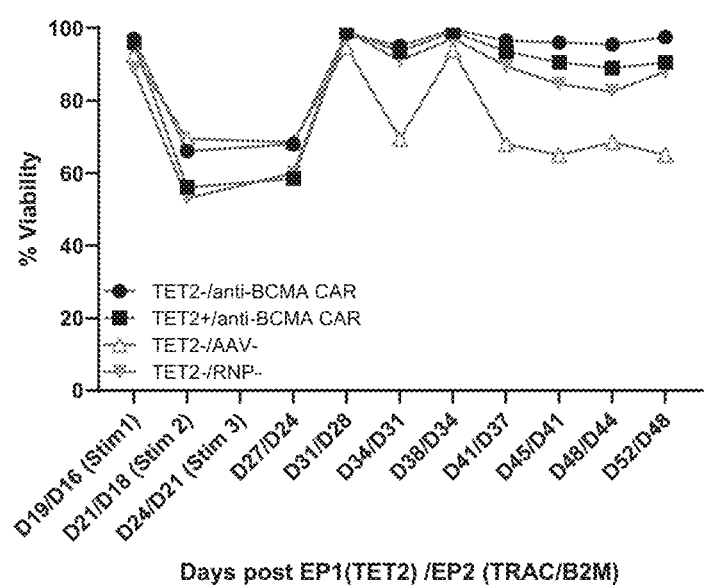
Figure 8C:
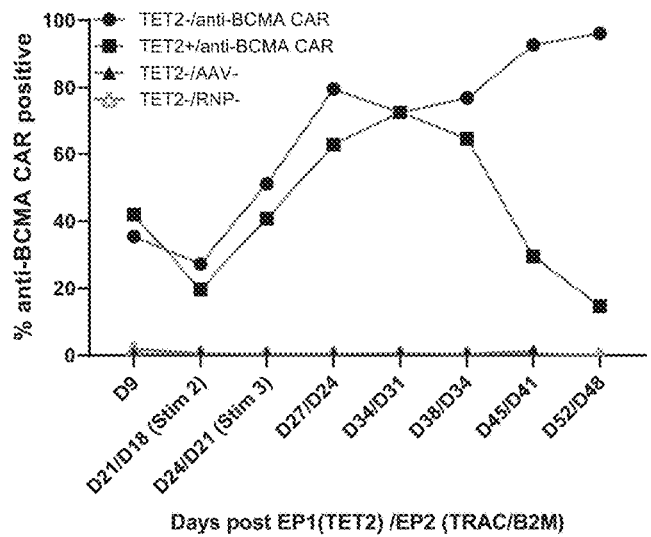

The results of extended culture of these anti-BCMA CAR-T populations indicate that knocking out TET2 in T cells confers a proliferative advantage to CAR-T cells that have been stimulated with a target cell line (FIG. 8A), without a significant difference in overall viability (FIG. 8B). Additionally, a preferential enrichment of BCMA CAR-T positive cells in the TET2 KO cells was observed as compared to TET2+/anti-BCMA CAR-T cells or non-stimulated cells (FIG. 8C).

(III). Comparison of Functional Features Between TET2 KO Anti-BCMA CAR-T Cells (TET2−/Anti-BCMA CAR T) and TET2 WT Anti-BCMA CAR-T Cells (TET2+/Anti-BCMA CAR T)

Functional activity of anti-BCMA CAR T cells (evidenced by effector cytokine secretion) was assessed using cytokine release assays for Interferon gamma (IFNγ) after each round of target cell stimulation. After above-mentioned periods of coculture, supernatant media from the co-cultured cells were collected and the levels of IFNγ was measured using an ELISA (RD Systems) following the manufacturer's instructions. The MILLIPLEX kit (Millipore, catalog #HCYTOMAG-60K) using magnetic microspheres, HCYIFNG-MAG (Millipore, catalog #HCYIFNG-MAG) was used to quantify IFN-γ secretion in samples from the cocultured stimulation assay. The assay was conducted following manufacturer's protocol.

In short, MILLIPLEX® standard and quality control (QC) samples were reconstituted, and serial dilutions of the working standards from 10,000 pg/mL to 3.2 pg/mL were prepared. MILLIPLEX® standards, QCs and cell supernatants were added to each plate, and assay media was used to dilute the supernatants. All samples were incubated with HCYIFNG-MAG beads for 2 hours. After incubation, the plate was washed using an automated magnetic plate washer. Human cytokine/chemokine detection antibody solution was added to each well and incubated for 1 hour followed by incubation with Streptavidin-Phycoerythrin for 30 minutes. The plate was subsequently washed, samples were resuspended with 150 µL Sheath Fluid, and agitated on a plate shaker for 5 minutes. The samples were read using the Luminex® 100/200™ instrument with xPONENT® software and data acquisition and analysis was completed using MILLIPLEX® Analyst software. The Median Fluorescent Intensity (MFI) data is automatically analyzed using a 5-parameter logistic curve-fitting method for calculating the cytokine concentration measured in the unknown samples.

Figure 8D:
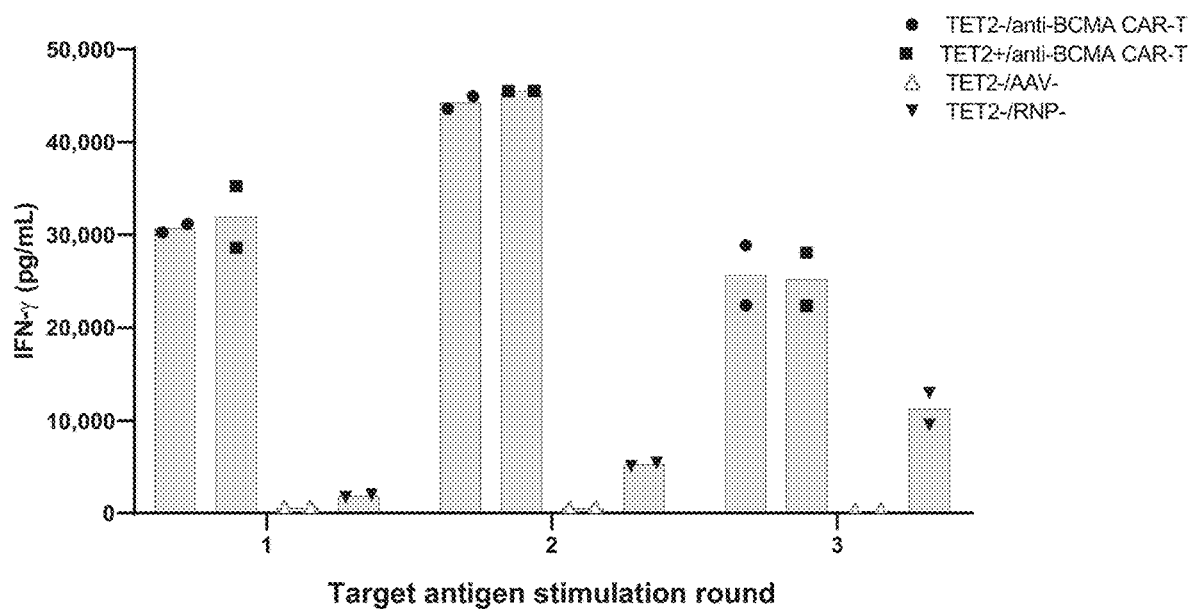

Results showed that there was no significant difference in IFNγ secretion in anti-BCMA CAR-T cells with or without TET2 KO after multiple rounds of target cell line stimulation under these conditions (FIG. 8D). The control cells TCR-/β2M- (AAV negative) and non-CAR edited (RNP negative) showed no significant or specific IFNγ secretory response in the presence of MM1S cells.

Example 9

On-Target and Off-Target Editing of FAS Guide RNAs

On-target and off-target editing efficiencies of various FAS-targeting gRNAs were examined for the three guides exhibiting the highest gene editing efficiency FAS-ex2_T2, FAS-ex3_T1, FAS-ex3_T2 (see FIG. 2A). Briefly, activated T cells derived from primary human PBMC cells were transfected (electroporated) with a ribonucleoprotein particle (RNP) containing Cas9 nuclease and a synthetic modified sgRNA targeting the FAS gene (sequences in Table 5 above) or prepared as untreated controls (no electroporation, no Cas9, no gRNA).

For genomic on- and off-target assessment, the same electroporation methods were used to generate two cell populations of edited cells from two different donor T cells (termed 1 and 2). Cells were gene edited with three of the top guides listed in Table 5, and then collected ten (10) days post transfection. These samples were analyzed with hybrid capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions indicating repair following CRISPR editing.

The results are provided in Table 25 below.

TABLE 25

On and Off Target Results by Hybrid Capture

| Guide | gRNA target sequence + (PAM) | Number of predicted off target sites tested | n-target mean editing hyb cap (%)[a] | Detected off-targets |
|---|---|---|---|---|
| FAS-ex2_T2 | CACTTGGGCATTAACACTTT (TGG) (SEQ ID NO: 88) | 172 | 98.6 | One intergenic 1.1%, one 0.6% off-target |
| FAS-ex3_T1 | CTAGGGACTGCACAGTCAAT (GGG) (SEQ ID NO: 90) | 146 | 95.3 | None |
| FAS-ex3_T2 | ACTGCGTGCCCTGCCAAGAA (GGG) (SEQ ID NO: 91) | 111 | 99.2 | None |

[a]Average across donors 1 and 2.

In summary, the studies described above show that: (a) TET2 KO anti-BCMA CAR-T cells (TET2−/anti-BCMA CAR T) showed a growth advantage over TET2 WT anti-BCMA CAR T cells (TET2+/anti-BCMA CAR T) after MM1S antigen stimulation; (b) TET2 KO anti-BCMA CAR-T cells showed an enrichment for anti-BCMA CAR positive cells over TET2 WT anti-BCMA CAR T cells post antigen stimulation; and (c) TET2 KO did not alter anti-BCMA CAR-T functional activity (IFNγ secretion) compared to TET2 WT anti-BCMA CAR T cells with multiple antigen stimulation. These results have demonstrated that engineering a TET2 knockout in CAR-T cells (using anti-BCMA CAR-T cells as an example here) confers both a growth advantage and CAR-T enrichment effect. This provides proof of concept evidence that boosting CAR-T cell proliferation in vitro by gene editing is feasible and can be used to generate a cell bank capable of higher CAR-T yield without compromising function.

Analysis of On-Target Indel Profiles in T Cells

The data used to quantify off-target editing were also used to quantify and summarize the most frequent on-target indels for all FAS guides listed in Table 25. This data was generated from hybrid capture of the FAS locus combined with next-generation sequencing in two donors (termed Donor 1 and Donor 2).

Following gene editing, hybrid capture analysis of the FAS locus in a population of T cells following CRISPR/Cas9 gene editing to produce FAS-T cells results in specific indel frequencies and edited gene sequences at the FAS locus (Tables 26-28; deletions as dashes and insertions in bold).

For the purposes of individual sequence quantification from hybrid capture data, sequence reads aligning across the FAS on-target site, 20 bp upstream and downstream of the cut site, were selected and considered for indel sequence quantification. From the selected reads, the sequence within 10 bp upstream and downstream of each putative cut site (~3bp upstream of the PAM (Jinek, et al., Science 2012) was quantified as a representative region of on-target non-homologous end joining (NHEJ) editing. The data on these on-target gene edited sequences is presented in the tables below, with the frequencies of these sequences representing the percent of all sequences spanning the on-target site within 20 bp upstream and downstream of each cut site. The indels for each guide are shown relative to an on-target reference sequence in Tables 22-24. The reference sequence is centered on the cleavage site with 10 bp in either direction, ending 4 bp 3' of the PAM.

TABLE 26

On-Target Gene Edited Sequences >1% Frequency in At Least One Gene Edited T Cell Donor for the FAS-Exon2-T2 gRNA.
Reference on-target sequence[a]: GCATTAACACTTT(TGG)ACGA
(SEQ ID NO: 217)

| SEQ ID NO: | Gene Edited Sequence[b] | Reference Sequence[c] | Donor 1 (%) | Donor 2 (%) | Mean (%) | Std. Dev. (%) |
|---|---|---|---|---|---|---|
| 218 | GCATTAACACTTTTTGGACGA | GCATTAACACTTTT-GGACGA | 43.3 | 40.4 | 41.8 | 2.1 |
| 219 | GCATTAACACTTTTTTGGACGA | GCATTAACACTTTT--GGACGA | 19.6 | 18.1 | 18.8 | 1.1 |
|  | ----------------ACGA | GCATTAACACTTTTGGACGA | 3.4 | 5.4 | 4.4 | 1.4 |
| 220 | GCATTAACA-TTTTGGACGA | GCATTAACACTTTTGGACGA | 3.7 | 4.4 | 4.1 | 0.5 |
|  | -------------------- | GCATTAACACTTTTGGACGA | 2.1 | 2.3 | 2.2 | 0.1 |
|  | GCATTAA------------- | GCATTAACACTTTTGGACGA | 2.0 | 1.8 | 1.9 | 0.1 |
|  | GCA----------------- | GCATTAACACTTTTGGACGA | 1.3 | 1.7 | 1.5 | 0.3 |
| 221 | GCATTAACACTTT-GGACGA | GCATTAACACTTTTGGACGA | 1.4 | 1.3 | 1.4 | 0.1 |
| 222 | GCATTA----TTTTGGACGA | GCATTAACACTTTTGGACGA | 1.1 | 1.6 | 1.4 | 0.4 |
| 223 | GCATTAACACTTTTTTTGGACGA | GCATTAACACTTTT---GGACGA | 1.4 | 1.1 | 1.2 | 0.2 |
| 224 | GCATTAAC--TTTTGGACGA | GCATTAACACTTTTGGACGA | 1.0 | 1.2 | 1.1 | 0.1 |
|  | GCAT---------------- | GCATTAACACTTTTGGACGA | 0.7 | 1.1 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 27

On-Target Gene Edited Sequences >1% Frequency in At Least One Gene Edited T Cell Donor for the FAS-Exon3-T1 gRNA.
Reference on-target sequence[a]: CTGCACAGTCAAT(GGG)GATG
(SEQ ID NO: 225)

| SEQ ID NO: | Gene Edited Sequence[b] | Reference Sequence[c] | Donor 1 (%) | Donor 2 (%) | Mean (%) | Std. Dev. (%) |
|---|---|---|---|---|---|---|
|  | -------------------- | CTGCACAGTCAATGGGGATG | 24.9 | 19.1 | 22.0 | 4.1 |
| 226 | CTGCACAGTCAAATGGGGATG | CTGCACAGTC-AATGGGGATG | 5.6 | 7.1 | 6.4 | 1.1 |
| 227 | CTGCACAGTCCAATGGGGATG | CTGCACAGT-CAATGGGGATG | 5.1 | 4.2 | 4.6 | 0.6 |
|  | --------------GGGATG | CTGCACAGTCAATGGGGATG | 4.1 | 4.5 | 4.3 | 0.3 |
| 228 | CTGCA----CAATGGGGATG | CTGCACAGTCAATGGGGATG | 3.8 | 4.0 | 3.9 | 0.1 |
| 229 | CTGCACAGTC-ATGGGGATG | CTGCACAGTCAATGGGGATG | 3.1 | 2.9 | 3.0 | 0.1 |
|  | CTGCA--------------- | CTGCACAGTCAATGGGGATG | 2.8 | 3.2 | 3.0 | 0.3 |
| 230 | CTGCACAGT-AATGGGGATG | CTGCACAGTCAATGGGGATG | 2.5 | 3.3 | 2.9 | 0.6 |
| 231 | CTGCACA---AATGGGGATG | CTGCACAGTCAATGGGGATG | 2.6 | 2.9 | 2.8 | 0.2 |

TABLE 27-continued

On-Target Gene Edited Sequences >1% Frequency in At Least One
Gene Edited T Cell Donor for the FAS-Exon3-T1 gRNA.
Reference on-target sequence[a]: CTGCACAGTCAAT(GGG)GATG
(SEQ ID NO: 225)

| SEQ ID NO: | Gene Edited Sequence[b] | Reference Sequence[c] | Donor 1 (%) | Donor 2 (%) | Mean (%) | Std. Dev. (%) |
|---|---|---|---|---|---|---|
| 232 | CTG-------CATGGGGATG | CTGCACAGTCAATGGGGATG | 1.8 | 2.1 | 2.0 | 0.2 |
|  | C-----------------TG | CTGCACAGTCAATGGGGATG | 1.9 | 2.0 | 2.0 | 0.1 |
|  | CTGC---------------- | CTGCACAGTCAATGGGGATG | 1.8 | 1.7 | 1.8 | 0.1 |
| 233 | CTGCACAG--AATGGGGATG | CTGCACAGTCAATGGGGATG | 1.1 | 2.5 | 1.8 | 1.0 |
|  | -------------------G | CTGCACAGTCAATGGGGATG | 1.5 | 1.8 | 1.6 | 0.2 |
|  | -------------GGGGATG | CTGCACAGTCAATGGGGATG | 1.2 | 1.8 | 1.5 | 0.4 |
| 234 | CTGCACAGTC--TGGGGATG | CTGCACAGTCAATGGGGATG | 1.4 | 1.3 | 1.4 | 0.1 |
|  | CTGCACAGT----------- | CTGCACAGTCAATGGGGATG | 1.0 | 1.5 | 1.2 | 0.4 |
| 235 | CTGCACAGTC---------- | CTGCACAGTCAATGGGGATG | 1.0 | 1.4 | 1.2 | 0.3 |
| 236 | ----------AATGGGGATG | CTGCACAGTCAATGGGGATG | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 28

On-Target Gene Edited Sequences >1% Frequency in At Least One
Gene Edited T Cell Donor for the FAS-Exon3-T2 gRNA.
Reference on-target sequence[a]: GCCCTGCCAAGAA(GGG)AAGG
(SEQ ID NO: 237)

| SEQ ID NO: | Gene Edited Sequence[b] | Reference Sequence[c] | Donor 1 (%) | Donor 2 (%) | Mean (%) | Std. Dev. (%) |
|---|---|---|---|---|---|---|
| 238 | GCCCTGCCAAAGAAGGGAAGG | GCCCTGCC-AAGAAGGGAAGG | 45.7 | 37.6 | 41.7 | 5.7 |
| 239 | GCCCTGCC-AGAAGGGAAGG | GCCCTGCCAAGAAGGGAAGG | 19.4 | 26.6 | 23.0 | 5.1 |
|  | -------------------- | GCCCTGCCAAGAAGGGAAGG | 9.6 | 9.2 | 9.4 | 0.3 |
|  | G------------------- | GCCCTGCCAAGAAGGGAAGG | 1.1 | 1.4 | 1.2 | 0.2 |
| 240 | GCCCTGCCAAAAGAAGGGAAGG | GCCCTGCC--AAGAAGGGAAGG | 1.2 | 0.9 | 1.0 | 0.2 |
| 241 | GCCCT----AGAAGGGAAGG | GCCCTGCCAAGAAGGGAAGG | 0.5 | 1.1 | 0.8 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence Example 10

Derivation of an Allogeneic Human CD19 CAR-T Cell Line

Splenocytes were isolated from 3 mice that had been dosed with TRAC-/B2M-/FAS-/TET2−/CD70-anti CD19 CAR-expressing T cells (produced from a healthy human donor's peripheral blood T cells). These mice had controlled Nalm6 leukemia >3 months post infusion. The isolated splenocytes were cultured in human T cell media containing IL2/IL7 and human serum and outgrowths of cells were monitored. Cells from one of the mouse spleen isolates showed outgrowth over time (these cells are referred to as: isolated cells). These isolated cells were >99% TRAC-/B2M-/CAR+ and had a CD4 phenotype along with high frequency indels at FAS, CD70, TET2 after 2 months of culture. More specifically, FACS analysis showed that 97.8% are live cells, 99.1% are TCR and B2M negative, 99.1% are CAR positive, and 99.8% are CD4 positive in the tested cell population.

Figure 9A:
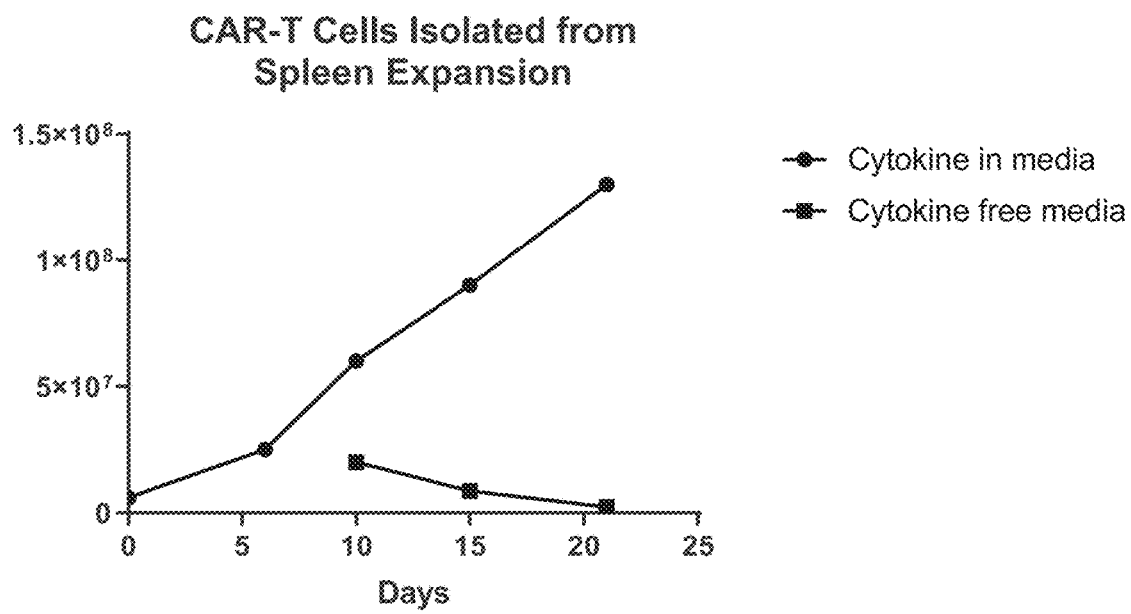
FIGS. 9A-9E include diagrams showing persistence of allogenic human anti-CD19 CAR-T cells having disrupted TET2, FAS, and CD70 genes.
Figure 9B:
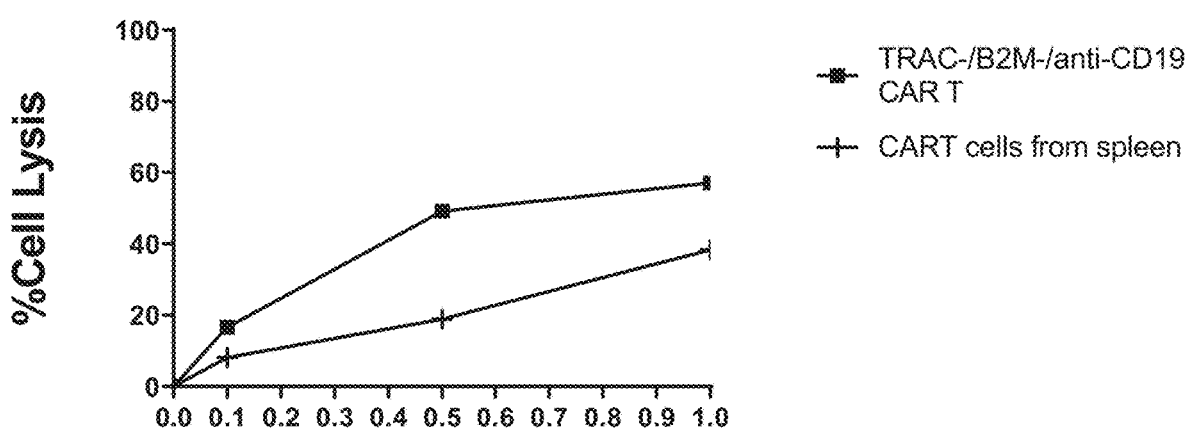
Figure 9C:
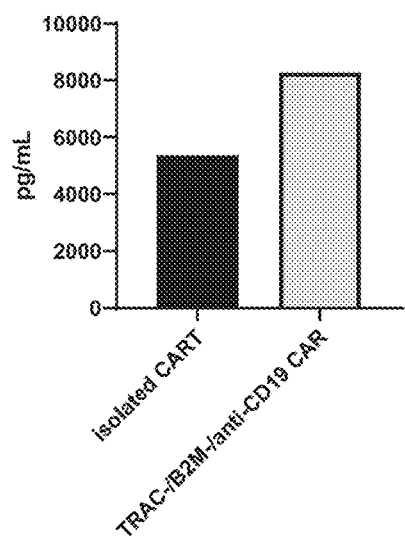
Figure 9D:
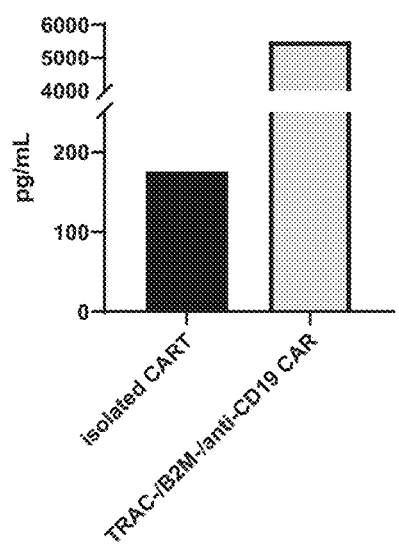
Figure 9E:
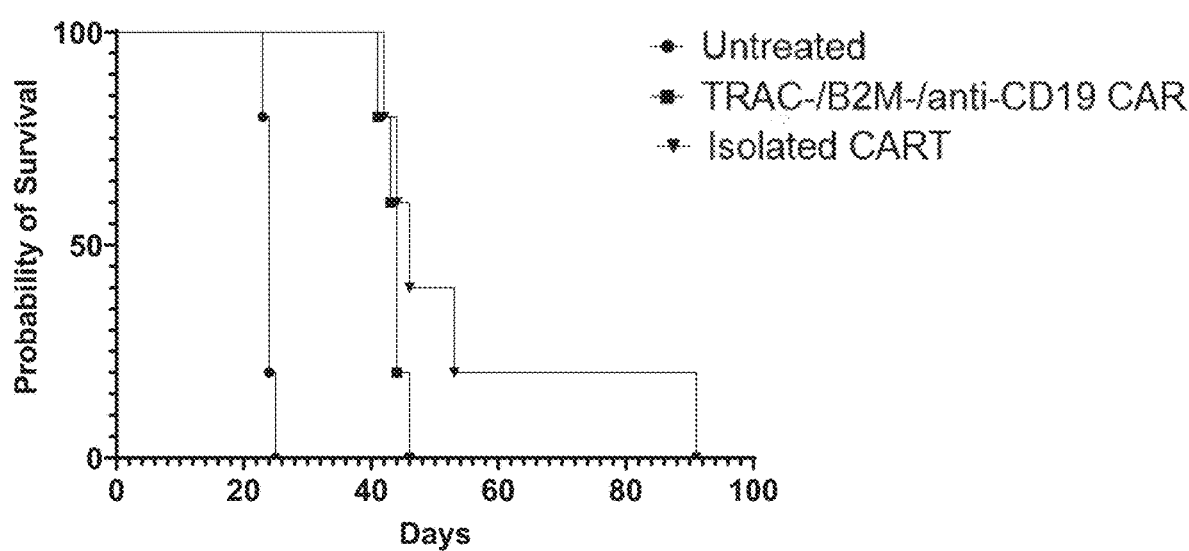

The isolated cells maintained their dependency on human cytokines IL2 and IL7 (FIG. 9A). These cells also retain their ability to kill CD19+ cells (FIG. 9B) and further maintained cytotoxic and cytokine release functions in vitro (FIGS. 9C and 9D, respectively). The isolated cells were again reinjected into a Nalm6-leukemia model and showed efficacy comparable to a fresh lot of TRAC-/B2M-/anti-CD19 CAR T cells. (FIG. 9E).

Following this second round of in vivo testing with the isolated cells, cells were again isolated from 1 mouse and further cultured/expanded for several weeks in cytokine containing media. These re-isolated cells maintained the same phenotype as the cells from the initial in vivo isolation. The re-isolated cells are used in a second experiment to assess their ability to control Nalm6 leukemia.

This example suggests that persistent T cell lines can be produced from normal healthy donor (e.g., human donor) derived peripheral blood T cells that maintain functionality in vitro and in vivo and have the potential to serve as a cell bank and/or therapeutic.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same FAShion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A population of genetically engineered T cells, comprising:
   (i) a disrupted Ten-Eleven Translocation-2 (TET2) gene;
   (ii) a disrupted T cell receptor alpha chain constant region (TRAC) gene;
   (iii) a disrupted beta-2-microglobulin (β2M) gene;
   (iv) a disrupted CD70 gene; and
   (v) a disrupted FAS Cell Surface Death Receptor (FAS) gene;
   wherein the population of genetically engineered T cells, as compared to non-engineered T cell counterparts, have the following features: (a) enhanced expansion capacity in culture, (b) enhanced proliferation capacity in vivo, (c) a reduced apoptosis level in vivo, and (d) an enhanced frequency of activation.

2. The population of genetically engineered T cells of claim 1, wherein the disrupted TET2 gene is genetically edited in an exon selected from the group consisting of exon 1, exon 3, exon 4, exon 5, and exon 6, or a combination thereof.

3. The population of genetically engineered T cells of claim 1, wherein the disrupted TET2 gene is genetically edited by CRISPR/Cas-mediated gene editing.

4. The population of genetically engineered T cells of claim 3, wherein the disrupted TET2 gene is genetically edited by CRISPR/Cas-mediated gene editing with a guide RNA (gRNA) comprising a nucleotide sequence of SEQ ID NO: 14, 18, 22, 26, 112, 116, or 120.

5. The population of genetically engineered T cells of claim 1, wherein the disrupted FAS and/or CD70 gene is genetically edited by CRISPR/Cas-mediated gene editing.

6. The population of genetically engineered T cells of claim 5, wherein the disrupted FAS gene is genetically edited by CRISPR/Cas-mediated gene editing with a guide RNA (gRNA) comprising the nucleotide sequence of SEQ ID NO: 69, 73, 77, 81, or 85, and/or wherein the disrupted CD70 gene is genetically edited by CRISPR/Cas-mediated gene editing with a gRNA comprising the nucleotide sequence of SEQ ID NO: 34, 38, 42, 46, 50, 54, or 58.

7. The population of genetically engineered T cells of claim 1, wherein the T cells are further engineered to express a chimeric antigen receptor (CAR).

8. The population of genetically engineered T cells of claim 7, wherein the CAR targets a tumor antigen.

9. The population of genetically engineered T cells of claim 8, wherein the tumor antigen is CD19, B cell maturation antigen (BCMA), or CD70.

10. The population of genetically engineered T cells of claim 7, wherein the T cells comprise a nucleic acid encoding the CAR, and wherein the nucleic acid is inserted in the genome of the T cells.

11. The population of genetically engineered T cells of claim 10, wherein the disrupted TRAC gene has an insertion of the nucleotide acid encoding the chimeric antigen receptor.

12. The population of genetically engineered T cells of claim 1, wherein the T cells are derived from primary T cells of one or more human donors.

13. The population of genetically engineered T cells of claim 1, wherein the T cells show cytokine-dependent growth.

* * * * *